(12) United States Patent
Landry et al.

(10) Patent No.: US 10,899,756 B2
(45) Date of Patent: *Jan. 26, 2021

(54) PHOSPHODIESTERASE INHIBITORS AND USES THEREOF

(71) Applicant: The Trustees of Columbia University in the City of New York, New York, NY (US)

(72) Inventors: Donald W. Landry, New York, NY (US); Shixian Deng, White Plains, NY (US); Ottavio Arancio, New York, NY (US); Jole Fiorito, New York, NY (US); Andrew Wasmuth, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/905,246

(22) PCT Filed: Jul. 17, 2014

(86) PCT No.: PCT/US2014/047031
§ 371 (c)(1),
(2) Date: Jan. 14, 2016

(87) PCT Pub. No.: WO2015/009930
PCT Pub. Date: Jan. 22, 2015

(65) Prior Publication Data
US 2016/0152612 A1    Jun. 2, 2016

Related U.S. Application Data

(60) Provisional application No. 61/847,280, filed on Jul. 17, 2013.

(51) Int. Cl.
*C07D 471/04* (2006.01)
*C07D 471/14* (2006.01)

(52) U.S. Cl.
CPC ......... *C07D 471/04* (2013.01); *C07D 471/14* (2013.01)

(58) Field of Classification Search
None
See application file for complete search history.

(56) References Cited

U.S. PATENT DOCUMENTS

| | | |
|---|---|---|
| 3,674,790 A | 7/1972 | Wolf et al. |
| 4,742,061 A | 5/1988 | Martin et al. |
| 4,816,464 A | 3/1989 | Gilman et al. |
| 4,843,079 A | 6/1989 | Shutske et al. |
| 5,250,534 A | 10/1993 | Bell et al. |
| 5,294,612 A | 3/1994 | Bacon et al. |
| 5,346,901 A | 9/1994 | Bell et al. |
| 5,565,325 A | 10/1996 | Blake |
| 5,712,171 A | 1/1998 | Zambias et al. |
| 5,859,006 A | 1/1999 | Daugan |
| 6,008,226 A | 12/1999 | Kumar et al. |
| 6,294,547 B1 | 9/2001 | Oka et al. |
| 6,362,178 B1 | 3/2002 | Niewohner et al. |
| 6,384,047 B1 | 5/2002 | Flockerzi et al. |
| 6,436,952 B1 | 8/2002 | Flockerzi |
| 7,378,430 B2 | 5/2008 | Bi et al. |
| 10,626,113 B2 * | 4/2020 | Landry ............... C07D 471/04 |
| 2002/0133008 A1 | 9/2002 | Macor et al. |
| 2003/0199693 A1 | 10/2003 | Chen |
| 2005/0009163 A1 | 1/2005 | Tong et al. |

FOREIGN PATENT DOCUMENTS

| | | |
|---|---|---|
| WO | WO-93/07124 | 4/1993 |
| WO | WO-95/18972 | 7/1995 |
| WO | WO-95/19978 | 7/1995 |
| WO | WO-98/49166 | 11/1998 |
| WO | WO-1998/055481 A1 | 12/1998 |
| WO | WO-99/07409 | 2/1999 |
| WO | WO-99/24433 | 5/1999 |
| WO | WO-99/32619 | 7/1999 |
| WO | WO-99/54333 | 10/1999 |
| WO | WO-01/27112 | 4/2001 |

(Continued)

OTHER PUBLICATIONS

Silverman. The Organic Chemistry of Drug Design and Drug Action. Section 2, p. 29-32, 2004. (Year: 2004).*
AbdulHameed, M. D. M. et al., "Microscopic modes and free energies of 3-phosphoinositide-dependent kinase-1 (PDK1) binding with celecoxib and other inhibitors," The Journal of Physical Chemistry, vol. 110, No. 51, pp. 26365-26374 (2006).
Ajay, "Predicting Drug-Likeness: Why and How?," Current Topics in Medicinal Chemistry, vol. 2, No. 12, pp. 1273-1286 (Dec. 2002).
Alamed, J. et al., "Two-day radial-arm water maze learning and memory task; robust resolution of amyloid-related memory deficits in transgenic mice," Nature Protocols, vol. 1, No. 4, pp. 1671-1679 (2006).
Andreasen, N. et al., "CSF markers for Alzheimer's disease: total tau, phospho-tau and Abeta42," World J. Biol. Psychiatry, vol. 4, No. 4, pp. 147-155 (2003).
Arancio, O. et al., "Activity-dependent long-term enhancement of transmitter release by presynaptic 3',5'-cyclic GMP in cultured hippocampal neurons," Nature, vol. 376, No. 6535, pp. 74-80 (Jul. 6, 1995).

(Continued)

Primary Examiner — Leslie A. Royds Draper
(74) Attorney, Agent, or Firm — Wilmer Cutler Pickering Hale and Dorr LLP

(57) ABSTRACT

The invention provides for novel benzonaphthyridine derivatives and compositions comprising novel benzonaphthyridine derivatives. In some embodiments, the compounds are phosphodiesterase inhibitors. The invention further provides for methods for inhibition of phosphodiesterase comprising contacting phosphodiesterase with novel benzonaphthyridine derivatives or compositions comprising novel benzonaphthyridine derivatives. The invention further provides for methods for treatment of neurodegenerative diseases, increasing memory or long term potentiation with novel benzonaphthyridine derivatives or compositions comprising novel benzonaphthyridine derivatives. In some embodiments, the phosphodiesterase is PDE5.

26 Claims, 9 Drawing Sheets

(56) References Cited

FOREIGN PATENT DOCUMENTS

| WO | WO-01/27113 | 4/2001 |
|---|---|---|
| WO | WO-2005/083069 | 9/2005 |
| WO | WO-2006/094237 | 9/2006 |
| WO | WO-2008/095835 | 8/2008 |
| WO | WO-2009/050554 | 4/2009 |
| WO | WO-2009/124119 | 10/2009 |
| WO | WO-2010/015589 | 2/2010 |
| WO | WO-2011/015523 | 2/2011 |
| WO | WO-2013/109738 | 7/2013 |

OTHER PUBLICATIONS

Arancio, O. et al., "RAGE potentiates Abeta-induced perturbation of neuronal function in transgenic mice," The EMBO Journal, vol. 23, No. 20, pp. 4096-4105 (2004).
Arendash, G. W. et al., "Progressive, age-related behavioral impairments in transgenic mice carrying both mutant amyloid precursor protein and presenilin-1 transgenes," Brain Research, vol. 891, No. 1-2, pp. 42-53 (2001).
Bach, M. E. et al., "Age-related defects in spatial memory are correlated with defects in the late phase of hippocampal long-term potentiation in vitro and are attenuated by drugs that enhance the cAMP signaling pathway," Proc. Natl. Acad. Sci. USA, vol. 96, No. 9, pp. 5280-5285 (Apr. 1999).
Bajorath, Jurgen, "Integration of virtual and high-throughput screening," Nat. Rev. Drug Discov., vol. 1, No. 11, pp. 882-894 (Nov. 2002).
Baltrons, M. A. et al., "Beta-amyloid peptides decrease soluble guanylyl cyclase expression in astroglial cells," Neurobiology of Disease, vol. 10, No. 2, pp. 139-149 (2002).
Baltrons, M. A. et al., "Regulation of NO-dependent cyclic GMP formation by inflammatory agents in neural cells," Toxicology Letters, vol. 139, No. 2-3, pp. 191-198 (2003).
Barad, M. et al., "Rolipram, a type IV-specific phosphodiesterase inhibitor, facilitates the establishment of long-lasting long-term potentiation and improves memory," Proc. Natl. Acad. Sci. USA, vol. 95, No. 25, pp. 105020-105025 (Dec. 1998).
Baratti, C. M. and Boccia, M. M., "Effects of sildenafil on long-term retention of an inhibitory avoidance response in mice," Behavioural Pharmacology, vol. 10, No. 8, pp. 731-737 (1999).
Barrios Sosa, A. C. et al., "Synthesis and inhibition of Src kinase activity by 7-ethenyl and 7-ethynyl-4-anilino-3-quinolinecarbonitriles," Bioorganic & Medicinal Chemistry Letters, vol. 14, No. 9, pp. 2155-2158 (2004).
Bass, Brenda L., "The short answer," Nature, vol. 411, pp. 428-429 (May 24, 2001).
Basun, H. et al., "Plasma levels of Abeta42 and Abeta40 in Alzheimer patients during treatment with the acetylcholinesterase inhibitor tacrine," Dementia and Geriatric Cognitive Disorders, vol. 14, No. 3, pp. 156-160 (May 7, 2002).
Battaglioli, E. et al., "REST repression of neuronal genes requires components of the hSWI-SNF complex," The Journal of Biological Chemistry, vol. 277, No. 43, pp. 41038-41045 (Oct. 26, 2002).
Bennett, B. M. et al., "Cognitive deficits in rats after forebrain cholinergic depletion are reversed by a novel NO mimetic nitrate ester," Neuropsychopharmacology, vol. 32, pp. 505-513 (2007).
Billings, L. M. et al., "Intraneuronal Abeta causes the onset of early Alzheimer's disease-related cognitive deficits in transgenic mice," Neuron, vol. 45, No. 5, pp. 675-688 (Mar. 3, 2005).
Blaney, J. M. and Martin, E. J., "Computational approaches for combinatorial library design and molecular diversity analysis," Current Opinion in Chemical Biology, vol. 1, No. 1, pp. 54-59 (1997).
Bliss, T. V. P. and Collingridge, G. L., "A synaptic model of memory: long-term potentiation in the hippocampus," Nature, vol. 361, No. 6407, pp. 31-39 (Jan. 7, 1993).

Blondelle, S. E. and Houghten, R. A., "Novel antimicrobial compounds identified using synthetic combinatorial library technology," TIBTECH, vol. 14, pp. 60-65 (Feb. 1996).
Bohm, Hans-Joachim, "LUDI: rule-based automatic design of new substituents for enzyme inhibitor leads,". Journal of Compuer-Aided Molecular Designs, vol. 6, No. 6, pp. 593-606, 15 pages (1992).
Bohm, Hans-Joachim, "On the use of LUDI to search the Fine Chemicals Directory for ligands of proteins of known three-dimensional structure," Journal of Computer-Aided Molecular Designs, vol. 8, No. 5, pp. 623-632, 11 pages (1994).
Bohm, Hans-Joachim, "The computer program LUDI: a new method for the de novo design of enzyme inhibitors," Journal of Computer-Aided Molecular Design, vol. 6, No. 1, pp. 61-78, 19 pages (1992).
Bon, C. L. M. and Garthwaite, J., "On the role of nitric oxide in hippocampal long-term potentiation," The Journal of Neuroscience, vol. 23, No. 5, pp. 1941-1948 (Mar. 1, 2003).
Bonkale, W. L. et al., "Reduced nitric oxide responsive soluble guanylyl cyclase activity in the superior temporal cortex of patients with Alzheimer's disease," Neuroscience Letters, vol. 187, pp. 5-8 (1995).
Borchelt, D. R. et al., "Accelerated amyloid deposition in the brains of transgenic mice coexpressing mutant presenilin 1 and amyloid precursor proteins," Neuron, vol. 19, No. 4, pp. 939-945 (Oct. 1997).
Boschelli, D. H. et al., "Synthesis and Src Kinase Inhibitory Activity of a Series of 4-Phenylamino-3-quinolinecarbonitriles," J. Med. Chem., vol. 44, No. 5, pp. 822-833 (2001).
Bourtchuladze, R. et al., "Deficient long-term memory in mice with a targeted mutation of the cAMP-responsive element-binding protein," Cell, vol. 79, No. 1, pp. 59-68 (Oct. 7, 1994).
Brenner, S. and Lerner, R. A., "Encoded combinatorial chemistry," Proc. Natl. Acad. Sci. USA, vol. 89, pp. 5381-5383 (Jun. 1992).
Bunin, B. A. et al., "The combinatorial synthesis and chemical and biological evaluation of a 1,4-benzodiazepine library," Proc. Natl. Acad. Sci. USA, vol. 91, pp. 4708-4712 (May 1994).
Burnett, A. L., et al., "Long-term oral phosphodiesterase 5 inhibitor therapy alleviates recurrent priapism," Adult Urology, vol. 67, No. 5, pp. 1043-1048 (2006).
Caccia, S. et al., "Disposition and metabolism of minaprine in the rat," Xenobiotica, vol. 15, No. 12, pp. 1111-1119 (1985).
Card, G. L. et al., "Structural basis for the activity of drugs that inhibit phosphodiesterases," Structure, vol. 12, No. 12, pp. 2233-2247 (Dec. 2004).
Case, D. A. et al., "The Amber biomolecular simulation programs," J. Comput. Chem., vol. 26, No. 16, pp. 1668-1688 (Dec. 2005).
Champion, H. C. et al., "Phosphodiesterase-5A dysregulation in penile erectile tissue is a mechanism of priapism," Proc. Natl. Acad. Sci. USA, vol. 102, No. 5, pp. 1661-1666 (Feb. 1, 2005).
Chang, E. H. et al., "AMPA receptor downscaling at the onset of Alzheimer's disease pathology in double knockin mice," Proceedings of the National Academy of Sciences of the United States of America, vol. 103, No. 9, pp. 3410-3415 (Feb. 26, 2006).
Chapman, P. F. et al., "Impaired synaptic plasticity and learning in aged amyloid precursor protein transgenic mice," Nat. Neurosci., vol. 2, No. 3, pp. 271-276 (Mar. 1999).
Chen, X. and C.-G. Zhan, "Fundamental reaction pathways and free energy barriers for ester hydrolysis of intracellular second messenger 3',5'-cyclic nucleotide," J. Phys. Chem. B, vol. 108, pp. 3789-3797 (2004).
Chen, X. and C.-G. Zhan, "Theoretical determination of activation free energies for alkaline hydrolysis of cyclic and acyclic phosphodiesters in aqueous solution," J. Phys. Chem. B, vol. 108, pp. 6407-6413, 9 pages (2004).
Chen, X. and W. Wang, "The Use of Bioisosteric Groups in Hit Optimization," Ann. Reports Med. Chem., vol. 38, pp. 333-346 (2003).
Choi, S. et al., "Efficacy of vardenafil and sildenafil in facilitating penile erection in an animal model," J. Androl., vol. 23, No. 3, pp. 332-337 (May/Jun. 2002).
Christian, R. B. et al., "Simplified Methods for Construction, Assessment and Rapid Screening of Peptide Libraries in Bacteriophage," J. Mol. Biol., vol. 227, pp. 711-718 (1992).

(56) References Cited

OTHER PUBLICATIONS

Colton, C. A. et al., "NO synthase 2 (NOS2) deletion promotes multiple pathologies in a mouse model of Alzheimer's disease," Proc. Natl. Acad. Sci. USA, vol. 103, No. 34, pp. 12867-12872 (Aug. 22, 2006).
Contestabile, A. et al., "Brain nitric oxide and its dual role in neurodegeneration/neuroprotection: understanding molecular mechanisms to devise drug approaches," Curr. Med. Chem., vol. 10, No. 20, pp. 2147-2174 (2003).
Corbin, J. D. and Francis, S. H., "Pharmacology of phosphodiesterase-5 inhibitors," Int. J. Clin. Pract., vol. 56, No. 6, pp. 453-459, 8 pages (Jul./Aug. 2002).
Cornell, W. D. et al., "A second generation force field for the simulation of proteins, nucleic acids, and organic molecules," J. Am. Chem. Soc., vol. 117, pp. 5179-5197, 21 pages (1995).
Coste, H. and Grondin, P., "Characterization of a novel potent and specific inhibitor of type V phosphodiesterase," Biochem. Pharmacol., vol. 50, No. 10, pp. 1577-1585 (1995).
Cullen, W. K. et al., "Block of LTP in rat hippocampus in vivo by beta-amyloid precursor protein fragments," NeuroReport, vol. 8, No. 15, pp. 3213-3217 (Sep. 24, 1997).
Dahiyat, B. I. and Mayo, S. L., "De Novo Protein Design: Fully Automated Sequence Selection," Science, vol. 278, pp. 82-87 (Oct. 3, 1997).
Dallas, A. and Vlassov, A. V., "RNAi: A novel antisense technology and its therapeutic potential," Med. Sci. Monit., vol. 12, No. 4, pp. RA67-RA74 (2006).
Daugan, A. et al., "The discovery of tadalafil: a novel and highly selective PDE5 inhibitor. 1: 5,6,11,11a-tetrahydro-1H-imidazo[1',5':1,6]pyrido[3,4-b]indole-1,3(2H)-dio ne analogues," J. Med. Chem., vol. 46, No. 21, pp. 4525-4532 (2003).
Daugan, A. et al., "The discovery of tadalafil: a novel and highly selective PDE5 inhibitor. 2:2,3,6,7,12,12a-hexahydropyrazino[1',2':1,6]pyrido[3,4-b]indole-1,4-dione analogues," J. Med. Chem., vol. 46, No. 21, pp. 4533-4542 (2003).
Davis, R. L. et al., "The cyclic AMP system and *Drosophila* learning," Mol. Cell Biochem., vol. 149-150, pp. 271-278 (1995).
Davis, Ronald L., "Physiology and biochemistry of *Drosophila* learning mutants," Physiol. Rev., vol. 76, No. 2, pp. 299-317 (Apr. 1996).
Degerman, E. et al., "Structure, localization, and regulation of cGMP-inhibited phosphodiesterase (PDE3)," J. Biol. Chem., vol. 272, No. 11, pp. 6823-6826 (Mar. 14, 1997).
Devlin, J. J. et al., "Random Peptide Libraries: A Source of Specific Protein Binding Molecules," Science, vol. 249, pp. 404-406 (Jul. 27, 1990).
Di Rosa, G. et al., "Calpain inhibitors: a treatment for Alzheimer's disease," J. Mol. Neurosci., vol. 19, No. 1-2, pp. 135-141 (2002).
Diamond, D. M. et al., "Exposing rats to a predator impairs spatial working memory in the radial arm water maze," Hippocampus, vol. 9, pp. 542-552 (1999).
Dineley, K. T. et al., "Accelerated plaque accumulation, associative learning deficits, and up-regulation of alpha 7 nicotinic receptor protein in transgenic mice co-expressing mutant human presenilin 1 and amyloid precursor proteins," J. Biol. Chem., vol. 277, No. 25, pp. 22768-22780 (Jun. 21, 2002).
Dineley, K. T. et al., "Beta-amyloid activates the mitogen-activated protein kinase cascade via hippocampal alpha7 nicotinic acetylcholine receptors: In vitro and in vivo mechanisms related to Alzheimer's disease," J. Neurosci., vol. 21, No. 12, pp. 4125-4133 (Jun. 15, 2001).
Dixon, D. A. et al., "Decomposition pathways of peroxynitrous acid: Gas-phase and solution energetics," J. Phys. Chem. A, vol. 106, pp. 3191-3196 (2002).
Dixon, D. A. et al., "The gas and solution phases acidities of HNO, HOONO, HONO, and $HONO_2$," Int. J. Mass Spectrom., vol. 227, pp. 421-438 (2003).
Duff, K. et al., "Increased amyloid-beta42(43) in brains of mice expressing mutant presenilin 1," Nature, vol. 383, No. 6602, pp. 710-713 (Oct. 24, 1996).

Elbashir, S. M. et al., "Duplexes of 21-nucleotide RNAs mediate RNA interference in cultured mammalian cells," Nature, vol. 411, pp. 494-498 (May 24, 2001).
Erb, E. et al., "Recursive deconvolution of combinatorial chemical libraries," Proc. Natl. Acad. Sci. USA, vol. 91, pp. 11422-11426 (Nov. 1994).
Evans, D. C. et al., "Drug-Protein Adducts: An Industry Perspective on Minimizing the Potential for Drug Bioactivation in Drug Discovery and Development," Chem. Res. Toxicol., vol. 17, pp. 3-16, 16 pages (2004).
Ewing, T. J. et al., "DOCK 4.0: search strategies for automated molecular docking of flexible molecule databases," J. Comput. Aided Mol. Des., vol. 15, No. 5, pp. 411-428 (2001).
Fadrna, E. et al., "Molecular dynamics simulations of Guanine quadruplex loops: advances and force field limitations," Biophys. J., vol. 87, No. 1, pp. 227-242 (Jul. 2004).
Fitzjohn, S. M. et al., "Age-related impairment of synaptic transmission but normal long-term potentiation in transgenic mice that overexpress the human APP695SWE mutant form of amyloid precursor protein," J. Neurosci., vol. 21, No. 13, pp. 4691-4698 (Jul. 1, 2001).
Fodor, S. P. A. et al., "Light-Directed, Spatially Addressable Parallel Chemical Synthesis," Science, vol. 251, pp. 767-773 (Feb. 15, 1991).
Food and Drug Administration, "Viagra tablets (sildenafil citrate): Review and evaluation of pharmacology and toxicology data," Report from the Division of Cardio-Renal Drug Products (HFD-110), Center for Drug Evaluation and Research, NDA#20-895, pp. 1-25 (Jan. 26, 1998).
Francis, Y. I. et al., "Beneficial effect of the histone deacetylase inhibitor TSA in a mouse model of Alzheimer's disease," Soc. Neurosci. Abstr., vol. 548.5, 1 page (Nov. 6, 2007).
Freir, D. B. et al., "Blockade of long-term potentiation by beta-amyloid peptides in the CA1 region of the rat hippocampus in vivo," J. Neurophysiol., vol. 85, No. 2, pp. 708-713 (2001).
Gallop, M. A. et al., "Applications of Combinatorial Technologies to Drug Discovery," J. Medicinal Chemistry, vol. 37, No. 9, pp. 1233-1251 (Apr. 29, 1994).
Gao, D. et al., "Computational design of a human butyrylcholinesterase mutant for accelerating cocaine hydrolysis based on the transition-state simulation," Angew Chem. Int. Ed. Engl., vol. 45, No. 4, pp. 653-657 (Jan. 16, 2006).
Gentile, M. T. et al., "Mechanisms of soluble beta-amyloid impairment of endothelial function," J. Biol. Chem., vol. 279, No. 46, pp. 48135-48142 (Nov. 12, 2004).
Gillet, V. et al., "SPROUT: a program for structure generation," J. Comput. Aided Mol. Des., vol. 7, No. 2, pp. 127-153, 28 pages (Apr. 1993).
Gillet, V. J. et al., "SPROUT: recent developments in the de novo design of molecules," J. Chem. Inf. Comput. Sci., vol. 34, No. 1, pp. 207-217 (1994).
Gong, B. et al., "Persistent improvement in synaptic and cognitive functions in an Alzheimer mouse model following rolipram treatment," J. Clin. Invest., vol. 114, pp. 1624-1634 (Dec. 2004).
Gong, B. et al., "Ubiquitin Hydrolase Uch-L1 Rescues beta-Amyloid-Induced Decreases in Synaptic Function and Contextual Memory," Cell, vol. 126, pp. 775-788 (Aug. 25, 2006).
Gresser, U. and Gleiter, C. H., "Erectile dysfunction: comparison of efficacy and side effects of the PDE-5 inhibitors sildenafil, vardenafil and tadalafil—review of the literature," Eur. J. Med. Res., vol. 7, No. 10, pp. 435-446 (2002).
Haas, J. et al., "Inducible nitric oxide synthase and argininosuccinate synthetase: co-induction in brain tissue of patients with Alzheimer's dementia and following stimulation with beta-amyloid 1-42 in vitro," Neurosci. Lett., vol. 322, No. 2, pp. 121-125 (2002).
Hamza, A. and Zhan, C. G., "How can (−)-epigallocatechin gallate from green tea prevent HIV-1 infection? Mechanistic insights from computational modeling and the implication for rational design of anti-HIV-1 entry inhibitors," J. Phys. Chem. B, vol. 110, No. 6, pp. 2910-2917 (2006).
Hamza, A. et al., "Understanding human 15-hydroxyprostaglandin dehydrogenase binding with NAD+ and PGE2 by homology mod-

(56) References Cited

OTHER PUBLICATIONS eling, docking and molecular dynamics simulation," Bioorg. Med. Chem., vol. 13, No. 14, pp. 4544-4551 (2005).
Hamza, A., et al., Molecular dynamics simulation of cocaine binding with human butyrylcholinesterase and its mutants. J Phys Chem B Condens Matter Mater Surf Interfaces Biophys, 2005. 109(10): p. 4776-82.
Hansen, John B., "Towards Selective Kir6.2/SUR1 Potassium Channel Openers, Medicinal Chemistry and Therapeutic Perspectives," Curr. Med. Chem., vol. 13, No. 4, pp. 361-376 (2006).
Harris, D. L. et al., "Theoretical study of the ligand-CYP2B4 complexes: effect of structure on binding free energies and heme spin state," Proteins, vol. 55, No. 4, pp. 895-914 (2004).
Herman, S. B. et al., "Analysis of a mutation in phosphodiesterase type 4 that alters both inhibitor activity and nucleotide selectivity," Mol. Pharmacol., vol. 57, No. 5, pp. 991-999 (2000).
Ho, C. M. W. and Marshall, G. R., "Foundation: a program to retrieve all possible structures containing a user-defined minimum number of matching query elements from three-dimensional databases," J. Comput. Aided Mol. Des., vol. 7, No. 1, pp. 3-22 (1993).
Hodgson, John, "ADMET—turning chemicals into drugs," Nat. Biotechnol., vol. 19, No. 8, pp. 722-726 (Aug. 2001).
Houghten, R. A. et al., "Generation and use of synthetic peptid combinatorial libraries for basic research and drug discovery," Nature, vol. 354, No. 6348, pp. 84-86 (Nov. 7, 1991).
Houghten, R. A. et al., "The Use of Synthetic Peptide Cominatorial Libraries for the Identifiation of Bioactive Peptides," Biotechniques, vol. 13, No. 3, pp. 412-421 (Sep. 1992).
Hsia, A. Y. et al., "Plaque-independent disruption of neural circuits in Alzheimer's disease mouse models," Proc. Natl. Acad. Sci. USA, vol. 96, No. 6, pp. 3228-3233 (Mar. 1999).
Hsiao, K. et al., "Correlative memory deficits, Abeta elevation, and amyloid plaques in transgenic mice,"Science, vol. 274, No. 5284, pp. 99-102, 6 pages (Oct. 4, 1996).
Hsieh, H. et al., "AMPA-R removal underlies Abeta-induced synaptic depression and dendritic spine loss," Neuron, vol. 52, No. 5, pp. 831-843 (Dec. 7, 2006).
Huai, Q. et al., "Crystal structure of phosphodiesterase 9 shows orientation variation of inhibitor 3-isobutyl-1-methylxanthine binding," Proc. Natl. Acad. Sci. USA, vol. 101, No. 26, pp. 9624-9629 (Jun. 29, 2004).
Huai, Q. et al., "Crystal structures of phosphodiesterases 4 and 5 in complex with inhibitor 3-isobutyl-1-methylxanthine suggest a conformation determinant of inhibitor selectivity," J. Biol. Chem., vol. 279, No. 13, pp. 13095-13101 (Mar. 26, 2004).
Huai, Q. et al., "The crystal structure of AMP-bound PDE4 suggests a mechanism for phosphodiesterase catalysis," Biochemistry, vol. 42, No. 45, pp. 13220-13226, 9 pages (Nov. 18, 2003).
Huang, X. et al., "Structural and functional characterization of human microsomal prostaglandin E synthase-1 by computational modeling and site-directed mutagenesis," Bioorg. Med. Chem., vol. 14, No. 10, pp. 3553-3562 (2006).
Hudson, Peter J., "Recombinant antibody fragments," Curr. Opin. Biotechnol., vol. 9, pp. 395-402 (1998).
International Search Report and Written Opinion issued by the U. S. Patent and Trademark Office as International Searching Authority for International Application No. PCT/US2013/021918 dated Mar. 19, 2013 (8 pages).
Irwin, J. J. and Shoichet, B. K., "ZINC—a free database of commercially available compounds for virtual screening," J. Chem. Inf. Model, vol. 45, No. 1, pp. 177-182 (2005).
Itoh, A. et al., "Impairments of long-term potentiation in hippocampal slices of beta-amyloid-infused rats," Eur. J. Pharmacol., vol. 382, No. 3, pp. 167-175 (1999).
Zhang, X. et al., "Efficacy and selectivity of phosphodiesterase-targeted drugs in inhibiting photoreceptor phosphodiesterase (PDE6) in retinal photoreceptors," Invest. Ophthalmol. Vis. Sci., vol. 46, No. 9, pp. 3060-3066 (Sep. 2005).
Jantzen, P. T. et al., "Microglial activation and beta-amyloid deposit reduction caused by a nitric oxide-releasing nonsteroidal anti-inflammatory drug in amyloid precursor protein plus presenilin-1 transgenic mice," J. Neurosci., vol. 22, No. 6, pp. 2246-2254 (Mar. 15, 2002).
Janus, C. et al., "A beta peptide immunization reduces behavioural impairment and plaques in a model of Alzheimer's disease," Nature, vol. 408, No. 6815, pp. 979-982, 6 pages (Dec. 21/28, 2000).
Jayawickreme, C. K. et al., "Creation and functional screening of a multi-use pepide library," Proc. Nat'l. Acad. Sci. USA, vol. 91, pp. 1614-1618 (Mar. 1994).
Jolas, T. et al., "Long-term potentiation is increased in the CA1 area of the hippocampus of APP(swe/ind) CRND8 mice," Neurobiol. Dis., vol. 11, No. 3, pp. 394-409 (2002).
Kalaria, Raj N., "Vascular factors in Alzheimer's disease," Int. Psychogeriatr., vol. 15, Suppl. 1, pp. 47-52 (2003).
Kalota, A. et al., "Progress in the Development of Nucleic Acid Therapeutics," Handb. Exp. Pharmacol., vol. 173, pp. 173-196 (2006).
Kalé, L. et al., "NAMD2: greater scalability for parallel molecular dynamics," Journal of Computation Physics, vol. 151, pp. 283-312 (1999).
Kamenetz, F. et al., "APP processing and synaptic function," Neuron, vol. 37, pp. 925-937 (Mar. 27, 2003).
Kay, B. K. et al., "An M13 phage library displaying random 38-amino-acid peptides as a source of novel sequences with affinity to selected targets," Gene, vol. 128, pp. 59-65 (1993).
Kemenes, I. et al., "Critical time-window for NO-cGMP-dependent long-term memory formation after one-trial appetitive conditioning," J. Neurosci., vol. 22, No. 4, pp. 1414-1425 (Feb. 15, 2002).
Khalil, Z. et al., "Mechanisms of peripheral microvascular dysfunction in transgenic mice overexpressing the Alzheimer's disease amyloid Abeta protein," J. Alzheimers Dis., vol. 4, No. 6, pp. 467-478 (2002).
Kim, J. H. et al., "Use-dependent effects of amyloidogenic fragments of (beta)-amyloid precursor protein on synaptic plasticity in rat hippocampus in vivo," J. Neurosci., vol. 21, No. 4, pp. 1327-1333 (Feb. 15, 2001).
Kloner, R. A. et al., "Cardiovascular safety update of Tadalafil: retrospective analysis of data from placebo-controlled and open-label clinical trials of Tadalafil with as needed, three times-per-week or once-a-day dosing," Am. J. Cardiol., vol. 97, No. 12, pp. 1778-1784 (2006).
Koča, J. et al., "Mobility of the active site bound paraoxon and sarin in zinc-phosphotriesterase by molecular dynamics simulation and quantum chemical calculation," J. Am. Chem. Soc., vol. 123, No. 5, pp. 817-826 (2001).
Koglin, M. et al., "BAY 41-2272 activates two isoforms of nitric oxide-sensitive guanylyl cyclase," Biochem. Biophys. Res. Commun., vol. 292, No. 4, pp. 1057-1062 (2002).
Kowalska, M. A. and Badellino, K., "Beta-Amyloid protein induces platelet aggregation and supports platelet adhesion," Biochem. Biophys. Res. Commun., vol. 205, No. 3, pp. 1829-1835 (Dec. 30, 1994).
Kubinyi, Hugo, "Drug research: myths, hype and reality," Nat. Rev. Drug Discov., vol. 2, No. 8, pp. 665-668 (Aug. 2003).
Lam, K. S. et al., "A new type of synthetic peptide library for identifying ligand-binding activity," Nature, vol. 354, pp. 82-84 (Nov. 7, 1991).
Larson, J. et al., "Alterations in synaptic transmission and long-term potentiation in hippocampal slices from young and aged PDAPP mice," Brain Research, vol. 840, No. 1-2, pp. 23-35 (1999).
Lawrence, M. C. and Davis, P. C., "CLIX: a search algorithm for finding novel ligands capable of binding proteins of known three-dimensional structure," Proteins, vol. 12, No. 1, pp. 31-41 (1992).
Lee, D. and O'Dowd, D. K., "cAMP-dependent plasticity at excitatory cholinergic synapses in *Drosophila* neurons: alterations in the memory mutant dunce," J. Neurosci., vol. 20, No. 6, pp. 2104-2111 (Mar. 15, 2000).
Lee, M. E. et al., "Crystal structure of phosphodiesterase 4D and inhibitor complex[1]," FEBS Lett., vol. 530, No. 1-3, pp. 53-58 (2002).
Lenstra, J. A. et al., "Isolation of sequences from a random-sequence expression library that mimic viral epitopes," J. Immunol. Meth., vol. 152, pp. 149-157 (1992).

(56) References Cited

OTHER PUBLICATIONS

Lipinski, C. A. et al., "Experimental and Computational Approaches to Estimate Solubility and Permeability in Drug Discovery and Development Settings," Adv. Drug Deliv. Rev., vol. 46, pp. 3-26 (2001).
Lipinski, Christopher A., "Drug-like properties and the causes of poor solubility and poor permeability," J. Pharmacol. Toxicol. Methods, vol. 44, No. 1, pp. 235-249 (2000).
Liu, L. et al., "Abeta levels in serum, CSF and brain, and cognitive deficits in APP+PS1 transgenic mice," Neuroreport, vol. 14, No. 1, pp. 163-166 (Jan. 20, 2003).
Liu, S. et al., "alpha-Synuclein produces a long-lasting increase in neurotransmitter release," Embo J., vol. 23, No. 22, pp. 4506-4516 (2004).
Liu, S. et al., "Dissecting the cofactor-dependent and independent bindings of PDE4 inhibitors," Biochemistry, vol. 40, No. 34, pp. 10179-10186 (Aug. 28, 2001).
Lu, Y. F. et al., "Nitric oxide signaling contributes to late-phase LTP and CREB phosphorylation in the hippocampus," J. Neurosci., vol. 19, No. 23, pp. 10250-10261 (Dec. 1, 1999).
Lunyak, V. V. et al., "Corepressor-dependent silencing of chromosomal regions encoding neuronal genes," Science, vol. 298, No. 5599, pp. 1747-1752 (Nov. 29, 2002).
Lustbader, J. W. et al., "ABAD directly links Abeta to mitochondrial toxicity in Alzheimer's disease," Science, vol. 304, No. 5669), pp. 448-452 (Apr. 16, 2004).
Lutzelburger, M. and Kjems, J., "Strategies to Identify Potential Therapeutic Target Sites in RNA," Handbook of Experimental Pharmacology, vol. 173, pp. 243-259, (2006).
Mannhold, Raimund, "Structure-Activity Relationships of $K_{ATP}$ Channel Openers," Current Topics in Medicinal Chemistry, vol. 6, No. 10, pp. 1031-1047 (2006).
Martin, E. J. et al., "Measuring diversity: experimental design of combinatorial libraries for drug discovery," J. Med. Chem., vol. 38, No. 9, pp. 1431-1436 (1995).
Martin, Yvonne C., "A bioavailability score," J. Med. Chem., vol. 48, No. 9, pp. 3164-3170 (2005).
Masliah, E., "Mechanisms of synaptic dysfunction in Alzheimer's disease," Histol. Histopathol., vol. 10, No. 2, pp. 509-519 (1995).
Mattheakis, L. C. et al., "An in vitro polysome display system for identifying ligands from very large peptide libraries," Proc. Natl. Acad. Sci. USA, vol. 91, pp. 9022-9026 (Sep. 1994).
Mattson, M. P. et al., "Secreted form of amyloid precursor protein enhances basal glucose and glutamate transport and protects against oxidative impairment of glucose and glutamate transport in synaptosomes by a cyclic GMP-mediated mechanism," J. Neurochem., vol. 73, No. 2, pp. 532-537 (1999).
Mattson, Mark P., "Cellular actions of beta-amyloid precursor protein and its soluble and fibrillogenic derivatives," Physiol. Rev. vol. 77, No. 4, pp. 1081-1132 (Oct. 1997).
Maynard, J. and Georgiou, G., "Antibody Engineering," Annu. Rev. Biomed. Eng., vol. 2, pp. 339-376 (2000).
McCann, S. M., "The nitric oxide hypothesis of brain aging," Exp. Gerontol., vol. 32, No. 4-5, pp. 431-440 (1997).
McCarty, M.F., "Vascular nitric oxide may lessen Alzheimer's risk," Med. Hypotheses, vol. 51, No. 6, pp. 465-476 (1998).
McConnell, H. M. et al., "The Cytosensor Microphysiometer: Biological Applications of Silicon Technology," Science, vol. 257, pp. 1906-1912 (Sep. 25, 1992).
Medynski, Dan, "Synthetic Peptide Combinatorial Libraries," BioTechnology, vol. 12, pp. 709-710 (1994).
Moechars, D. et al., "Early phenotypic changes in transgenic mice that overexpress different mutants of amyloid precursor protein in brain," J. Biol. Chem., vol. 274, No. 10, pp. 6483-6492 (1999).
Monsonego, A. et al., "Microglia-mediated nitric oxide cytotoxicity of T cells following amyloid beta-peptide presentation to Th1 cells," J. Immunol., vol. 171, No. 5, pp. 2216-2224 (2003).
Moreno, H. W. et al., "Adapting fMRI so that normal and abnormal hippocampal circuits can be investigated in transgenic mice," Soc. Neurosci. Abstr., Presentation 693.6, 2 pages (Oct. 26, 2004).
Moreno, H. W. et al., "Imaging Hippocampal Dysfunction in Transgenic Mice with MRI," The 9th International Conference on Alzheimer's Disease and Related Disorders Abstr., 1 page (2004).
Morgan, D. et al., "A beta peptide vaccination prevents memory loss in an animal model of Alzheimer's disease," Nature, vol. 408, No. 6815, pp. 982-985 (Dec. 21/28, 2000).
Mosbach, Klaus, "Molecular imprinting," Trends in Biochem. Sci., vol. 19, pp. 9-14 (Jan. 1994).
Murthy, K. S. et al., "PKA-dependent activation of PDE3A and PDE4 and inhibition of adenylyl cyclase V/VI in smooth muscle," Am. J. Physiol. Cell Physiol., vol. 282, No. 3, pp. C508-C517 (Mar. 2002).
Nakagami, Y. et al., "A novel beta-sheet breaker, RS-0406, reverses amyloid beta-induced cytotoxicity and impairment of long-term potentiation in vitro," Br. J. Pharmacol., vol. 137, No. 5, pp. 676-682 (2002).
Nalbantoglu, J. et al., "Impaired learning and LTP in mice expressing the carboxy terminus of the Alzheimer amyloid precursor protein," Nature, vol. 387, No. 6632, pp. 500-505 (May 29, 1997).
Nehlig, A. et al., "Caffeine and the central nervous system: mechanisms of action, biochemical, metabolic and psychostimulant effects," Brain Res. Rev., vol. 17, pp. 139-169 (1992).
Nicholson, C. D., "Pharmacology of nootropics and metabolically active compounds in relation to their use in dementia," Psychopharmacology (Berl), vol. 101, pp. 147-159 (1990).
Ninan, I. and Arancio, O., "Presynaptic CaMKII Is Necessary for Synaptic Plasticity in Cultured Hippocampal Neurons," Neuron, vol. 42, No. 1, pp. 129-141 (Apr. 8, 2004).
No Author Listed, "What is ADMET Predictor?," retrieved from the internet from URL: [http://www.simulations-plus.com/Products.aspx?grpID=1&cID=10&pID=13], 3 pages (retreived on Mar. 26, 2015).
Oddo, S. et al., "Triple-transgenic model of Alzheimer's disease with plaques and tangles: intracellular Abeta and synaptic dysfunction," Neuron, vol. 39, No. 3, pp. 409-421 (Jul. 31, 2003).
Ohlmeyer, M. H. J. et al., "Complex synthetic chemical libraries indexed with molecular tags," Proc. Natl. Acad. Sci. USA, vol. 90, pp. 10922-10926 (Dec. 1993).
Oprea, T. I. et al., "Is there a difference between leads and drugs? A historical perspective," J. Chem. Inf. Comput. Sci., vol. 41, No. 5, pp. 1308-1315 (Sep.-Oct. 2001).
Osterberg, T. and Norinder, U., "Prediction of polar surface area and drug transport processes using simple parameters and PLS statistics," J. Chem. Inf. Comput. Sci., vol. 40, No. 6, pp. 1408-1411 (2000).
Ostresh, J. M. et al., "'Libraries from libraries': Chemical transformation of combinatorial libraries to extend the range and repertoire of chemical diversity," Proc. Natl. Acad. Sci. USA, vol. 91, pp. 11138-11142 (Nov. 1994).
Paakkari, I. and Lindsberg, P., "Nitric oxide in the central nervous system," Ann. Med., vol. 27, No. 3, pp. 369-377 (1995).
Pan, Y. et al., "Computational redesign of human butyrylcholinesterase for anticocaine medication," Proc. Natl. Acad. Sci. USA, vol. 102, No. 46, pp. 16656-16661 (Nov. 15, 2005).
Pardridge, William M., "Blood-brain barrier drug targeting: the future of brain drug development," Mol. Interv., vol. 3, No. 2, pp. 90-105 (Mar. 2003).
Paris, D. et al., "Inhibition of Alzheimer's beta-amyloid induced vasoactivity and proinflammatory response in microglia by a cGMP-dependent mechanism," Exp. Neurol., vol. 157, No. 1, pp. 211-221 (1999).
Park, K. et al., "Sildenafil inhibits phosphodiesterase type 5 in human clitoral corpus cavernosum smooth muscle," Biochem. Biophys. Res. Commun., vol. 249, No. 3, pp. 612-617 (1998).
Pasquier, F. and Leys, D., "Blood pressure and Alzheimer's disease," Rev. Neurol. (Paris), vol. 154, No. 11, pp. 743-751 (1998).
Passer, B. et al., "Generation of an apoptotic intracellular peptide by gamma-secretase cleavage of Alzheimer's amyloid beta protein precursor," J. Alzheimers Dis., vol. 2, pp. 289-301 (2000).
Paternò, R. et al., "Role of $Ca^{2+}$-dependent $K^+$ channels in cerebral vasodilatation induced by increases in cyclic GMP and cyclic AMP in the rat," Stroke, vol. 27, No. 9, pp. 1603-1608, 8 pages (Sep. 1996).

(56) References Cited

OTHER PUBLICATIONS

Phillips, R. G. and LeDoux, J. E., "Differential contribution of amygdala and hippocampus to cued and contextual fear conditioning," Behav. Neurosci., vol. 106, pp. 274-285 (1992).
Price, J. M. et al., "Aging enhances vascular dysfunction induced by the Alzheimer's peptide beta-amyloid," Neurol. Res., vol. 26, No. 3, pp. 305-311 (Apr. 2004).
Prickaerts, J. et al., "cGMP, but not cAMP, in rat hippocampus is involved in early stages of object memory consolidation," Eur. J. Pharmacol., vol. 436, pp. 83-87 (2002).
Prickaerts, J. et al., "Effects of two selective phosphodiesterase type 5 inhibitors, sildenafil and vardenafil, on object recognition memory and hippocampal cyclic GMP levels in the rat," Neuroscience, vol. 113, No. 2, pp. 351-361 (2002).
Prickaerts, J. et al., "Phosphodiesterase type 5 inhibition improves early memory consolidation of object information," Neurochem. Int., vol. 45, No. 6, pp. 915-928 (2004).
Puolivali, J. et al., "Hippocampal Abeta42 levels correlate with spatial memory deficit in APP and PS1 double transgenic mice," Neurobiol. Dis., vol. 9, No. 3, pp. 339-347 (2002).
Puzzo, D. et al., "Amyloid-beta peptide inhibits activation of the nitric oxide/cGMP/cAMP-responsive element-binding protein pathway during hippocampal synaptic plasticity," J. Neurosci., vol. 25, No. 29, pp. 6887-6897 (Jul. 20, 2005).
Puzzo, D. et al., "Picomolar amyloid-beta positively modulates synaptic plasticity and memory in hippocampus," J. Neurosci., vol. 28, No. 53, pp. 14537-14545 (Dec. 31, 2008).
Rajfer, J. et al., "Case report: Avoidance of palpable corporal fibrosis due to priapism with upregulators of nitric oxide," J. Sex Med., vol. 3, pp. 173-176 (2006).
Randt, C. T. et al., "Brain cyclic AMP and memory in mice," Pharmacology Biochemistry, and Behavior, vol. 17, pp. 677-680 (1982).
Richter, W. et al., "Identification of inhibitor binding sites of the cAMP-specific phosphodiesterase 4," Cellular Signalling, vol. 13, No. 4, pp. 287-297 (2001).
Robinett, R. G. et al. "The discovery of substituted 4-(3-hydroxyanilino)-quinolines as potent RET kinase inhibitors," Bioorg. Med. Chem. Lett., vol. 17, No. 21, pp. 5886-5893 (Nov. 1, 2007).
Rostein, S. H. and Murcko, M. A., "GroupBuild: A Fragment-Based Method for De NoVo Drug Design," J. Med. Chem., vol. 36, pp. 1700-1710 (1993).
Rotella, D. P. et al., "N-3-Substituted Imidazoquinazolinones: Potent and Selective PDE5 Inhibitors as Potential Agents for Treatment of Erectile Dysfunction," J. Med. Chem., vol. 43, pp. 1257-1263 (2000).
Rotella, David P., "Phosphodiesterase 5 inhibitors: current status and potential applications," Nat. Rev. Drug Discov., vol. 1, No. 9, pp. 674-682 (Sep. 2002).
Russo, C. et al., "Signal transduction through tyrosine-phosphorylated C-terminal fragments of amyloid precursor protein via an enhanced interaction with Shc/Grb2 adaptor proteins in reactive astrocytes of Alzheimer's disease brain," The Journal of Biological Chemistry, vol. 277, pp. 35282-35288 (Sep. 20, 2002).
Saenz de Tejada, I. et al., "The phosphodiesterase inhibitory selectivity and the in vitro and in vivo potency of the new PDE5 inhibitor vardenafil," Int. J. Impot. Res., vol. 13, No. 5, pp. 282-290 (2001).
Salmon, S. E. et al., "Discovery of biologically active peptides in random libraries: Solution-phase testing after staged orthogonal release from resin beads," Proc. Natl. Acad. Sci. USA, vol. 90, pp. 11708-11712 (Dec. 1993).
Sant'Angelo, A. et al., "Usefulness of behavioral and electrophysiological studies in transgenic models of Alzheimer's disease," Neurochem. Res., vol. 28, No. 7, pp. 1009-1015 (Jul. 2003).
Scapin, G. et al., "Crystal structure of human phosphodiesterase 3B: atomic basis for substrate and inhibitor specificity," Biochemistry, vol. 43, No. 20, pp. 6091-6100 (May 25, 2004).
Schenk, D. et al., "Immunization with amyloid-beta attenuates Alzheimer-disease-like pathology in the PDAPP mouse," Nature, vol. 400, No. 6740, pp. 173-177 (Jul. 8, 1999).
Schenk, F. and Morris, R. G. M., "Dissociation between components of spatial memory in rats after recovery from the effects of retrohippocampal lesions," Exp. Brain Res., vol. 58, pp. 11-28 (1985).
Schiefer, J. and Sparing, R., "Transient global amnesia after intake of tadalafil, a PDE-5 inhibitor: a possible association?," Int. J. Impot. Res., vol. 17, No. 4, pp. 383-384 (2005).
Schudt, C. et al., "Zardaverine as a selective inhibitor of phosphodiesterase isozymes," Biochem. Pharmacol., vol. 42, No. 1, pp. 153-162 (Jun. 21, 1991).
Schultheiss, D. et al., "Central effects of sildenafil (Viagra) on auditory selective attention and verbal recognition memory in humans: a study with event-related brain potentials," World J. Urol., vol. 19, No. 1, pp. 46-50 (2001).
Schwardt, O. et al., "Drug discovery today," Curr. Top. Med. Chem., vol. 3, No. 1, pp. 1-9 (2003).
Scott, J. K. and Smith, G. P., "Searching for Peptide Ligands with an Epitope Library," Science, vol. 249, pp. 386-390 (Jul. 27, 1990).
Selig, D. K. et al., "Examination of the role of cGMP in long-term potentiation in the CA1 region of the hippocampus," Learn Mem., vol. 3, No. 1, pp. 42-48 (1996).
Selkoe, Dennis J., "Alzheimer's disease is a synaptic failure," Science, vol. 298, No. 5594, pp. 789-791 (Oct. 25, 2002).
Shankar, G. M. et al., "Natural Oligomers of the Alzheimer Amyloid-β Protein Induce Reversible Synapse Loss by Modulating an NMDA-Type Glutamate Receptor-Dependent Signaling Pathway," J. Neurosci., vol. 27, pp. 2866-2875 (Mar. 14, 2007).
Shea, Kenneth J., "Molecular Imprinting of Synthetic Network Polymers: The De Novo Synthesis of Macromolecular Binding and Catalytic Sites," TRIP, vol. 2, No. 5, pp. 166-173 (May 1994).
Silva, A. J. et al., "CREB and memory," Annu. Rev. Neurosci., vol. 21, pp. 127-148 (1998).
Simon, R. J. et al., "Peptoids: A modular approach to drug discovery," Proc. Natl. Acad. Sci. USA, vol. 89, pp. 9367-9371 (Oct. 1992).
Simons, M. et al., "Amyloidogenic processing of the human amyloid precursor protein in primary cultures of rat hippocampal neurons," The Journal of Neuroscience, vol. 16, No. 3, pp. 899-908 (Feb. 1, 1996).
Smith, C. C. et al., "Soluble beta-amyloid (A beta) 40 causes attenuation or potentiation of noradrenaline-induced vasoconstriction in rats depending upon the concentration employed," Neurosci. Lett., vol. 367, No. 1, pp. 129-132 (2004).
Snyder, E. M. et al., "Regulation of NMDA receptor trafficking by amyloid-beta," Nature Neuroscience, vol. 8, pp. 1051-1058 (Aug. 2005).
Snyder, P. B. et al., "The role of cyclic nucleotide phosphodiesterases in the regulation of adipocyte lipolysis," J. Lipid Res., vol. 46, No. 3, pp. 494-503 (2005).
Soderling, S. H. and Beavo, J. A., "Regulation of cAMP and cGMP signaling: new phosphodiesterases and new functions," Curr. Opin. Cell. Biol., vol. 12, No. 2, pp. 174-179 (2000).
Stéphan, A. et al., "Generation of aggregated beta-amyloid in the rat hippocampus impairs synaptic transmission and plasticity and causes memory deficits," J. Neurosci., vol. 21, No. 15, pp. 5703-5714 (Aug. 1, 2001).
Suhara, T. et al., "Abeta42 generation is toxic to endothelial cells and inhibits eNOS function through an Akt/GSK-3beta signaling-dependent mechanism," Neurobiol. Aging, vol. 24, No. 3, pp. 437-451 (2003).
Sung, B. J. et al., "Structure of the catalytic domain of human phosphodiesterase 5 with bound drug molecules," Nature, vol. 425, No. 6953, pp. 98-102 (Sep. 4, 2003).
Suter, Willi, "Predictive value of in vitro safety studies," Curr. Opin. Chem. Biol., vol. 10, No. 4, pp. 362-366 (2006).
Takahashi, R. H. et al., "Oligomerization of Alzheimer's beta-amyloid within processes and synapses of cultured neurons and brain," The Journal of Neuroscience, vol. 24, No. 14, pp. 3592-3599 (Apr. 7, 2004).
Takuma, K. et al., "ABAD enhances Abeta-induced cell stress via mitochondrial dysfunction," Faseb J, vol. 19, No. 6, 25 pages (Jan. 21, 2005).

(56) References Cited

OTHER PUBLICATIONS

Taylor, R. D. et al., "A review of protein-small molecule docking methods," Journal of Computer-Aided Molecular Design, vol. 16, No. 3, pp. 151-166 (2002).
Teague, S. J. et al., "The Design of Leadlike Combinatorial Libraries," Angew. Chem. Int. Ed. Engl., vol. 38, No. 24, pp. 3743-3748 (1999).
Terrett, N. K. et al., "Sildenafil (VIAGRA™), a potent and selective inhibitor of type 5 cGMP phosphodiesterase with utility for the treatment of male erectile dysfunction," Bioorg. Med. Chem. Lett., vol. 6, No. 15, pp. 1819-1824 (1996).
Thatcher, G. R. J. et al., "Novel nitrates as NO mimetics directed at Alzheimer's disease," J. Alzheimers Dis., vol. 6, pp. S75-S84 (2004).
Thatcher, G. R. J. et al., "Nitric oxide mimetic molecules as therapeutic agents in Alzheimer's disease," Current Alzheimer Research, vol. 2, No. 2, pp. 171-182 (2005).
Tran, M. H. et al., "Amyloid beta-peptide induces nitric oxide production in rat hippocampus: association with cholinergic dysfunction and amelioration by inducible nitric oxide synthase inhibitors," Faseb J., vol. 15, No. 8, 20 pages (Apr. 6, 2001).
Trinchese, F. et al., "Alzheimer Aß Increases Neurotransmitter Release and Blocks Synaptic Plasticity in Hippocampal Cultures," The 9th International Conference on Alzheimer's Disease and Related Disorders Abstr., Poster Session P3-323, 1 page (2004).
Trinchese, F. et al., "Progressive age-related development of Alzheimer-like pathology in APP/PS1 mice," Ann. Neurol., vol. 55, No. 6, pp. 801-814 (2004).
Troy, C. M. et al., "Caspase-2 mediates neuronal cell death induced by beta-amyloid," J. Neurosci., vol. 20, No. 4, pp. 1386-1392 (Feb. 15, 2000).
Tully, T. et al., "Targeting the CREB pathway for memory enhancers," Nat. Rev. Drug Discov., vol. 2, No. 4, pp. 267-277 (Apr. 2003).
Turko, I. V. et al., "Potential roles of conserved amino acids in the catalytic domain of the cGMP-binding cGMP-specific phosphodiesterase (PDE5)," J. Biol. Chem., vol. 273, No. 11, pp. 6460-6466 (Mar. 13, 1998).
Turner, Bryan M., "Cellular memory and the histone code," Cell, vol. 111, No. 3, pp. 285-291 (Nov. 1, 2002).
Ukita, T. et al., "1,7- and 2,7-Naphthyridine Derivatives as Potent and Highly Specific PDE5 Inhibitors," Bioorganic & Medicinal Chemistry Letters, vol. 13, pp. 2341-2345 (2003).
Uthayathas, S. et al., "Versatile effects of sildenafil: recent pharmacological applications," Pharmacol. Rep., vol. 59, No. 2, pp. 150-163 (2007).
Van de Waterbeemd, H. and Gifford, E., "ADMET in silico modelling: towards prediction paradise?," Nat. Rev. Drug Discov., vol. 2, No. 3, pp. 192-204 (Mar. 2003).
Van Staveren, W. C. G. et al., "mRNA expression patterns of the cGMP-hydrolyzing phosphodiesterases types 2, 5, and 9 during development of the rat brain," J. Comp. Neurol., vol. 467, No. 4, pp. 566-580 (2003).
Van Staveren, W. C. G. et al., "Species differences in the localization of cGMP-producing and NO-responsive elements in the mouse and rat hippocampus using cGMP immunocytochemistry," Eur. J. Neurosci., vol. 19, No. 8, pp. 2155-2168 (2004).
Venturini, G. et al., "Beta-amyloid inhibits NOS activity by subtracting NADPH availability," Faseb J., vol. 16, No. 14, 21 pages (Oct. 18, 2002).
Villiger, J. W. and Dunn, A. J., "Phosphodiesterase inhibitors facilitate memory for passive avoidance conditioning," Behavioral and Neural Biology, vol. 31, pp. 354-359 (1981).
Vitolo, O. V. et al., "Amyloid beta-peptide inhibition of the PKA/CREB pathway and long-term potentiation: reversibility by drugs that enhance cAMP signaling," Proc. Natl. Acad. Sci. USA, vol. 99, No. 20, pp. 13217-13221 (Oct. 1, 2002).
Walker, D. K. et al., "Pharmacokinetics and metabolism of sildenafil in mouse, rat, rabbit, dog and man," Xenobiotica, vol. 29, No. 3, pp. 297-310 (1999).
Walsh, D. M. et al., "Certain inhibitors of synthetic amyloid beta-peptide (Abeta) fibrillogenesis block oligomerization of natural Abeta and thereby rescue long-term potentiation," The Journal of Neuroscience, vol. 25, No. 10, pp. 2455-2462 (Mar. 9, 2005).
Walsh, D. M. et al., "Naturally secreted oligomers of amyloid beta protein potently inhibit hippocampal long-term potentiation in vivo," Nature, vol. 416, No. 6880, pp. 535-539 (Apr. 4, 2002).
Wang, H. et al., "ATP-Sensitive Potassium Channel Openers and 2,3-Dimethyl-2-Butylamine Derivatives," Current Medicinal Chemistry, vol. 14, No. 2, pp. 133-155 (2007).
Wang, P. et al., "Characterization of human, dog and rabbit corpus cavernosum type 5 phosphodiesterases," Life Sciences, vol. 68, No. 17, pp. 1977-1987 (2001).
Wang, Q. et al., "β-Amyloid-mediated inhibition of NMDA receptor-dependent long-term potentiation induction involves activation of microglia and stimulation of inducible nitric oxide synthase and superoxide," J. Neurosci., vol. 24, pp. 6049-6056 (Jul. 7, 2004).
Wang, Y. D. et al., "Inhibitors of Src Tyrosine Kinase: The Preparation and Structure-Activity Relationship of 4-Anilino-3-cyanoquinolines and 4-Anilinoquinazolines," Bioorganic & Medicinal Chemistry Letters, vol. 10, No. 21, pp. 2477-2480 (2000).
Wells, J. N. et al., "Cyclic nucleotide phosphodiesterase activities of pig coronary arteries," Biochimica et Biophysica Acta, vol. 384, No. 2, pp. 430-442 (1975).
Werner, T. and Nelson, P. J., "Joining high-throughput technology with in silico modelling advances genome-wide screening towards targeted discovery," Brief Funct. Genomic Proteomic, vol. 5, No. 1, pp. 32-36 (2006).
Wirtz-Brugger, F. and Giovanni, A., "Guanosine 3',5'-cyclic monophosphate mediated inhibition of cell death induced by nerve growth factor withdrawal and beta-amyloid: protective effects of propentofylline," Neuroscience, vol. 99, No. 4, pp. 737-750 (2000).
Wong, A. et al., "Advanced glycation endproducts co-localize with inducible nitric oxide synthase in Alzheimer's disease," Brain Res., vol. 920, No. 1-2, pp. 32-40 (2001).
Wu, J. et al., "Beta-Amyloid-(1-40) increases long-term potentiation in rat hippocampus in vitro," Eur. J. Pharmacol., vol. 284, No. 3, pp. R1-R3 (1995).
Wulff, Gunter, "Molecular Recognition in Polymers Prepared by Imprinting with Templates," Polymeric Reagents and Catalysts, ACS Symposium Series No. 308, pp. 186-230 (1986).
Xie, Z. et al., "Peroxynitrite mediates neurotoxicity of amyloid beta-peptide1-42- and lipopolysaccharide-activated microglia," J. Neurosci., vol. 22, No. 9, pp. 3484-3492 (May 1, 2002).
Xiong, Y. et al., "Characterization of a catalytic ligand bridging metal ions in phosphodiesterases 4 and 5 by molecular dynamics simulations and hybrid quantum mechanical/molecular mechanical calculations," Biophys. J., vol. 91, No. 5, pp. 1858-1867 (Sep. 2006).
Xiong, Y. et al., "Dynamic structures of phosphodiesterase-5 active site by combined molecular dynamics simulations and hybrid quantum mechanical/molecular mechanical calculations," J. Comput Chem., vol. 29, pp. 1259-1267 (2007).
Xu, R. X. et al., "Atomic structure of PDE4: insights into phosphodiesterase mechanism and specificity," Science, vol. 288, No. 5472, pp. 1822-1825 (Jun. 9, 2000).
Yang, G. F. et al., "Understanding the structure-activity and structure-selectivity correlation of cyclic guanine derivatives as phosphodiesterase-5 inhibitors by molecular docking, CoMFA and CoMSIA analyses," Bioorg. Med. Chem., vol. 14, No. 5, pp. 1462-1473 (2006).
Yin, J. C. P. et al., "Induction of a dominant negative CREB transgene specifically blocks long-term memory in *Drosophila*," Cell, vol. 79, No. 1, pp. 49-58 (Oct. 7, 1994).
Yu, R. et al., "The retromer and Alzheimer's disease: characterizing retromer knock-down mice with a nd without APP mutations," Soc. Neurosci. Abstr., Presentation No. 661.8, 2 pages (Nov. 15, 2005).
Zhan, C.-G. and Chipman, D. M., "Cavity size in reaction field theory," J. Chem. Phys., vol. 109, No. 24, pp. 10543-10558 (Dec. 22, 1998).
Zhan, C.-G. and Chipman, D. M., "Effect of hydrogen bonding on the vibrations of benzosemiquinone radical anion," J. Phys. Chem. A, vol. 102, pp. 1230-1235 (1998).

(56) References Cited

OTHER PUBLICATIONS

Zhan, C.-G. and Dixon, D. A., "Absolute hydration free energy of the proton from first-principles electronic structure calculations," J. Phys. Chem. A, vol. 105, No. 51, pp. 11534-11540 (Dec. 27, 2001).

Zhan, C.-G. and Dixon, D. A., "First-principles determination of absolute hydration free energy of hydroxide ion," J. Phys. Chem. A, vol. 106, No. 42, pp. 9737-9744 (Oct. 24, 2002).

Zhan, C.-G. and Dixon, D. A., "Hydration of the fluoride anion: Structures and absolute hydration free energy from first-principles electronic structure calculations," J. Phys. Chem. A, vol. 108, No. 11, pp. 2020-2029 (Mar. 18, 2004).

Zhan, C.-G. and Dixon, D. A., "The nature and absolute hydration free energy of the solvated electron in water," J. Phys. Chem. B, vol. 107, No. 18, pp. 4403-4417 (May 8, 2003).

Zhan, C.-G. and Gao, D., "Catalytic mechanism and energy barriers for butyrylcholinesterase-catalyzed hydrolysis of cocaine," Biophys. J., vol. 89, No. 6, pp. 3863-3872 (Dec. 2005).

Zhan, C.-G. et al., "Chromogenic and neurotoxic effects of aliphatic γ-diketone: Computational insights into the molecular structures and mechanism," J. Phys. Chem. B, vol. 108, pp. 6098-6104 (2004).

Zhan, C.-G. et al., "Computational insights into the chemical structures and mechanisms of the chromogenic and neurotoxic effects of aromatic γ-diketones," J. Phys. Chem. B, vol. 107, No. 12, pp. 2853-2861 (Mar. 27, 2003).

Zhan, C.-G. et al., "Determination of two structural forms of catalytic bridging ligand in zinc-phosphotriesterase by molecular dynamics simulation and quantum chemical calculation," J. Am. Chem. Soc., vol. 121, No. 32, pp. 7279-7282 (1999).

Zhan, C.-G. et al., "Energy barriers for alkaline hydrolysis of carboxylic acid esters in aqueous solution by reaction field calculations," J. Phys. Chem. A, vol. 104, No. 32, pp. 7672-7678 (2000).

Zhan, C.-G. et al., "Theoretical determination of chromophores in the chromogenic effects of aromatic neurotoxicants," J. Am. Chem. Soc., vol. 124, No. 11, pp. 2744-2752 (Mar. 19, 2002).

Zhan, C.-G. et al., "Theoretical studies of photoelectron spectra of SO42—(H2O)n clusters and the extrapolation to bulk solution," J. Chem. Phys., vol. 119, No. 2, pp. 781-793 (Jul. 8, 2003).

Zhan, C.-G. et al., "Volume polarization in reaction field theory," J. Chem. Phys., vol. 108, Nos. 1-2, pp. 177-192 (Jan. 1-Jun. 22, 1998).

Zhan, C.G. and Zheng, F., "First computational evidence for a catalytic bridging hydroxide ion in a phosphodiesterase active site," J. Am. Chem. Soc., vol. 123, No. 12, pp. 2835-2838 (Mar. 28, 2001).

Zhang, H. T. et al., "Inhibition of cyclic AMP phosphodiesterase (PDE4) reverses memory deficits associated with NMDA receptor antagonism," Neuropsychopharmacology, vol. 23, No. 2, pp. 198-204 (2000).

Zhang, K. Y. et al., "A glutamine switch mechanism for nucleotide selectivity by phosphodiesterases," Mol. Cell, vol. 15, No. 2, pp. 279-286 (Jul. 23, 2004).

Khaldeeva and Konshin, "Investigation of Naphthyrdrines," 4 pages (1976).

Musial et al., "Recent Developments in Cholinesterases Inhibitors for Alzheimer's Disease Treatment," Current Medicinal Chemistry 14(25), pp. 2654-2679 (2007).

Communication pursuant to Article 94(3) EPC dated Feb. 8, 2018 in corresponding European Patent Application No. 14826002.9 (5 pages).

Fiorito, et al., "Identification of a Novel 1,2,3,4-Tetrahydrobenzo[b][1,6]naphthyridine Analogue as a Potent Phosphodiesterase 5 Inhibitor with Improved Aqueous Solubility for the Treatment of Alzheimer's Disease", Journal of Medicinal Chemistry, 60:8858-8875, 2017 (18 pages).

* cited by examiner

PHOSPHODIESTERASE INHIBITORS AND USES THEREOF

CROSS REFERENCE TO RELATED APPLICATION

This application is a National Stage Entry of PCT International Application No. PCT/US14/47031 filed Jul. 17, 2014, which claims the benefit of and priority to U.S. Provisional Patent Application No. 61/847,280, filed on Jul. 17, 2013, the contents of which are hereby incorporated by reference in their entirety.

GOVERNMENT SUPPORT

This invention was made with government support under NIH/NIA Grant No. 1U01AG032973 awarded by the National Institute of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Alzheimer's disease (AD) is a neurodegenerative disorder that is the most common cause of dementia among elderly persons. It is characterized by progressive memory loss, synaptic dysfunction and accumulation of amyloid β-peptides (Aβ). It is caused in part by increased levels of amyloid-β-peptide 1-42 (Aβ42). Approved drugs to treat AD include cholinesterase inhibitors such as Cognex® (tacrine), Aricept® (donepezil), Exelon® (rivastigmine) and Razdyne® (galantamine); and the N-methyl d-aspartate receptor antagonist Namenda® (memantine). However, several of these medications suffer from limited efficacy and produce untoward side effects.

Phosphodiesterase 5 (PDE5) inhibitors are widely used as therapeutics for erectile dysfunction and pulmonary hypertension. These inhibitors are believed to increase cGMP levels, which enhances phosphorylation of the transcription factor and memory-affecting molecule cAMP-responsive element binding (CREB) through activation of cGMP-dependent-protein kinases.

Cyclic adenosine monophosphate (cAMP) and cyclic guanosine monophosphate (cGMP), nucleotide biological second messengers, regulate various biological processes, such as blood flow regulation, cardiac muscle contraction, cell differentiation, neural transmission, glandular secretion, and gene expression. Intracellular receptors for these molecules include cyclic nucleotide phosphodiesterases (PDEs), cyclic nucleotide dependent protein kinases (PGK), and cyclic nucleotide-gated channels. PDEs are a large family of proteins that catalyze the hydrolysis of 3',5'-cyclic nucleotides to the corresponding 5' monophosphates. There are eleven related, but biochemically distinct, human PDE gene groups. Some PDEs are specific for hydrolysis of cAMP (such as PDE4, PDE7, and PDE8), and some are cGMP specific (such as PDE5, PDE6, and PDE9), while some PDEs have mixed specificity (such as PDE1, PDE2, PDE3, PDE10, and PDE11).

Representative PDE 5 inhibitors are cyclic guanosine 3',5'-monophosphate type five cGMP PDE inhibitors, also known as PDE-5 inhibitors, which include, for example, sildenafil, tadalafil, zaprinast, and vardenafil. PDE5 inhibitors increase cGMP levels by inhibiting the degradative action of PDE5 on cGMP. Current PDE5 inhibitors suffer from drawbacks such as limited selectivity over other PDE sub-types. There remains a need for structurally novel PDE5 inhibitors.

SUMMARY OF THE INVENTION

In one aspect, the invention is directed to a class of benzo[b][1,6]naphthyridine derivatives of formula (I)

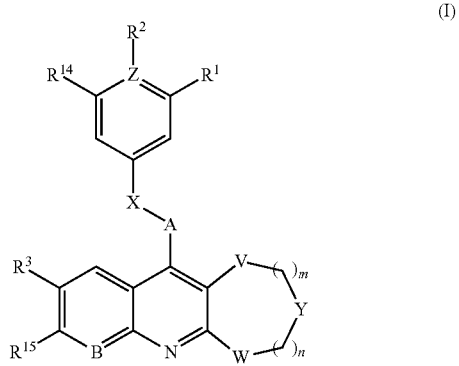

wherein
A is O or $NR^4$;
B is $CR^{16}$ or N;
V is a bond or C(O);
W is a bond or $NR^{13}$;
X is —$(C_1$-$C_3)$-alkyl, —$(C1¬C3)$-alkyl substituted with at least one D, C(O), S, S(O), or $S(O)_2$;
Y is $NR^5$, O or S;
Z is C or N;
$R^1$ is hydrogen, halogen or —$(C_1$-$C_6)$-haloalkyl;
$R^2$ is hydrogen or —$OR^6$;
$R^3$ is hydrogen, —OMe, —$CF_3$, —CN or halogen;
$R^4$ is hydrogen or —$(C_1$-$C_3)$-alkyl;
$R^5$ is hydrogen, —$(C_1$-$C_3)$-alkyl, —$(C_3$-$C_5)$-cycloalkyl, —$C(O)R^7$, —$C(O)OR^7$, —$C(O)N(R^7)_2$, —$S(O)_2R^7$;
$R^6$ is hydrogen, —$(C_1$-$C_6)$-alkyl, —$(C_1$-$C_6)$-haloalkyl, or —$(C_3$-$C_8)$-cycloalkyl;
$R^7$ is independently hydrogen, —$(C_1$-$C_6)$-alkyl, —$(C_1$-$C_6)$-haloalkyl, or aryl;
$R^8$ is hydrogen, —$(C_1$-$C_6)$-alkyl, —$(C_1$-$C_6)$-haloalkyl, —$(C_3$-$C_8)$-cycloalkyl, —$NR^9R^{10}$, —$S(O)_2R^{11}$, or heterocyclyl;
$R^9$ and $R^{10}$ are each independently hydrogen, —$(C_1$-$C_6)$-alkyl, —$(C_3$-$C_8)$-cycloalkyl, or $C(O)R^{11}$, wherein the —$(C_1$-$C_6)$-alkyl or —$(C_3$-$C_8)$-cycloalkyl are optionally substituted with —$(C_1$-$C_6)$-alkyl, —$(C_3$-$C_8)$-cycloalkyl, —$NR^{11}R^{12}$, —$SR^{11}$, or heterocyclyl; or, $R^9$ and $R^{10}$ together with the nitrogen atom to which they are attached form a 3 to 8-membered heterocycle, wherein any one of the ring carbon atoms is optionally replaced with a heteroatom, and wherein the heterocycle is optionally substituted with —$(C_1$-$C_6)$-alkyl;

$R^{11}$ and $R^{12}$ are each independently hydrogen, —$(C_1$-$C_6)$-alkyl, or —$(C_3$-$C_8)$-cycloalkyl;

$R^{13}$ is hydrogen, —$(C_1$-$C_6)$-alkyl, —$(C_3$-$C_5)$-cycloalkyl, —$C(O)R^7$, —$C(O)OR^7$, —$C(O)N(R^7)_2$, or —$S(O)_2R^7$;

$R^{14}$ is hydrogen, halogen or —$(C_1$-$C_6)$-haloalkyl;

$R^{15}$ is hydrogen, —$OR^{17}$, —OH or halogen;

$R^{16}$ is hydrogen, —$OR^{17}$, —OH or halogen;

$R^{17}$ is hydrogen, —$(C_1$-$C_6)$-alkyl, —$(C_1$-$C_6)$-haloalkyl, or —$(C_3$-$C_8)$-cycloalkyl;

m and n are each 0, 1, 2, or 3, provided that the sum of m+n is an integer from 2-4;

or a pharmaceutically acceptable salt or tautomer thereof; with the proviso that $R^1$ and $R^2$ are not both hydrogen when V and W are each a bond, Y is $NR^5$, A is $NR^4$, X is CO, n=2 and m=1.

In some embodiments, the compounds of the invention decrease PDE activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

In some embodiments, the compounds of the invention inhibit phosphodiesterase. In some embodiments, the phosphodiesterase is phosphodiesterase type V (PDE5).

In some embodiments, the compounds of the invention have an IC50 for phosphodiesterase of at least about 0.1 nM, at least about 1 nM, at least about 5 nM, at least about 10 nM, at least about 25 nM, at least about 50 nM, at least about 100 nM, at least about 200 nM, at least about 300 nM, at least about 400 nM, at least about 500 nM, at least about 600 nM, at least about 700 nM, at least about 800 nM, at least about 900 nM, or at least about 1000 nM.

In another aspect, the invention is directed to compositions comprising a compound of formula (I) and a pharmaceutically acceptable carrier.

In another aspect, the invention is directed to a method of inhibiting phosphodiesterase comprising contacting a phosphodiesterase with a compound of formula (I) or a composition comprising a compound of formula (I). In some embodiments, the phosphodiesterase is PDE5.

In another aspect, the invention is directed to a method of treating neurodegenerative disease in a subject comprising administration of a therapeutically effective amount of a compound of formula (I). In some embodiments, the disease is Alzheimer's Disease.

In another aspect, the invention is directed to a method of increasing long-term potentiation in a subject comprising administration of a therapeutically effective amount of a compound of formula (I).

In another aspect, the invention is directed to a method of improving memory in a subject comprising administration of a therapeutically effective amount of a compound of formula (I). In some embodiments, the subject has a neurodegenerative disease. In some embodiments, the neurodegenerative disease is Alzheimer's Disease.

In another aspect, the invention is directed to a method of improving synaptic function in a subject comprising administration of a therapeutically effective amount of a compound of formula (I). In some embodiments, the subject has a neurodegenerative disease. In some embodiments, the neurodegenerative disease is Alzheimer's Disease.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

DETAILED DESCRIPTION OF THE INVENTION

Figure 1:
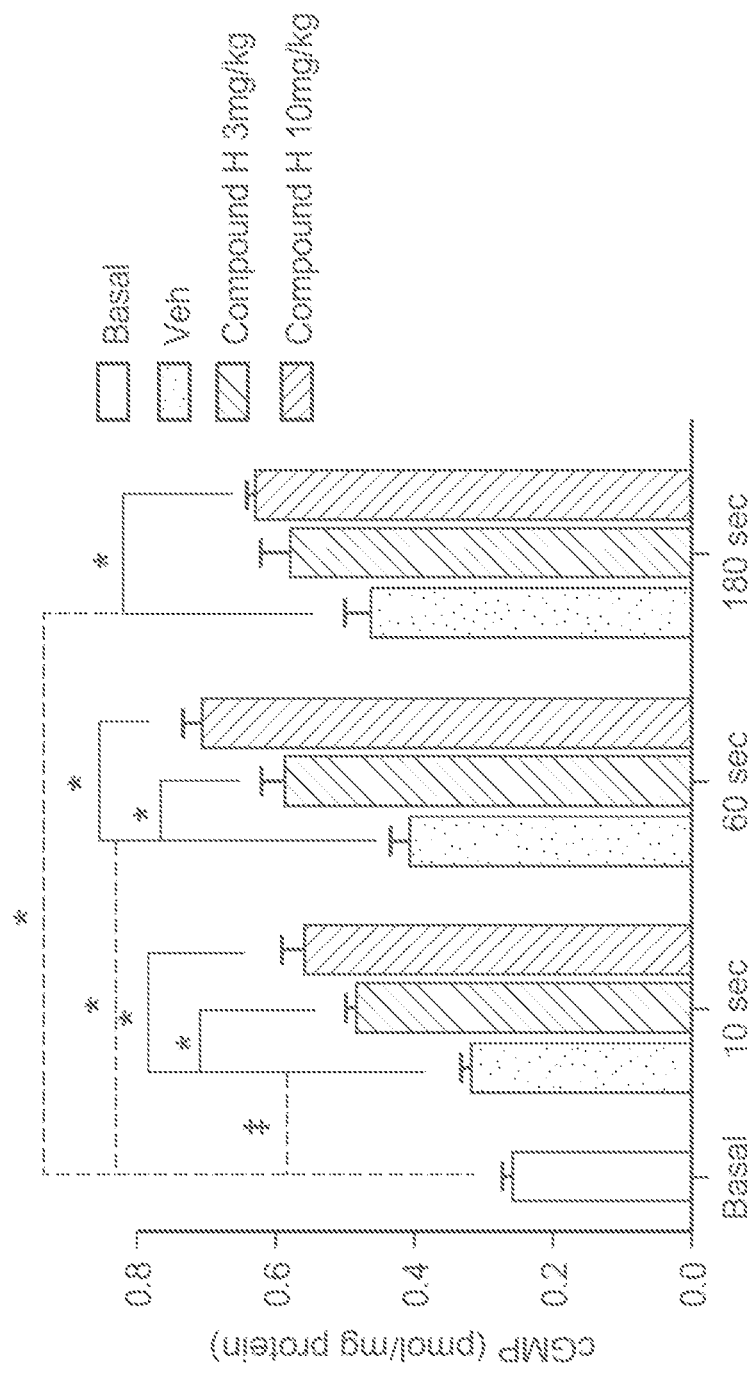
FIG. 1 shows the effects of compound H on hippocampal cGMP levels in mice.

Treatment for AD remains a major focus in the medical community. To that end, several biological targets for treatment of AD are being explored such as Tau, beta-secretase, and gamma-secretase. AD purportedly begins as a synaptic disorder produced at least in part, by Aβ (Selkoe, D. J. *Science* 2002, 298, 789-791; herein incorporated by reference in its entirety). Aβ-induced reduction in long-term-potentiation (LTP), a physiological correlate of synaptic plasticity that is thought to underlie learning and memory, and phosphorylation of the memory transcription factor CREB, are ameliorated by nitric oxide (NO) donors and cGMP-analogs (Puzzo, et al, *J. Neurosci* 2005, 25, 6887-6897; herein incorporated by reference in its entirety). Vice-versa, genetic ablation of NO-synthase 2 (NOS2) results in worsening of the AD phenotype in mice expressing mutated amyloid precursor protein (APP) (Colton et al. *Proceedings of the National Academy of Sciences of the United States of America* 2006, 103, 12867-12872; herein incorporated by reference in its entirety). Taken together, these findings show that up-regulation of the NO pathway can be protective in AD.

Despite the neuroprotective function of NO, the gas has also been viewed as a major agent of neuropathology and cell death when produced in high quantities. High amounts of NO lead to generation of significant quantity of peroxinitrites that are responsible for oxidative and nitrosative stress in Aβ-induced cell death. Release of low amounts of NO by the constitutive forms of NOS that include both the neuronal and the endothelial isoforms, n-NOS and e-NOS, promotes synaptic plasticity and learning, whereas uncontrolled production of high amounts of the gas by the inducible form of NOS (i-NOS) can promote oxidative and nitrosative stress via production of peroxinitrite. Thus, both Aβ-induced downregulation of the NO cascade which blocks plasticity and memory and generation of peroxinitrites leading to cell death, can play roles in AD.

Strategies that can bypass NO production focus on steps downstream of NO generation. Agents that enhance NO/cGMP/CREB signaling can rescue Ab-induced reduction of synaptic plasticity and memory (See, WO 2010/074783 and references cited therein; Prickaerts, et al., *Eur. J. Pharmacol.* 1999, 10, 731-737; and *Neuroscience* 2002, 113, 351-361; each herein incorporated by reference in its entirety).

In one aspect, the invention is directed to derivatives of formula (I):

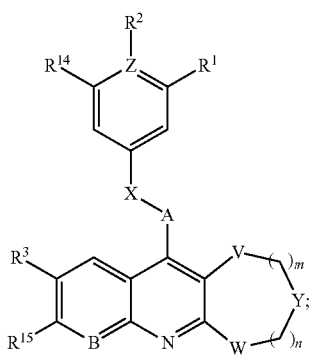

(I)

more particularly to a derivatives of formula (Ia):

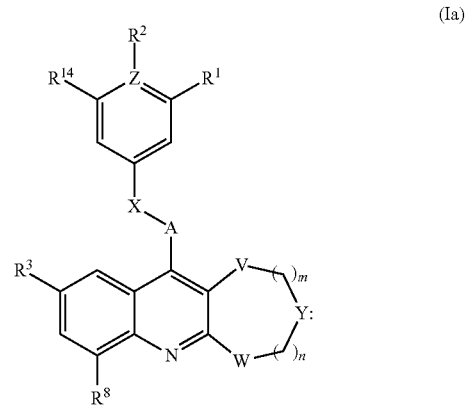

(Ia)

still more particularly to derivatives of formula (Ib):

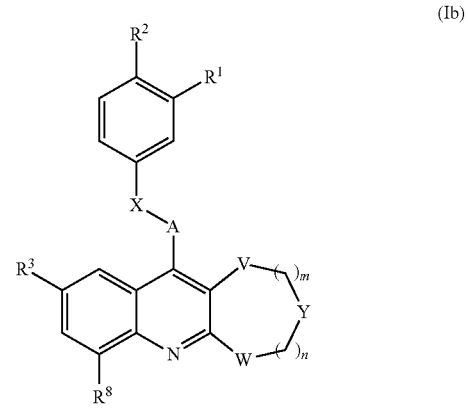

(Ib)

wherein
A is O or $NR^4$;
B is $CR^{16}$ or N;
V is a bond or C(O);
W is a bond or $NR^{13}$;
X is —$(C_1$-$C_3)$-alkyl, —$(C1¬C3)$-alkyl substituted with at least one D, C(O), S, S(O), or $S(O)_2$;
Y is $NR^5$, O or S;
Z is C or N;
R1 is hydrogen, halogen or —(C1-C6)-haloalkyl;
$R^2$ is hydrogen or —$OR^6$;
R3 is hydrogen, —OMe, —CF3, —CN or halogen;
$R^4$ is hydrogen or —$(C_1$-$C_3)$-alkyl;
$R^5$ is hydrogen, —$(C_1$-$C_3)$-alkyl, —$(C_3$-$C_5)$-cycloalkyl, —$C(O)R^7$, —$C(O)OR^7$, —$C(O)N(R^7)_2$, —$S(O)_2R^7$;
$R^6$ is hydrogen, —$(C_1$-$C_6)$-alkyl, —$(C_1$-$C_6)$-haloalkyl, or —$(C_3$-$C_8)$-cycloalkyl;
$R^7$ is independently hydrogen, —$(C_1$-$C_6)$-alkyl, —$(C_1$-$C_6)$-haloalkyl, or aryl;
$R^8$ is hydrogen, —$(C_1$-$C_6)$-alkyl, —$(C_1$-$C_6)$-haloalkyl, —$(C_3$-$C_8)$-cycloalkyl, —$NR^9R^{10}$, —$S(O)_2R^{11}$, or heterocyclyl;
$R^9$ and $R^{10}$ are each independently hydrogen, —$(C_1$-$C_6)$-alkyl, —$(C_3$-$C_8)$-cycloalkyl, or $C(O)R^{11}$, wherein the —$(C_1$-$C_6)$-alkyl or —$(C_3$-$C_8)$-cycloalkyl are optionally substituted with —$(C_1$-$C_6)$-alkyl, —$(C_3$-$C_8)$-cycloalkyl, —$NR^{11}R^{12}$, —$S^{11}$, or heterocyclyl; or, $R^9$ and $R^{10}$ together with the nitrogen atom to which they are attached form a 3 to 8-membered heterocycle, wherein any one of the ring carbon atoms is optionally replaced with a heteroatom, and wherein the heterocycle is optionally substituted with —($C_1$-$C_6$)-alkyl;

$R^{11}$ and $R^{12}$ are each independently hydrogen, —($C_1$-$C_6$)-alkyl, or —($C_3$-$C_8$)-cycloalkyl;

$R^{13}$ is hydrogen, —($C_1$-$C_6$)-alkyl, —($C_3$-$C_5$)-cycloalkyl, —C(O)$R^7$, —C(O)O$R^7$, —C(O)N($R^7$)$_2$, or —S(O)$_2R^7$;

$R^{14}$ is hydrogen, halogen or —($C_1$-$C_6$)-haloalkyl;

$R^{15}$ is hydrogen, —O$R^{17}$, —OH or halogen;

$R^{16}$ is hydrogen, —O$R^{17}$, —OH or halogen;

$R^{17}$ is hydrogen, —($C_1$-$C_6$)-alkyl, —($C_1$-$C_6$)-haloalkyl, or —($C_3$-$C_8$)-cycloalkyl;

m and n are each 0, 1, 2, or 3, provided that the sum of m+n is an integer from 1-4;

or a pharmaceutically acceptable salt or tautomer thereof; with the proviso that $R^1$ and $R^2$ are not both hydrogen when V and W are each a bond, Y is $NR^5$, A is $NR^4$, X is CO, n=2 and m=1.

In another aspect, the invention is directed to derivatives of formula (Ic):

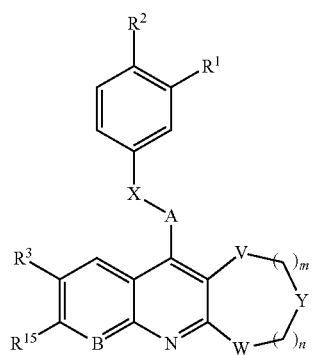

(Ic)

wherein
A is O or $NR^4$;
B is $CR^{16}$ or N;
V is a bond or C(O);
W is a bond or $NR^{13}$;
X is —($C_1$-$C_3$)-alkyl, —($C_1$–$C_3$)-alkyl substituted with at least one D, C(O), S, S(O), or S(O)$_2$;
Y is $NR^5$, O or S;
$R^1$ is hydrogen, halogen or —($C_1$-$C_6$)-haloalkyl;
$R^2$ is hydrogen or —O$R^6$;
$R^3$ is hydrogen, —OMe, —$CF_3$, —CN or halogen;
$R^4$ is hydrogen or —($C_1$-$C_3$)-alkyl;
$R^5$ is hydrogen, —($C_1$-$C_3$)-alkyl, —($C_3$-$C_5$)-cycloalkyl, —C(O)$R^7$, —C(O)O$R^7$, —C(O)N($R^7$)$_2$, —S(O)$_2R^7$;
$R^6$ is hydrogen, —($C_1$-$C_6$)-alkyl, —($C_1$-$C_6$)-haloalkyl, or —($C_3$-$C_8$)-cycloalkyl;
$R^7$ is independently hydrogen, —($C_1$-$C_6$)-alkyl, —($C_1$-$C_6$)-haloalkyl, or aryl;
$R^8$ is hydrogen, —($C_1$-$C_6$)-alkyl, —($C_1$-$C_6$)-haloalkyl, —($C_3$-$C_8$)-cycloalkyl, —$NR^9R^{10}$, —S(O)$_2R^{11}$, or heterocyclyl;
$R^9$ and $R^{10}$ are each independently hydrogen, —($C_1$-$C_6$)-alkyl, —($C_3$-$C_8$)-cycloalkyl, or C(O)$R^{11}$, wherein the —($C_1$-$C_6$)-alkyl or —($C_3$-$C_8$)-cycloalkyl are optionally substituted with —($C_1$-$C_6$)-alkyl, —($C_3$-$C_8$)-cycloalkyl, —$NR^{11}R^{12}$, —$S^{11}$, or heterocyclyl; or, $R^9$ and $R^{10}$ together with the nitrogen atom to which they are attached form a 3 to 8-membered heterocycle, wherein any one of the ring carbon atoms is optionally replaced with a heteroatom, and wherein the heterocycle is optionally substituted with —($C_1$-$C_6$)-alkyl;

$R^{11}$ and $R^{12}$ are each independently hydrogen, —($C_1$-$C_6$)-alkyl, or —($C_3$-$C_8$)-cycloalkyl;

$R^{13}$ is hydrogen, —($C_1$-$C_6$)-alkyl, —($C_3$-$C_5$)-cycloalkyl, —C(O)$R^7$, —C(O)O$R^7$, —C(O)N($R^7$)$_2$, or —S(O)$_2R^7$;

$R^{15}$ is hydrogen, —O$R^{17}$, —OH or halogen;

$R^{16}$ is hydrogen, —O$R^{17}$, —OH or halogen;

$R^{17}$ is hydrogen, —($C_1$-$C_6$)-alkyl, —($C_1$-$C_6$)-haloalkyl, or —($C_3$-$C_8$)-cycloalkyl;

m and n are each 0, 1, 2, or 3, provided that the sum of m+n is an integer from 1-4;

or a pharmaceutically acceptable salt or tautomer thereof; with the proviso that $R^1$ and $R^2$ are not both hydrogen when V and W are each a bond, Y is $NR^5$, A is $NR^4$, X is CO, n=2 and m=1.

The compounds and/or compositions of the invention may be effective in treating, reducing, and/or suppressing complications related to PDE, including PDE5, such as, for example, erectile dysfunction.

ABBREVIATIONS AND DEFINITIONS

The terms "phosphodiesterase inhibitor" or "PDE inhibitor" refer to compounds and salts or solvates thereof that function by inhibiting the activity of the enzyme phosphodiesterase. An exemplary phosphodiesterase is phosphodiesterase type 5 (PDE5). A PDE inhibitor can be a compound that decreases the activity of PDE in vivo and/or in vitro. Exemplary PDE5 inhibitors may be found in U.S. Pat. Nos. 5,250,534; 5,859,006; 6,362,178; and 7,378,430; each of which hereby incorporated by reference in its entirety.

The term "compound of the invention" as used herein means a compound of formula (I) or any subgenus or species thereof. The term is also intended to encompass salts, hydrates, and solvates thereof.

The term "composition(s) of the invention" as used herein means compositions comprising a compound of the invention, and salts, hydrates, or solvates thereof. The compositions of the invention may further comprise other agents such as, for example, carriers, excipients, stabilants, lubricants, solvents, and the like.

The term "alkyl", as used herein, unless otherwise indicated, refers to a monovalent aliphatic hydrocarbon radical having a straight chain or branched chain. Examples of "alkyl" groups include methyl, ethyl, propyl, isopropyl, butyl, iso-butyl, sec-butyl, tert-butyl, pentyl, hexyl, heptyl, and the like.

The term "D" refers to a deuterium atom, and is known in the art to refer to a deuterium enriched species, that is, where D is present above its natural isotopic abundance.

The term "haloalkyl", as used herein, refers to an alkyl group substituted with one or more halogen atoms. The term also encompasses haloalkyl groups containing more than one species of halogen atom, for example —$CF_2Cl$, and the like.

The term "halogen", as used herein, means chlorine (Cl), fluorine (F), iodine (I) or bromine (Br).

The term "solvate" as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "pharmaceutical composition" refers to a mixture of one or more of the compounds described herein, or pharmaceutically acceptable salts, solvates, or hydrates thereof, with other chemical components, such as physiologically acceptable carriers and excipients. The purpose of a pharmaceutical composition is to facilitate administration of a compound to an organism or subject.

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, ammonium or tetrafluoroborate. Exemplary pharmaceutically acceptable salts are found, for example, in Berge, et al. (*J. Pharm. Sci.* 1977, 66(1), 1; hereby incorporated by reference in its entirety).

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington's Pharmaceutical Sciences (Alfonso Gennaro ed., Krieger Publishing Company (1997); Remington's: The Science and Practice of Pharmacy, 21$^{st}$ Ed. (Lippincot, Williams & Wilkins (2005); Modern Pharmaceutics, vol. 121 (Gilbert Banker and Christopher Rhodes, CRC Press (2002); each of which hereby incorporated by reference in its entirety.

PDE5 inhibitors are described, for example, in U.S. Pat. Nos. 5,250,534; 5,859,006; 6,362,178; and 7,378,430; International Patent Publication Nos. WO/2008/095835, WO/2009/050554, WO/2009/124119, WO/2010/015589, WO/2010/074783, and WO/2011/015523; and Uthayathas et al in *Pharmacol. Rep.* 2007, 59(2), 150-63; and references cited therein; each of which is hereby incorporated by reference in its entirety. PDE5 inhibitors include, for example, sildenafil, tadalafil, vardenafil, avanafil, lodenafil, udenafil, mirodenafil, P20066 (Ethypharm), SLx-2101 (Kadmon Pharmaceuticals), PF00489791 (Pfizer), INT007 (IntelGenx Technologies), and dasantafil. A novel family of PDE5 inhibitors has been discovered and is described herein.

Benzonaphthyridine derivatives are described, for example, in U.S. Pat. Nos. 3,674,790; 4,742,061; 6,294,547; 6,384,047; 6,436,952; and International Patent Publication No. WO/1998/055481; each of which is hereby incorporated by reference in its entirety. Herein, the inventors describe compounds that are novel benzonaphthyridine derivatives. In some embodiments, the compounds inhibit PDE5.

In some embodiments, A is O. In some embodiments, A is $NR^4$. In some embodiments, A is N—$(C_1$-$C_3)$-alkyl. In some embodiments, A is N-methyl. In some embodiments, A is NH.

In some embodiments, X is —$(C_1$-$C_3)$-alkyl. In some embodiments, X is —$(C_1$-$C_2)$-alkyl. In some embodiments, X is $CH_2$.

In some embodiments, V is a bond. In some embodiments, V is C(O).

In some embodiments, W is a bond. In some embodiments, W is $NR^{13}$.

In some embodiments, $R^1$ is hydrogen or halogen. In some embodiments, $R^1$ is hydrogen, halogen or —$(C_1$-$C_3)$-haloalkyl. In some embodiments, $R^1$ is halogen or —$(C_1$-$C_6)$-haloalkyl. In some embodiments, $R^1$ is halogen or —$(C_1$-$C_3)$-haloalkyl. In some embodiments, $R^1$ is halogen. In some embodiments, $R^1$ is fluorine, chlorine or bromine. In some embodiments, $R^1$ is chlorine or bromine. In some embodiments, $R^1$ is chlorine. In some embodiments, $R^1$ is —$(C_1$-$C_3)$-haloalkyl. In some embodiments, $R^1$ is trifluoromethyl.

In some embodiments, $R^2$ is $OR^6$. In some embodiments, $R^2$ is —O—$(C_1$-$C_3)$-alkyl. In some embodiments, $R^2$ is —O-methyl or —O-ethyl. In some embodiments, $R^2$ is —O-methyl. In some embodiments, $R^2$ is hydrogen.

In some embodiments, $R^3$ is hydrogen, —OMe, —$CF_3$, —CN or halogen. In some embodiments, $R^3$ is CN. In some embodiments, $R^3$ is halogen. In some embodiments, $R^3$ is fluorine, chlorine or bromine. In some embodiments, $R^3$ is fluorine. In some embodiments, $R^3$ is chlorine. In some embodiments, $R^3$ is bromine. In some embodiments, $R^3$ is hydrogen. In other embodiments, $R^3$ is —OMe. In some embodiments, $R^3$ is —$CF_3$.

In some embodiments, $R^5$ is hydrogen, —$(C_1$-$C_3)$-alkyl, or —$(C_3$-$C_5)$-cycloalkyl. In some embodiments, $R^5$ is hydrogen or —$(C_1$-$C_3)$-alkyl. In some embodiments, $R^5$ is —$(C_1$-$C_3)$-alkyl or —$(C_3$-$C_5)$-cycloalkyl. In some embodiments, $R^5$ is hydrogen. In some embodiments, $R^5$ is —$(C_1$-$C_3)$-alkyl. In some embodiments, $R^5$ is methyl or ethyl. In some embodiments, $R^5$ is methyl. In some embodiments, $R^5$ is ethyl. In some embodiments, $R^5$ is —$(C_3$-$C_5)$-cycloalkyl. In some embodiments, $R^5$ is cyclopropyl or cyclobutyl. In some embodiments, $R^5$ is cyclopropyl.

In some embodiments, $R^6$ is hydrogen, —$(C_1$-$C_6)$-alkyl, —$(C_1$-$C_6)$-haloalkyl, or —$(C_3$-$C_8)$-cycloalkyl. In some embodiments, $R^6$ is hydrogen, —$(C_1$-$C_6)$-alkyl, or —$(C_1$-$C_6)$-haloalkyl. In some embodiments, $R^6$ is hydrogen, —$(C_1$-$C_3)$-alkyl, or —$(C_1$-$C_3)$-haloalkyl. In some embodiments, $R^6$ is hydrogen, or —$(C_1$-$C_3)$-alkyl. In some embodiments, $R^6$ is —$(C_1$-$C_3)$-alkyl.

In some embodiments, $R^7$ is independently hydrogen, —$(C_1$-$C_6)$-alkyl, —$(C_1$-$C_6)$-haloalkyl, or aryl. In some embodiments, $R^7$ is independently hydrogen, —$(C_1$-$C_6)$-alkyl, or —$(C_1$-$C_6)$-haloalkyl. In some embodiments, $R^7$ is independently hydrogen or —$(C_1$-$C_6)$-alkyl.

In some embodiments, $R^8$ is hydrogen, —$(C_1$-$C_6)$-alkyl, —$(C_1$-$C_6)$-haloalkyl, —$(C_3$-$C_8)$-cycloalkyl, —$NR^9R^{10}$, —$S(O)_2R^{11}$, or heterocyclyl. In some embodiments, $R^8$ is hydrogen, —$(C_1$-$C_6)$-alkyl, —$(C_1$-$C_6)$-haloalkyl, —$(C_3$-$C_8)$-cycloalkyl, or —$NR^9R^{10}$. In some embodiments, $R^8$ is hydrogen, —$(C_1$-$C_6)$-alkyl, —$(C_1$-$C_6)$-haloalkyl, or —$(C_3$-$C_8)$-cycloalkyl. In some embodiments, $R^8$ is hydrogen, —$(C_1$-$C_6)$-alkyl, or —$(C_3$-$C_8)$-cycloalkyl. In some embodiments, $R^8$ is hydrogen or —$(C_1$-$C_6)$-alkyl. In some embodiments, $R^8$ is hydrogen or —$(C_1$-$C_3)$-alkyl. In some embodiments, $R^8$ is hydrogen or —($C_1$-$C_2$)-alkyl. In some embodiments, $R^8$ is hydrogen or ethyl. In some embodiments, $R^8$ is hydrogen.

In some embodiments, $R^9$ and $R^{10}$ are each independently hydrogen, —($C_1$-$C_6$)-alkyl, —($C_3$-$C_8$)-cycloalkyl, or $C(O)R^{11}$, wherein the —($C_1$-$C_6$)-alkyl or —($C_3$-$C_8$)-cycloalkyl are optionally substituted with —($C_1$-$C_6$)-alkyl, —($C_3$-$C_8$)-cycloalkyl, —$NR^{11}R^{12}$, —$S^{11}$, or heterocyclyl. In some embodiments, $R^9$ and $R^{10}$ are each independently hydrogen, —($C_1$-$C_6$)-alkyl, or —($C_3$-$C_8$)-cycloalkyl. In some embodiments, $R^9$ and $R^{10}$ are each independently hydrogen, —($C_1$-$C_6$)-alkyl, or —($C_3$-$C_8$)-cycloalkyl. In some embodiments, $R^9$ and $R^{10}$ are each independently hydrogen, or —($C_1$-$C_6$)-alkyl. In some embodiments, $R^9$ and $R^{10}$ are independently —($C_1$-$C_3$)-alkyl, or —($C_3$-$C_8$)-cycloalkyl.

In some embodiments, $R^9$ and $R^{10}$ together with the nitrogen atom to which they are attached form a 3 to 8-membered heterocycle, wherein any one of the ring carbon atoms is optionally replaced with a heteroatom, and wherein the heterocycle is optionally substituted with —($C_1$-$C_6$)-alkyl.

In some embodiments, $R^{13}$ is hydrogen, —($C_1$-$C_6$)-alkyl, —($C_3$-$C_5$)-cycloalkyl, —$C(O)R^7$, —$C(O)OR^7$, —$C(O)N(R^7)_2$, —$S(O)_2R^7$. In some embodiments, $R^{13}$ is hydrogen, —($C_1$-$C_3$)-alkyl, —($C_3$-$C_5$)-cycloalkyl, —$C(O)R^7$, —$C(O)OR^7$, —$C(O)N(R^7)_2$, or —$S(O)_2R^7$. In some embodiments, $R^{13}$ is hydrogen, —($C_1$-$C_3$)-alkyl, or —($C_3$-$C_5$)-cycloalkyl. In some embodiments, $R^{13}$ is hydrogen, or —($C_3$-$C_5$)-cycloalkyl. In some embodiments, $R^{13}$ is hydrogen, or —($C_1$-$C_3$)-alkyl. In some embodiments, $R^{13}$ is hydrogen, —($C_1$-$C_3$)-alkyl or cyclopropyl. In some embodiments, $R^{13}$ is hydrogen or —($C_1$-$C_3$)-alkyl. In some embodiments, $R^{13}$ is hydrogen or cyclopropyl. In some embodiments, $R^{13}$ is hydrogen. In some embodiments, $R^{13}$ is —($C_1$-$C_3$)-alkyl or cyclopropyl. In some embodiments, $R^{13}$ is hydrogen. In some embodiments, $R^{13}$ is —($C_1$-$C_3$)-alkyl. In some embodiments, $R^{13}$ is ethyl. In some embodiments, $R^{13}$ is cyclopropyl.

In some embodiments, m is 0, 1 or 2. In some embodiments, m is 0 or 1. In some embodiments, m is 1 or 2. In some embodiments, m is 0. In some embodiments, m is 1. In some embodiments, m is 2.

In some embodiments, n is 0, 1 or 2. In some embodiments, n is 0 or 1. In some embodiments, n is 1 or 2. In some embodiments, n is 0. In some embodiments, n is 1. In some embodiments, n is 2.

In some embodiments, m is 1 and n is 1. In some embodiments, m is 2 and n is 1. In some embodiments, m is 1 and n is 2. In some embodiments, m is 0 and n is 1. In some embodiments, m is 0 and n is 2.

In some embodiments, Y is $NR^5$. In some embodiments, Y is O or S. In some embodiments, Y is NH.

In some embodiments, V is a bond, W is a bond, X is —($C_1$-$C_3$)-alkyl; Y is $NR^5$; and m and n are each 1 or 2.

In some embodiments, A is $NR^4$, V is a bond or $C(O)$, W is a bond or $NR^{13}$, X is —($C_1$-$C_3$)-alkyl; Y is $NR^5$; $R^1$ is halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, —($C_1$-$C_3$)-cycloalkyl, or $C(O)R^7$; $R^6$ is —($C_1$-$C_3$)-alkyl or —($C_1$-$C_3$)-haloalkyl; $R^7$ is —($C_1$-$C_3$)-alkyl; $R^8$ is hydrogen; $R^{13}$ is hydrogen or —($C_1$-$C_3$)-alkyl; m is 0 or 1; and n is 2, provided that the sum of m+n is an integer from 2-3.

In some embodiments, A is $NR^4$, V is a bond or $C(O)$, W is a bond or $NR^{13}$, X is —($C_1$-$C_3$)-alkyl; Y is $NR^5$; $R^1$ is halogen; $R^2$ is —$OR^6$; $R^3$ is hydrogen, —OMe, —CF3, CN or halogen; $R^5$ is hydrogen, —($C_1$-$C_3$)-alkyl, or $C(O)R^7$; $R^6$ is —($C_1$-$C_3$)-alkyl; $R^7$ is —($C_1$-$C_3$)-alkyl; $R^8$ is hydrogen; $R^{13}$ is hydrogen; m is 0 or 1; and n is 2, provided that the sum of m+n is an integer from 2-3.

In some embodiments, A is 0, V is a bond or $C(O)$, W is a bond or NH, X is —$CH_2$—; Y is $NR^5$; $R^1$ is halogen; $R^2$ is $OCH_3$; $R^3$ is hydrogen, —OMe, —CF3, —CN or halogen; $R^5$ is hydrogen, —($C_1$-$C_3$)-alkyl, or $C(O)CH_3$; $R^8$ is hydrogen; m is 0 or 1; and n is 2, provided that the sum of m+n is an integer from 2-3.

In some embodiments, X is $CH_2$; Y is $NR^5$; $R^1$ is hydrogen, halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, or —($C_3$-$C_5$)-cycloalkyl; $R^6$ is hydrogen, —($C_1$-$C_3$)-alkyl, or —($C_1$-$C_3$)-haloalkyl; and $R^8$ is hydrogen, —($C_1$-$C_3$)-alkyl, or —($C_1$-$C_3$)-haloalkyl.

In some embodiments, V is a bond, W is a bond, X is $CH_2$; Y is $NR^5$; $R^1$ is hydrogen, halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, or —($C_3$-$C_5$)-cycloalkyl; $R^6$ is hydrogen, —($C_1$-$C_3$)-alkyl, or —($C_1$-$C_3$)-haloalkyl; and $R^8$ is hydrogen, —($C_1$-$C_3$)-alkyl, or —($C_1$-$C_3$)-haloalkyl.

In some embodiments, X is $CH_2$; Y is $NR^5$; $R^1$ is hydrogen, halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, or —($C_3$-$C_5$)-cycloalkyl; $R^6$ is hydrogen, —($C_1$-$C_3$)-alkyl, or —($C_1$-$C_3$)-haloalkyl; $R^6$ is hydrogen, —($C_1$-$C_3$)-alkyl, or —($C_1$-$C_3$)-haloalkyl; $R^8$ is hydrogen, —($C_1$-$C_3$)-alkyl, or —($C_1$-$C_3$)-haloalkyl; and m and n are each 1 or 2.

In some embodiments, V is a bond, W is a bond, X is $CH_2$; Y is $NR^5$; $R^1$ is hydrogen, halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, or —($C_3$-$C_5$)-cycloalkyl; $R^6$ is hydrogen, —($C_1$-$C_3$)-alkyl, or —($C_1$-$C_3$)-haloalkyl; $R^6$ is hydrogen, —($C_1$-$C_3$)-alkyl, or —($C_1$-$C_3$)-haloalkyl; $R^8$ is hydrogen, —($C_1$-$C_3$)-alkyl, or —($C_1$-$C_3$)-haloalkyl; and m and n are each 1 or 2.

In some embodiments, V is a bond, W is a bond, A is NH; X is $CH_2$; Y is $NR^5$; $R^1$ is halogen or —($C_1$-$C_3$)-haloalkyl; $R^2$ is —$OR^6$; $R^3$ is hydrogen, —OMe, —CF3, —CN or halogen; $R^5$ is hydrogen or —($C_1$-$C_3$)-alkyl; and $R^6$ is hydrogen, —($C_1$-$C_2$)-alkyl, or —($C_1$-$C_2$)-haloalkyl.

In some embodiments, A is NH; X is $CH_2$; Y is $NR^5$; $R^1$ is halogen or —($C_1$-$C_3$)-haloalkyl; $R^2$ is —$OR^6$; $R^3$ is hydrogen, —OMe, —CF3, —CN or halogen; $R^5$ is hydrogen or —($C_1$-$C_3$)-alkyl; and $R^6$ is hydrogen, —($C_1$-$C_2$)-alkyl, or —($C_1$-$C_2$)-haloalkyl.

In some embodiments, A is NH; X is $CH_2$; Y is $NR^5$; $R^1$ is halogen or —($C_1$-$C_3$)-haloalkyl; $R^2$ is —$OR^6$; $R^3$ is hydrogen, —OMe, —CF3, —CN or halogen; $R^5$ is hydrogen or —($C_1$-$C_3$)-alkyl; $R^6$ is hydrogen, —($C_1$-$C_2$)-alkyl, or —($C_1$-$C_2$)-haloalkyl; m is 1; and n is 2.

In some embodiments, A is NH; X is $CH_2$; Y is $NR^5$; $R^1$ is halogen; $R^2$ is —$OCH_3$; $R^3$ is hydrogen, —OMe, —CF3, —CN or halogen; $R^5$ is hydrogen or —($C_1$-$C_3$)-alkyl; m is 1; and n is 2.

In some embodiments, $R^1$ and $R^2$ are not both hydrogen when V and W are each a bond, Y is $NR^5$, A is $NR^4$, X is CO, n=2 and m=1.

In some embodiments, A is $NR^4$; V is a bond or $C(O)$; W is a bond or $NR^{13}$; X is —($C_1$-$C_3$)-alkyl; Y is $NR^5$; $R^1$ is halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, —($C_1$-$C_3$)-cycloalkyl, or —$C(O)R^7$; $R^6$ is —($C_1$-$C_3$)-alkyl or —($C_1$-$C_3$)-haloalkyl; $R^7$ is —($C_1$-$C_3$)-alkyl; $R^8$ is hydrogen or —($C_1$-$C_3$)-alkyl; $R^{13}$ is hydrogen or —($C_1$-$C_3$)-alkyl; and m and n are independently 0, 1 or 2, provided that the sum of m+n is an integer from 2-3.

In some embodiments, A is NH; V is a bond or C(O); W is a bond or $NR^{13}$; X is —($C_1$-$C_3$)-alkyl; Y is $NR^5$; $R^1$ is halogen; $R^2$ is —$OR^6$; $R^3$ is hydrogen, —OMe, —CF3, —CN or halogen; $R^5$ is hydrogen, —($C_1$-$C_3$)-alkyl, or —C(O)$R^7$; $R^6$ is —($C_1$-$C_3$)-alkyl; $R^7$ is —($C_1$-$C_3$)-alkyl; $R^8$ is hydrogen or —($C_1$-$C_3$)-alkyl; $R^{13}$ is hydrogen; m is 0 or 1; and n is 2.

In some embodiments, A is NH; V is a bond or C(O); W is a bond or NH; X is —$CH_2$—; Y is $NR^5$; $R^1$ is halogen; $R^2$ is —$OCH_3$; $R^3$ is hydrogen, —OMe, —CF3, —CN or halogen; $R^5$ is hydrogen, —($C_1$-$C_3$)-alkyl, or —C(O)$CH_3$; $R^8$ is hydrogen or —($C_1$-$C_3$)-alkyl; m is 0 or 1; and n is 2.

In some embodiments, V and W are each a bond, or V is C(O) and W is $NR^{13}$; X is —($C_1$-$C_3$)-alkyl; Y is $NR^5$; and m and n are each 0, 1 or 2, provided that the sum of m+n is an integer from 2-3.

In some embodiments, A is NH; V is C(O); W is NH; X is $CH_2$; Y is $NR^5$; $R^1$ is halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, or C(O)$R^7$; $R^6$ is hydrogen, —($C_1$-$C_3$)-alkyl, or —($C_1$-$C_3$)-haloalkyl; $R^7$ is hydrogen or —($C_1$-$C_3$)-alkyl; $R^8$ is hydrogen, —($C_1$-$C_3$)-alkyl, —($C_1$-$C_3$)-haloalkyl, —($C_3$-$C_5$)-cycloalkyl, —$NR^9R^{10}$; m is 0 or 1; and n is 2.

In some embodiments, A is NH; V is C(O); W is NH; X is $CH_2$; Y is $NR^5$; $R^1$ is halogen; $R^2$ is —$OCH_3$; $R^3$ is hydrogen, —OMe, —CF3, —CN or halogen; $R^5$ is hydrogen, —($C_1$-$C_3$)-alkyl, or C(O)$R^7$; $R^7$ is —($C_1$-$C_3$)-alkyl; $R^8$ is hydrogen or —($C_1$-$C_3$)-alkyl; m is 0; and n is 2.

In some embodiments, A is NH; V and W are each a bond, or V is C(O) and W is NH; X is $CH_2$; Y is $NR^5$; $R^1$ is halogen or —($C_1$-$C_3$)-haloalkyl; $R^2$ is —$OR^6$; $R^3$ is hydrogen, —OMe, —CF3, —CN or halogen; $R^5$ is hydrogen, —($C_1$-$C_3$)-alkyl, or C(O)$R^7$; $R^6$ is hydrogen, —($C_1$-$C_2$)-alkyl, or —($C_1$-$C_2$)-haloalkyl; $R^7$ is —($C_1$-$C_3$)-alkyl; $R^8$ is hydrogen, —($C_1$-$C_3$)-alkyl, —($C_1$-$C_3$)-haloalkyl, or —($C_3$-$C_5$)-cycloalkyl; m is 0 or 1; and n is 2.

In some embodiments, A is NH; V and W are each a bond; X is $CH_2$; Y is $NR^5$; $R^1$ is chlorine; $R^2$ is —$OCH_3$; $R^3$ is —CN; $R^5$ is hydrogen or —($C_1$-$C_3$)-alkyl; $R^8$ is hydrogen or —($C_1$-$C_3$)-alkyl; m is 1; and n is 2.

In some embodiments, A is NH; V and W are each a bond; X is $CH_2$; Y is NC(O)$CH_3$; $R^1$ is halogen; $R^2$ is —$OCH_3$; $R^3$ is hydrogen, —OMe, —CF3, —CN or halogen; $R^8$ is hydrogen; m is 1; and n is 2.

In another aspect, the invention is directed to compositions comprising a compound of formula (I), (Ia), (Ib), or (Ic) and a pharmaceutically acceptable carrier.

In another aspect, the invention is directed to a method of inhibiting phosphodiesterase comprising contacting a phosphodiesterase with a compound of formula (I), (Ia), (Ib), or (Ic) or a composition comprising a compound of formula (I), (Ia), (Ib), or (Ic). In some embodiments, the phosphodiesterase is PDE5.

In another aspect, the invention is directed to a method of treating neurodegenerative disease in a subject comprising administration of a therapeutically effective amount of a compound of formula (I), (Ia), (Ib), or (Ic). In some embodiments, the disease is Alzheimer's Disease.

In another aspect, the invention is directed to a method of treating neurodegenerative disease in a subject comprising administration of a therapeutically effective amount of a composition comprising a compound of formula (I), (Ia), (Ib), or (Ic). In some embodiments, the disease is Alzheimer's Disease.

In another aspect, the invention is directed to a method of increasing long-term potentiation in a subject comprising administration of a therapeutically effective amount of a compound of formula (I), (Ia), (Ib), or (Ic). In some embodiments, the subject has a neurodegenerative disease. In some embodiments, the neurodegenerative disease is Alzheimer's Disease.

In another aspect, the invention is directed to a method of increasing long-term potentiation in a subject comprising administration of a therapeutically effective amount of a composition comprising a compound of formula (I), (Ia), (Ib), or (Ic). In some embodiments, the subject has a neurodegenerative disease. In some embodiments, the neurodegenerative disease is Alzheimer's Disease.

In another aspect, the invention is directed to a method of improving memory in a subject comprising administration of a therapeutically effective amount of a compound of formula (I), (Ia), (Ib), or (Ic). In some embodiments, the subject has a neurodegenerative disease. In some embodiments, the neurodegenerative disease is Alzheimer's Disease.

In another aspect, the invention is directed to a method of improving memory in a subject comprising administration of a therapeutically effective amount of a composition comprising a compound of formula (I), (Ia), (Ib), or (Ic). In some embodiments, the subject has a neurodegenerative disease. In some embodiments, the neurodegenerative disease is Alzheimer's Disease.

In another aspect, the invention is directed to a method of improving synaptic function in a subject comprising administration of a therapeutically effective amount of a compound of formula (I), (Ia), (Ib), or (Ic). In some embodiments, synaptic function comprises synaptic plasticity. In some embodiments, synaptic plasticity comprises learning, memory, or a combination thereof. In some embodiments, synaptic plasticity comprises long term potentiation (LTP). In some embodiments, the subject has a neurodegenerative disease. In some embodiments, the neurodegenerative disease is Alzheimer's Disease.

In another aspect, the invention is directed to a method of improving synaptic function in a subject comprising administration of a therapeutically effective amount of a composition comprising a compound of formula (I), (Ia), (Ib), or (Ic). In some embodiments, synaptic function comprises synaptic plasticity. In some embodiments, synaptic plasticity comprises learning, memory, or a combination thereof. In some embodiments, synaptic plasticity comprises long term potentiation (LTP). In some embodiments, the subject has a neurodegenerative disease. In some embodiments, the neurodegenerative disease is Alzheimer's Disease.

Another aspect of the invention provides a method for increasing memory retention in a subject afflicted with a neurodegenerative disease, the method comprising administering to a subject a therapeutic amount of a compound of formula (I), (Ia), (Ib), or (Ic) or a composition comprising a compound of formula (I), (Ia), (Ib), or (Ic).

In some embodiments, a compound of formula (I), (Ia), (Ib), or (Ic) is administered. In some embodiments, a composition comprising a compound of formula (I), (Ia), (Ib), or (Ic) is administered.

Exemplary neurodegenerative diseases and methods of treatment therefor are also described in WO 2010/074783, WO2011/072243, and WO2012/088420, each herein incorporated by reference in its entirety.

Compounds of formula (I), (Ia), (Ib), or (Ic) can be incorporated into pharmaceutical compositions suitable for administration. Such compositions can comprise a compound of formula (I), (Ia), (Ib), or (Ic) and a pharmaceutically acceptable carrier. Thus, in some embodiments, the compounds of the invention are present in a pharmaceutical composition.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat or human. In some embodiments, the subject is a mouse. In some embodiments, the subject is a rat. In some embodiments, the subject is a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the PDE5 inhibitor compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Benzonaphthyridine derivatives are synthesized by methods within the purview of the ordinarily skilled artisan. Exemplary methods by which benzonaphthyridine derivatives can be synthesized are as follows.

Method A: Benzonaphthyridine derivatives can be synthesized, for example, starting from 2-aminobenzoic acid derivative (Scheme 1).

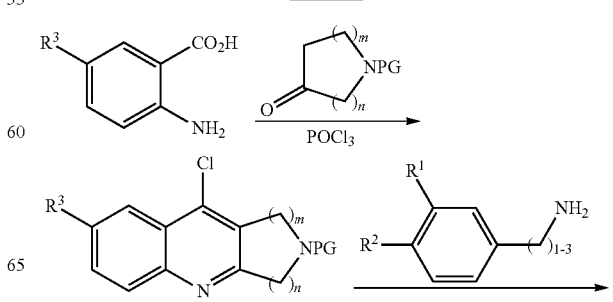

Scheme 1

-continued

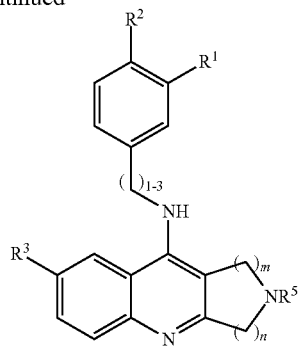

A mixture of 2-aminobenzoic acid derivative and cyclic amino ketone derivative (optionally containing an alkyl group or other protecting group at the nitrogen atom) can be heated in, for example, POCl$_3$ to obtain a benzonaphthyridine. Re-installation of the protecting group (if it is removed during benzonaphthyridine formation) can be achieved by known methods such as those described in, for example, Protecting Groups in Organic Synthesis, 4$^{th}$ Edition, by Peter Wuts & Theodora Greene (Wiley 2006), hereby incorporated by reference in its entirety. Subsequent treatment with a phenylalkylamine and a salt such as, for example, a sodium halide, in a solvent such as a phenol can be heated to obtain the elaborated benzonphthyridine derivative. Optional protection of the nitrogen atom of the phenylalkylamine can be achieved by known methods, such as those described in, for example, Protecting Groups in Organic Synthesis, 4$^{th}$ Edition, by Peter Wuts & Theodora Greene (Wiley 2006), hereby incorporated by reference in its entirety. The skilled artisan will recognize selection of an appropriate protecting group based on desired properties and orthogonality with other protecting groups at, for example, the piperidine nitrogen atom. Optional deprotection of the piperidine nitrogen can be achieved by known methods, such as those described in, for example, Protecting Groups in Organic Synthesis, 4$^{th}$ Edition, by Peter Wuts & Theodora Greene (Wiley 2006) (hereby incorporated by reference in its entirety), followed by incorporation of the desired R$^5$ group via reductive amination of an R$^5$—CHO in the presence of a reducing agent such as a borohydride or via alkylation of R$^5$-LG (wherein LG is a leaving group such as, for example, halogen, sulfonate, etc.). Removal of protecting groups can be achieved by known methods, such as those described in, for example, Protecting Groups in Organic Synthesis, 4$^{th}$ Edition, by Peter Wuts & Theodora Greene (Wiley 2006) (hereby incorporated by reference in its entirety).

Method B: Benzonaphthyridine derivatives can be synthesized, for example, starting from 2-aminobenzoic acid derivative (Scheme 2).

Scheme 2:

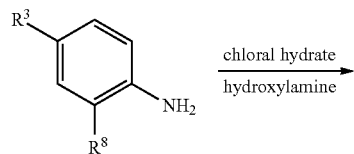

-continued

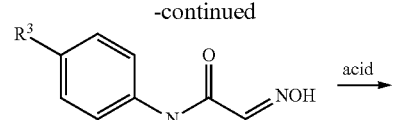

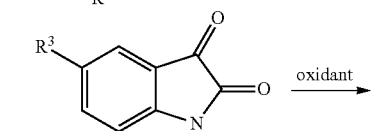

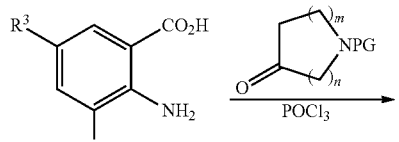

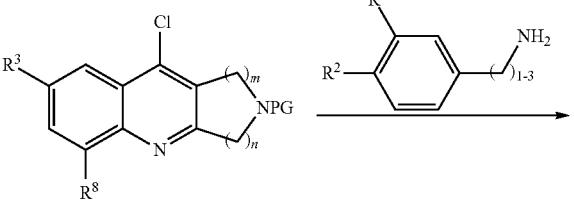

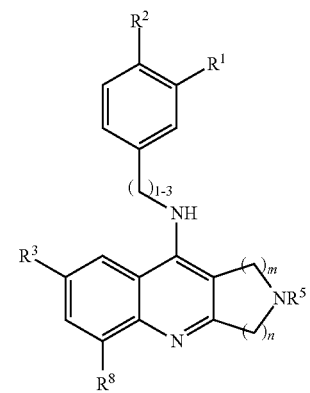

An aniline derivative in a solvent such as water can be treated with chloral hydrate, acid (such as HCl), a group I sulfate (such as sodium sulfate), hydroxylamine and heated to generate a hydroxyl-imine. The hydroxyl-imine can be treated with an acid (such as sulfuric acid) and heated to generate an indoline-2,3-dione. Subsequent treatment with an oxidant such as hydrogen peroxide in a base such as sodium hydroxide can generate a 2-aminobenzoic acid. Optional conversion of R$^3$ to —CN can be achieved via treatment with copper cyanide in a solvent such as NMP prior to further processing.

The 2-aminobenzoic acid derivative and cyclic amino ketone derivative (optionally containing an alkyl group or other protecting group at the nitrogen atom) can be heated in POCl$_3$ to obtain a benzonaphthyridine. Re-installation of the protecting group (if it is removed during benzonaphthyridine formation) can be achieved by known methods such as those described in, for example, Protecting Groups in Organic Synthesis, 4$^{th}$ Edition, by Peter Wuts & Theodora Greene (Wiley 2006), hereby incorporated by reference in its entirety. Subsequent treatment with a phenylalkylamine and a salt such as, for example, a sodium halide, in a solvent such as a phenol can be heated to obtain the elaborated benzonphthyridine derivative. Optional protection of the nitrogen atom of the phenylalkylamine can be achieved by known methods, such as those described in, for example, Protecting Groups in Organic Synthesis, 4th Edition, by Peter Wuts & Theodora Greene (Wiley 2006), hereby incorporated by reference in its entirety. The skilled artisan will recognize selection of an appropriate protecting group based on desired properties and orthogonality with other protecting groups at, for example, the piperidine nitrogen atom. Optional deprotection of the piperidine nitrogen can be achieved by known methods, such as those described in, for example, Protecting Groups in Organic Synthesis, 4th Edition, by Peter Wuts & Theodora Greene (Wiley 2006) (hereby incorporated by reference in its entirety), followed by incorporation of the desired $R^5$ group via reductive amination of an $R^5$—CHO in the presence of a reducing agent such as a borohydride or via alkylation of $R^5$-LG (wherein LG is a leaving group such as, for example, halogen, sulfonate, etc.). Removal of protecting groups can be achieved by known methods, such as those described in, for example, Protecting Groups in Organic Synthesis, 4th Edition, by Peter Wuts & Theodora Greene (Wiley 2006) (hereby incorporated by reference in its entirety).

Method C: Benzonaphthyridine derivatives can also be synthesized, for example, starting from 2-aminobenzonitrile derivative (Scheme 3).

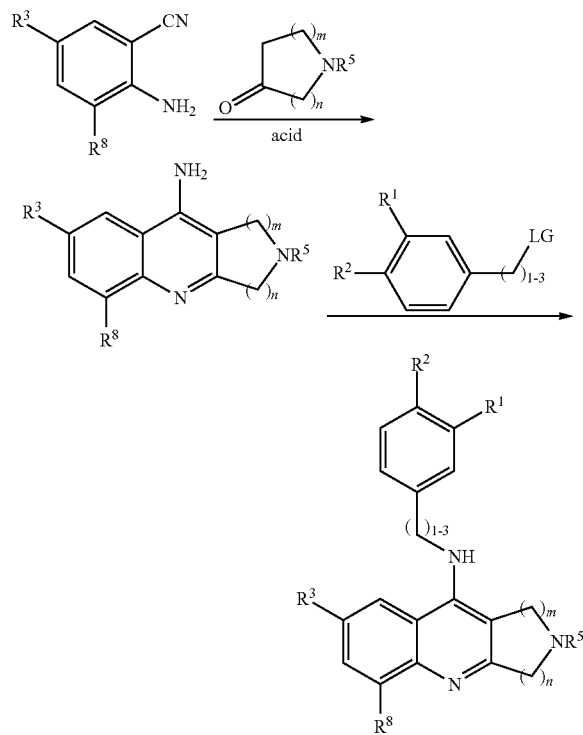

A mixture of 2-aminobenzonitrile derivative and cyclic amino ketone derivative can be heated in the presence of a strong acid. Strong acids employed in this transformation can be any organic or inorganic acid, such as, for example, polyphosphoric, trifluoroacetic, acetic, and sulfonic acid. Subsequent treatment with a phenylalkyl moiety containing a leaving group (LG) and a base such as, for example, a trialkylamine, can form the elaborated benzonphthyridine derivative.

In addition to the aforementioned general methods, other methods such as those described in, for example, U.S. Pat. Nos. 3,674,790 and 6,294,547 (each herein incorporated by reference in its entirety) can also be used to obtain the benzonaphthyridine derivatives. The ordinarily skilled artisan will recognize variations of the methods described herein and of the methods described in the references herein cited to synthesize other benzonaphthyridine derivatives within the scope of the invention.

A PDE5 inhibitor can decrease the activity of a PDE5 molecule in vivo and/or in vitro. In one embodiment, a PDE5 inhibitor can decrease PDE5 activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

In some embodiments, the compounds of the invention exhibit inhibition of PDE5 with an IC50 less than about 1 µM. In some embodiments, the compounds of the invention exhibit inhibition of PDE5 with an IC50 less than about 500 nM. In some embodiments, the IC50 is less than about 250 nM, less than about 100 nM, less than about 50 nM, less than about 25 nM, less than about 10 nM, less than about 5 nM, or less than about 1 nM.

In some embodiments, the compounds of formula (I), (Ia), (Ib), or (Ic) are selective inhibitors of PDE5. In some embodiments, the compounds exhibit inhibition of PDE5 at lower concentrations than they inhibit other PDE subtypes. In some embodiments, other PDE subtypes may include any of PDE1-PDE4, and PDE6-PDE11 or any combination thereof. In some embodiments, the other PDE subtype is PDE1. In some embodiments, the other PDE subtype is PDE6. In some embodiments, the other PDE subtype is PDE9.

It will recognized that one or more features of any embodiments disclosed herein may be combined and/or rearranged within the scope of the invention to produce further embodiments that are also within the scope of the invention. Those skilled in the art will recognize, or be able to ascertain using no more than routine experimentation, many equivalents to the specific embodiments of the invention described herein. Such equivalents are intended to be within the scope of the present invention.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

8-bromo-N-(3-chloro-4-methoxybenzyl)-2-methyl-1,2,3,4-tetrahydrobenzo[b][1,6]naphthyridin-10-amine

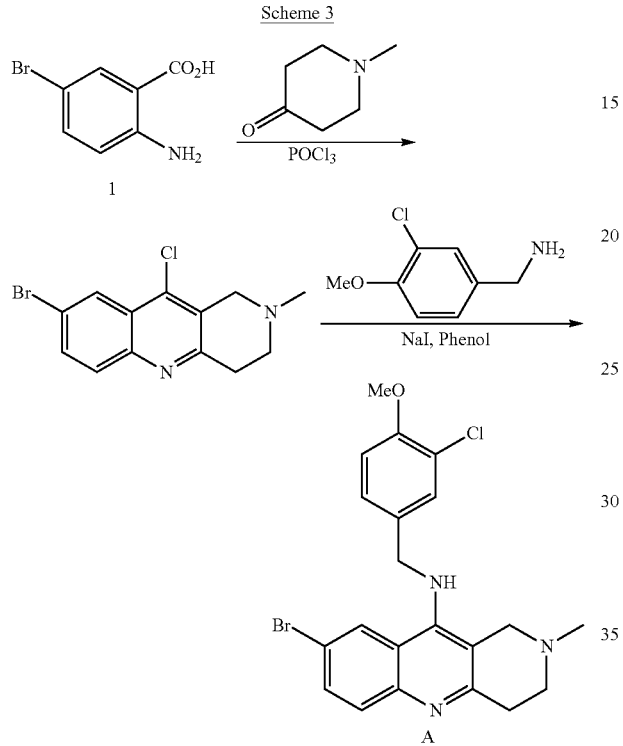

8-bromo-10-chloro-2-methyl-1,2,3,4-tetrahydrobenzo[b][1,6]naphthyridine, 2

A mixture of 1 (9.25 mmol) and 1-methylpiperidin-4-one (9.25 mmol) in POCl$_3$ (10 mL) was heated at 60° C. for 6 h. The excess POCl$_3$ was evaporated off; the residue was treated with iced H$_2$O and NaHCO$_3$ and extracted with AcOEt (3×50 mL). The organic layer was dried over Na$_2$SO$_4$, filtered and evaporated under reduced pressure. The desired compound was purified by triturating with Et$_2$O (42% of yield). $^1$H NMR (300 MHz, CDCl$_3$) δ 8.33 (d, 1H, J=2.1 Hz), 7.86 (d, 1H, J=9.0 Hz), 7.77 (dd, 1H, J$_1$=2.1, J$_2$=9.0 Hz), 3.99 (s, 2H), 3.34 (t, 2H, J=5.7 Hz), 3.03 (t, 2H, J=5.7 Hz), 2.69 (s, 3H).

A mixture of 2 (1.92 mmol), 3-chloro-4-methoxybenzylamine hydrochloride (2.11 mmol), NaI (0.1 mmol), and phenol (3.84 mmol) was heated at 130° C. for 1.5 h. After cooling the reaction down, Et$_2$O (20 mL) was added and washed with 1N NaOH (3×20 mL). The organic layer was dried over Na$_2$SO$_4$, filtered and evaporated under reduced pressure. The residue was purified by Flash Chromatography (AcOEt: MeOH 8:2) to give the desired compound A (38% yield). $^1$H NMR (300 MHz, CDCl$_3$) δ 8.04 (d, 1H, J=2.1 Hz), 7.80 (d, 1H, J=8.7 Hz), 7.64 (dd, 1H, J$_1$=2.1, J$_2$=9.0 Hz), 7.38 (d, 1H, J=2.1 Hz), 7.16 (dd, 1H, J$_1$=2.1, J$_2$=8.4 Hz), 6.91 (d, 1H, J=8.4 Hz), 4.47 (d, 2H, J=5.7 Hz), 3.91 (s, 3H), 3.54 (s, 2H), 3.18 (t, 2H, J=6.3 Hz), 2.81 (t, 2H, J=6.3 Hz), 2.50 (s, 3H).

Example 2

10-[(3-chloro-4-methoxybenzyl)amino]-2-methyl-1,2,3,4-tetrahydrobenzo[b][1,6]naphthyridine-8-carbonitrile

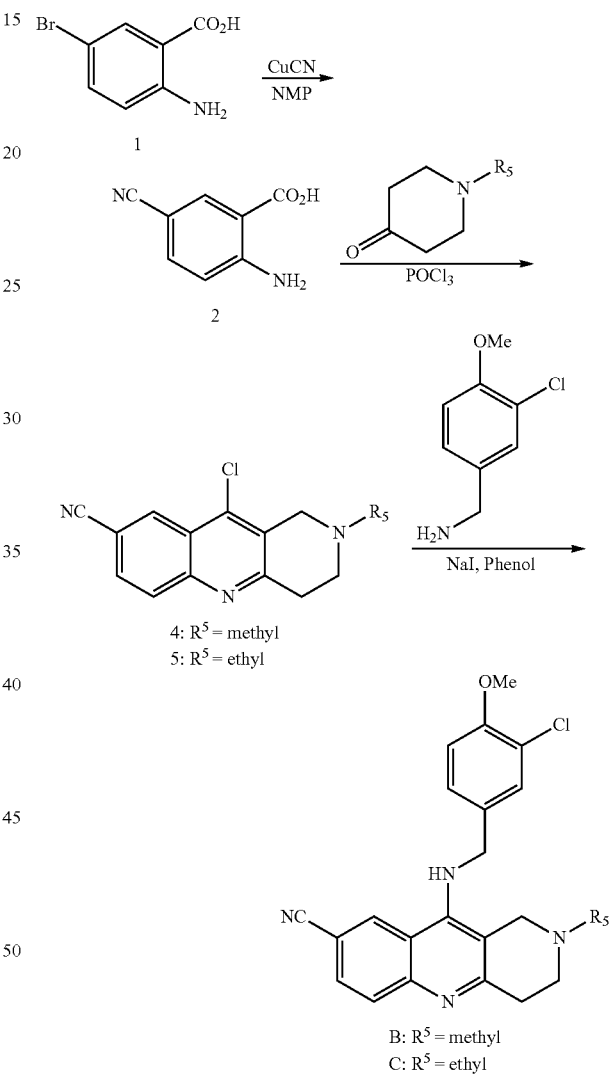

2-amino-5-cyanobenzoic acid, 3

2-amino-5-bromobenzoic acid (2.31 mmol) and CuCN (2.78 mmol) were heated to reflux in NMP (5 mL) for 3 h. The reaction mixture was poured into a solution of FeCl$_3$·3H$_2$O (3.0 g) in H$_2$O (3 mL) and HCl (0.5 mL) and stirred at 60° C. for 1 h. After cooling the reaction down, Et$_2$O (100 mL) was added and the two phases were separated. The organic layer was washed with HCl 1N (50 mL) and H$_2$O (2×50 mL), dried over Na$_2$SO$_4$, filtered and evaporated under reduced pressure. 2-amino-5-cyanobenzoic acid (3) was obtained (57% of yield) by triturating from $CH_2Cl_2$.

$^1$H NMR (300 MHz, $CDCl_3$) δ 8.32 (d, 1H, J=1.8 Hz), 7.71 (dd, 1H, $J_1$=1.8, $J_2$=8.7 Hz), 7.32 (br s, 1H), 6.75 (d, 1H, J=8.7 Hz).

10-chloro-2-methyl-1,2,3,4-tetrahydrobenzo[b][1,6]naphthyridine-8-carbonitrile, 4

A mixture of 1 (1.23 mmol) and 1-methylpiperidin-4-one (1.23 mmol) in $POCl_3$ (2 mL) was heated at 60° C. for 6 h. The excess $POCl_3$ was evaporated off; the residue was treated with iced $H_2O$ and $NaHCO_3$ and extracted with $CH_2Cl_2$ (3×25 mL). The organic layer was dried over $Na_2SO_4$, filtered and evaporated under reduced pressure. Purification by Flash Chromatography (5% MeOH in AcOEt) gave the desired compound (55% of yield). 1H NMR (300 MHz, $CDCl_3$) δ 8.58 (s, 1H), 8.07 (d, 1H, J=8.7 Hz), 7.83 (d, 1H, J=8.7 Hz), 3.85 (s, 2H), 3.30 (t, 2H, J=6.0 Hz), 2.89 (t, 2H, J=6.0 Hz), 2.60 (s, 3H).

10-chloro-2-ethyl-1,2,3,4-tetrahydrobenzo[b][1,6]naphthyridine-8-carbonitrile, 5

A mixture of 1 (1.23 mmol) and 1-ethylpiperidin-4-one (1.23 mmol) in $POCl_3$ (2 mL) was heated at 60° C. for 6 h. The excess $POCl_3$ was evaporated off; the residue was treated with iced $H_2O$ and $NaHCO_3$ and extracted with $CH_2Cl_2$ (3×25 mL). The organic layer was dried over $Na_2SO_4$, filtered and evaporated under reduced pressure. Purification by Flash Chromatography (5% MeOH in $CH_2Cl_2$) gave the desired compound (26% of yield). $^1$H NMR (300 MHz, $CDCl_3$) δ 8.58 (d, 1H, J=1.8 Hz), 8.06 (d, 1H, J=8.7 Hz), 7.82 (dd, 1H, $J_1$=1.8, $J_2$=8.4 Hz), 3.91 (s, 2H), 3.30 (t, 2H, J=5.7 Hz), 2.93 (t, 2H, J=5.7 Hz), 2.75 (q, 2H, J=7.2 Hz), 1.26 (t, 3H, J=7.2 Hz).

10-[(3-chloro-4-methoxybenzyl)amino]-2-methyl-1,2,3,4-tetrahydrobenzo[b][1,6]naphthyridine-8-carbonitrile A mixture of 4 (0.12 mmol), 3-chloro-4-methoxybenzylamine hydrochloride (0.12 mmol), NaI (0.006 mmol), and phenol (0.12 mmol) was heated at 130° C. for 2.5 h. The reaction mixture was diluted with $Et_2O$ (10 mL) and washed with 1N NaOH (3×5 mL). The organic layer was dried over $Na_2SO_4$, filtered and evaporated under reduced pressure. The residue was purified by Flash Chromatography (AcOEt:MeOH 8:2) to give the desired compound B (33% of yield). MS ESI (m/z) 394 (M+H)$^+$, $^1$H NMR (300 MHz, $CDCl_3$) δ 8.32 (d, 1H, J=1.2 Hz), 7.97 (d, 1H, J=8.7 Hz), 7.71 (dd, 1H, $J_1$=1.8, $J_2$=8.7 Hz), 7.37 (d, 1H, J=2.1 Hz), 7.18 (dd, 1H, $J_1$=2.4, $J_2$=8.7 Hz), 6.94 (d, 1H, J=8.4 Hz), 4.57 (d, 2H, J=6.0 Hz), 4.11 (br s, 1H), 3.92 (s, 3H), 3.54 (s, 2H), 3.22 (t, 2H, J=6.3 Hz), 2.83 (t, 2H, J=6.3 Hz), 2.52 (s, 3H).

Example 3

10-[(3-chloro-4-methoxybenzyl)amino]-2-ethyl-1,2,3,4-tetrahydrobenzo[b][1,6]naphthyridine-8-carbonitrile A mixture of 5 (0.18 mmol), 3-chloro-4-methoxybenzylamine hydrochloride (0.18 mmol), NaI (0.009 mmol), and phenol (0.18 mmol) was heated at 130° C. for 2.5 h (Scheme 4). The reaction mixture was diluted with $Et_2O$ (30 mL) and washed with 1N NaOH (3×1 mL). The organic layer was dried over $Na_2SO_4$, filtered and evaporated under reduced pressure. The residue was purified by Flash Chromatography (5% MeOH in AcOEt) to give the desired compound C (38% of yield). MS ESI (m/z) 407 (M+H)$^+$, $^1$H NMR (300 MHz, $CDCl_3$) δ 8.32 (d, 1H, J=1.2 Hz), 7.97 (d, 1H, J=8.7 Hz), 7.71 (dd, 1H, $J_1$=1.8, $J_2$=8.7 Hz), 7.37 (d, 1H, J=2.1 Hz), 7.17 (dd, 1H, $J_1$=2.1, $J_2$=8.4 Hz), 6.94 (d, 1H, J=8.4 Hz), 4.56 (d, 2H, J=5.7 Hz), 4.12 (br s, 1H), 3.92 (s, 3H), 3.59 (s, 2H), 3.22 (t, 2H, J=6.0 Hz), 2.87 (t, 2H, J=6.0 Hz), 2.66 (q, 2H, J=7.2 Hz), 1.18 (t, 3H, J=7.2 Hz).

Example 4

10-[(3-chloro-4-methoxybenzyl)amino]-6-ethyl-2-methyl-1,2,3,4-tetrahydrobenzo[b][1,6]naphthyridine-8-carbonitrile Scheme 5:

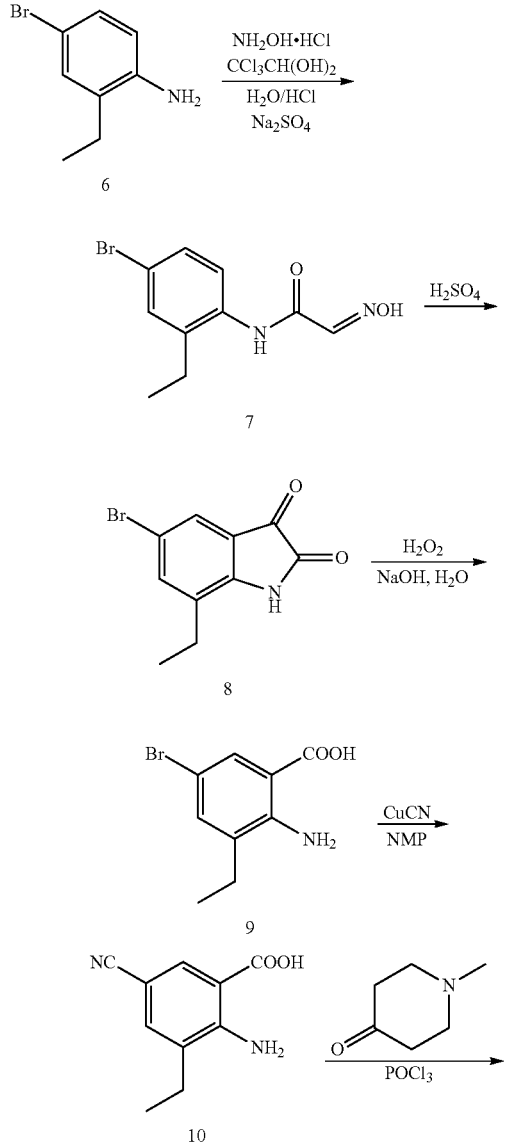

-continued

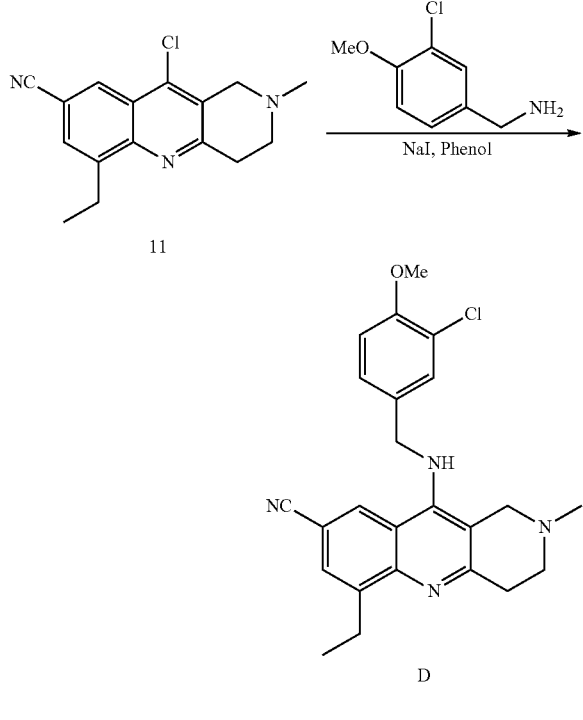

N-(4-bromo-2-ethylphenyl)-2-(hydroxyimino)acetamide, 7

To a suspension of 4-bromo-2-ethylaniline (6) (5.0 mmol) in 50 mL of $H_2O$ was added HCl conc. (0.5 mL), 4.4 g of $Na_2SO_4$, and $NH_2OH$ hydrochloride (14.9 mmol), followed by addition of chloral hydrate (5.5 mmol). The reaction mixture was heated to 90° C. for 1 h. After cooling down to room temperature, the aqueous phase was extracted with AcOEt (3×50 mL). The organic layers were dried over $Na_2SO_4$, filtered and evaporated to give compound 7. $^1H$ NMR (300 MHz, $CDCl_3$) δ 8.22 (br s, 1H), 7.93-7.90 (m, 2H), 7.60 (s, 1H), 7.37-7.34 (m, 2H), 2.60 (q, 2H, J=7.5 Hz), 1.25 (t, 3H, J=7.2 Hz).

5-bromo-7-ethylindoline-2,3-dione, 8

To a solution of sulfuric acid (10 mL) and $H_2O$ (1 mL) at 80° C. was added 7 (3.68 mmol) in small portions over 20 minutes. The reaction mixture was stirred for 15 min at 80° C. After cooling the reaction down, 20 mL of iced-water was added and the mixture was extracted with AcOEt (3×50 mL). The organic layers were dried over $Na_2SO_4$, filtered and evaporated to give the desired product. $^1H$ NMR (300 MHz, $CDCl_3$) δ 8.85 (s, 1H), 7.58 (d, 1H, J=1.5 Hz), 7.58-7.54 (m, 1H), 2.60 (q, 2H, J=7.5 Hz), 1.29 (t, 3H, J=7.5 Hz).

2-amino-5-bromo-3-ethylbenzoic acid, 9

To a suspension of 8 (1.38 mmol) in 10 mL of NaOH 10% a solution of $H_2O_2$ (0.5 mL) in 4.5 mL of $H_2O$ was added dropwise. The reaction mixture was stirred overnight at room temperature. The reaction mixture was filtered and the filtrate was acidified by adding HCl conc., the resulting precipitate (9) was filtered and dried. $^1H$ NMR (300 MHz, $CDCl_3$) δ 7.95 (d, 1H, J=2.1 Hz), 7.32 (d, 1H, J=2.4 Hz), 2.49 (q, 2H, J=7.2 Hz), 1.28 (t, 3H J=7.2 Hz).

2-amino-5-cyano-3-ethylbenzoic acid, 10

A mixture of 9 (3.3 mmol) and CuCN (3.9 mmol) was reflux in 3 mL of NMP for 4 h. The reaction mixture was poured into a warm solution of NaCN (33% w/v) and vigorously shaken. After cooling down, the reaction was extracted with AcOEt (50 mL) and the organic phase was discarded. The aqueous layer was acidified by adding HCl conc. and the resulting precipitate 10 was collected by filtration. 1H NMR (300 MHz, $CDCl_3$) δ 8.18 (d, 1H, J=1.8 Hz), 7.26 (s, 1H), 6.49 (br s, 1H), 2.51 (q, 2H, J=7.2 Hz), 1.30 (t, 3H, J=7.2 Hz).

10-chloro-6-ethyl-2-methyl-1,2,3,4-tetrahydrobenzo[b][1,6]naphthyridine-8-carbonitrile, 11

A mixture of 10 (0.64 mmol) and 1-methylpiperidin-4-one (0.64 mmol) in $POCl_3$ (2 mL) was heated at 60° C. for 6 h. The excess $POCl_3$ was evaporated off; the residue was treated with iced $H_2O$ and $NaHCO_3$ and extracted with $CH_2Cl_2$ (3×10 mL). The organic layer was dried over $Na_2SO_4$, filtered and evaporated under reduced pressure. The desired compound was purified by triturating with $Et_2O$. $^1H$ NMR (300 MHz, $CDCl_3$) δ 8.42 (d, 1H, J=1.8 Hz), 7.65 (m, 1H), 3.82 (s, 2H), 3.31-3.23 (m, 4H), 2.87 (t, 2H J=5.7 Hz), 2.58 (s, 3H), 1.34 (t, 3H J=7.2 Hz).

10-[(3-chloro-4-methoxybenzyl)amino]-6-ethyl-2-methyl-1,2,3,4-tetrahydrobenzo[b][1,6]naphthyridine-8-carbonitrile A mixture of 11 (0.18 mmol), 3-chloro-4-methoxybenzylamine hydrochloride (0.18 mmol), NaI (0.009 mmol), and phenol (0.18 mmol) was heated at 130° C. for 4 h. The reaction mixture was diluted with $Et_2O$ (30 mL) and washed with 1N NaOH (3×10 mL). The organic layer was dried over $Na_2SO_4$, filtered and evaporated under reduced pressure. The final product D was obtained by Flash Chromatography (AcOEt: MeOH 9:1). MS ESI (m/z) 421 (M+H)$^+$, $^1H$ NMR (300 MHz, $CDCl_3$) δ 8.16 (d, 1H, J=1.5 Hz), 7.56 (s, 1H), 7.36 (d, 1H, J=2.1 Hz), 7.18-7.16 (m, 1H), 6.93 (d, 1H, J=8.4 Hz), 4.48 (s, 2H), 3.92 (s, 3H), 3.54 (s, 2H), 3.25-3.21 (m, 4H), 2.89 (t, 2H, J=6.0 Hz), 2.51 (s, 3H), 1.35 (t, 3H, J=7.5 Hz).

Example 5

6-[(3-chloro-4-methoxybenzyl)amino]-5-oxo-2,3,4,5-tetrahydro-1H-[1,4]diazepino[5,6-b]quinoline-8-carbonitrile Scheme 6:

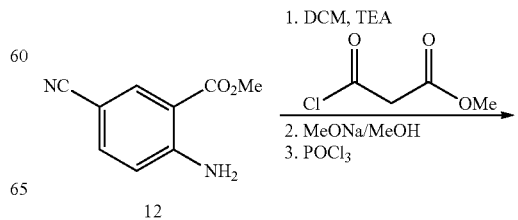

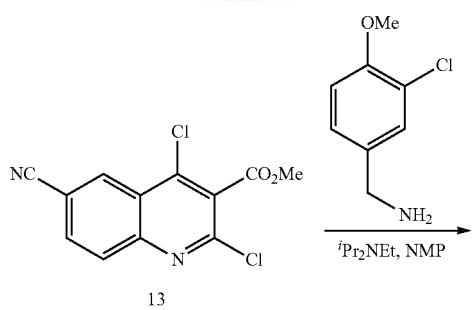

13

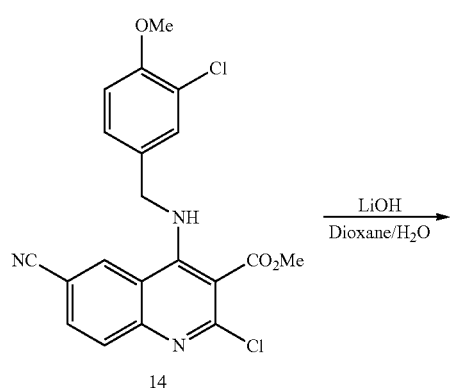

14

15

16

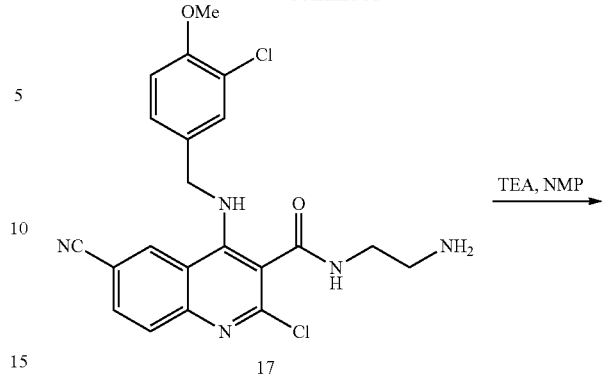

17

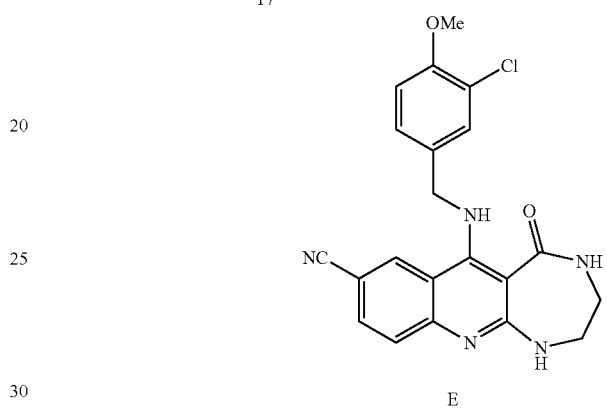

E

Methyl 2,4-dichloro-6-cyanoquinoline-3-carboxylate, 13

To a solution of methyl 2-amino-5-cyanobenzoate (5.68 mmol) in DCM (10 mL) was added triethyamine (8.52 mmol) followed by methyl 3-chloro-3-oxopropionate (7.38 mmol). The resulting reaction mixture was stirred at ambient temperature overnight. The reaction mixture was partitioned between EtOAc and 1M HCl and the layers then separated. The organic layer washed sequentially with saturated aqueous NaHCO$_3$ followed by brine. The organic layer was dried over Na$_2$SO$_4$, filtered, and concentrated in vacuo. The resulting residue was carried on without further purification.

The residue from above was treated with 0.5M NaOMe in MeOH (6.83 mmol). The heterogenous mixture was stirred at ambient temperature for 30 min. Diethyl ether was then added to the reaction mixture and the solid was collected via vacuum filtration, washing with ether. The obtained solid was carried on without further purification.

To a flask containing the solid from above cooled to 0° C. was added POCl$_3$ (15 mL). The mixture became warm and bubbled. The resulting reaction mixture was heated to 90° C. for 3 h. Cooled the dark reaction mixture to ambient temperature and poured it very slowly into stirring saturated aqueous NaHCO$_3$ cooled to 0° C. Solid NaHCO$_3$ was then added until the solution was basic. The aqueous solution was extracted with EtOAc (3x). The combined organic layers were dried over Na$_2$SO$_4$, filtered, and concentrated in vacuo. The obtained residue was purified via flash column chromatography, eluting with 9:1/hexanes:EtOAc, to yield the intermediate 13 (29% over 3 steps). MS ESI (nm/z) 281 (M+H)$^+$; $^1$H NMR (300 MHz, CDCl$_3$) δ 8.63 (d, 1H, J=1.8 Hz), 8.16 (d, 1H, J=8.4 Hz), 8.00 (dd, 1H, J$_1$=1.8, J$_2$=8.4 Hz)

4.08 (s, 3H); $^{13}$C NMR (CDCl$_3$, 75 MHz) (163.4, 148.9, 148.1, 141.8, 133.3, 130.8, 130.6, 128.8, 124.3, 117.7, 112.8, 54.1.

Methyl 2-chloro-4-[(3-chloro-4-methoxybenzyl) amino]-6-cyanoquinoline-3-carboxylate, 14

To a heterogenous mixture of quinoline 13 (3.56 mmol) and 3-chloro-4-methoxy benzylamine.HCl (3.92 mmol) in NMP (15 mL) was added $^i$Pr$_2$NEt (8.90 mmol). The reaction mixture was heated to 80° C. for 3 h. Subsequently, cooled the reaction mixture to ambient temperature and added 1M aqueous HCl and EtOAc. The resulting layers were separated and the organic layer washed with water (3x) followed by brine (1x). The combined organic layers were dried over Na$_2$SO$_4$, filtered, and concentrated in vacuo. The residue was dissolved in a minimum amount of hot EtOAc and allowed to cool to ambient temperature. Hexanes was then added to the solution and the intermediate 14 (80% yield) precipitated out and was collected by vacuum filtration. $^1$H NMR (300 MHz, CDCl$_3$) δ 8.20 (s, 1H), 7.95 (d, 1H, J=8.4 Hz), 7.82 (d, 1H, J=7.5 Hz), 7.38 (s, 1H), 7.27-7.22 (m, 1H), 6.98 (d, 1H, J=8.4 Hz), 6.26 (s, 1H), 4.54 (d, 2H J=4.8 Hz), 3.95 (s, 3H), 3.93 (s, 3H).

2-chloro-4[(3-chloro-4-ethoxybenzyl)amino]-6-cyanoquinoline-3-carboxylic acid, 15

To a solution of ester 14 (2.20 mmol) in 1,4-dioxane (70 mL) was added LiOH (4.40 mmol) and water (20 mL). The resulting solution was stirred at ambient temperature overnight. The reaction mixture was partitioned between ether and 1M aqueous NaOH, the layers separated and the aqueous layer acidified to a pH=2 using concentrated HCl. The precipitated solid was collected via vacuum filtration to yield acid 15 (79% yield) that was used without further purification. $^1$H NMR (300 MHz, DMSO) δ 9.02 (s, 1H), 8.04-8.01 (m, 2H), 7.86 (d, 1H, J=8.7 Hz), 7.44 (s, 1H), 7.28 (d, 1H, J=8.4 Hz), 7.12 (d, 1H, J=8.4; H), 4.57 (d, 2H, J=5.7 Hz), 3.84 (s, 3H).

Perfluorophenyl 2-chloro-4-[(3-chloro-4-methoxybenzyl)amino]-6-cyanoquinoline-3-carboxylate, 16

To a solution of acid 15 (0.833 mmol) and pentafluorophenol (1.67 mmol) in DMF (5.6 mL) and 1,4-dioxane (2.2 mL), was added DCC (1.25 mmol). The reaction mixture was stirred at ambient temperature overnight. Quenched the reaction mixture by addition of 1M aqueous HCl and extracted the aqueous layer with EtOAc (2x). The combined organic layers were washed with 1M NaOH and brine. The combined organic layers were dried over Na$_2$SO$_4$, filtered, and concentrated in vacuo. The obtained residue was purified via flash chromatography, eluting with 4:1/hexanes:EtOAc, to give the ester 16 (56% yield). $^1$H NMR (300 MHz, CDCl$_3$) δ 8.32 (d, 1H, J=1.2 Hz), 7.99 (d, 1H, J=8.7 Hz), 7.89 (dd, 1H, J$_1$=1.2, J$_2$=8.7 Hz), 7.40 (d, 1H, J=2.4 Hz), 7.30-7.24 (m, 1H), 7.01-6.98 (m, 2H), 4.69 (d, 2H, J=4.8 Hz), 3.94 (s, 3H).

N-(2-aminoethyl)-2-chloro-4-[(3-chloro-4-methoxybenzyl)amino]-6-cyanoquinoline-3-carboxamide, 17

To a solution of ester 16 (77.6 μmol) in THF (1.5 mL) was added triethyamine (0.116 mmol) followed by ethylenediamine (0.10 mmol). The resulting reaction mixture was stirred at ambient temperature overnight. The reaction mixture was partitioned between EtOAc and saturated aqueous NaHCO$_3$, the layers separated, and the organic layer washed with 1M HCl (1x). The acidic aqueous layer was basicified to a pH=10 by addition of solid NaHCO$_3$ and then extracted with EtOAc (2x). The combined organic layers were dried over Na$_2$SO$_4$, filtered, and concentrated in vacuo to yield 0.012 g (35% yield) of amine 17 that was used without further purification. MS ESI (m/z) 444 (M+H)$^+$; $^1$H NMR (300 MHz, DMSO) δ 8.92 (s, 1H), 8.52 (t, 1H, J=5.1 Hz), 7.93 (d, 1H, J=8.7 Hz), 7.81 (s, 1H), 7.76 (d, 1H, J=8.7 Hz), 7.33 (s, 1H), 7.19 (d, 1H, J=8.4 Hz), 7.03 (d, 1H, J=8.4 Hz), 4.52 (s, 2H), 3.75 (s, 3H), 3.10-3.01 (m, 2H), 2.54 (t, 2H, J=6.3 Hz).

6-[(3-chloro-4-methoxybenzyl)amino]-5-oxo-2,3,4,5-tetrahydro 1H-[1,4]diazepino[5,6-b]quinoline-8-carbonitrile, E To a solution of amine 17 (27.0 μmol) in NMP (1.0 mL) was added TEA (40.5 μmol). The reaction mixture was heated to 100° C. overnight. Cooled to ambient temperature and partitioned between EtOAc and 1M HCl. The layers were separated and the aqueous layer was basicified to a pH=10 by addition of solid NaHCO$_3$ and then extracted with EtOAc (2x). The combined organic layers were dried over Na$_2$SO$_4$, filtered, and concentrated in vacuo. The obtained residue was purified via flash chromatography, eluting with 19:1/CH$_2$Cl$_2$:MeOH, to yield the desired product (18% yield). MS ESI (m/z) 408 (M+H)$^+$; $^1$H NMR (300 MHz, DMSO) δ 8.72 (s, 1H), 8.28 (s, 1H), 7.78 (s, 1H), 7.68 (dd, 1H, J$_1$=1.5, J$_2$=8.4 Hz), 7.34 (d, 1H, J=9), 7.31 (d, 1H, J=2.1 Hz), 7.19 (dd, 1H, J$_1$=2.1, J$_2$=8.4 Hz), 7.07 (d, 1H, J=8.4 Hz), 6.55 (s, 1H), 4.32 (d, 2H, J=5.7 Hz), 3.81 (s, 3H), 3.1-3.05 (m, 4H).

Example 6

8-bromo-N-(3-chloro-4-methoxybenzyl)-1,2,3,4-tetrahydrobenzo[b][1,6]naphthyridin-10-amine Scheme 7:

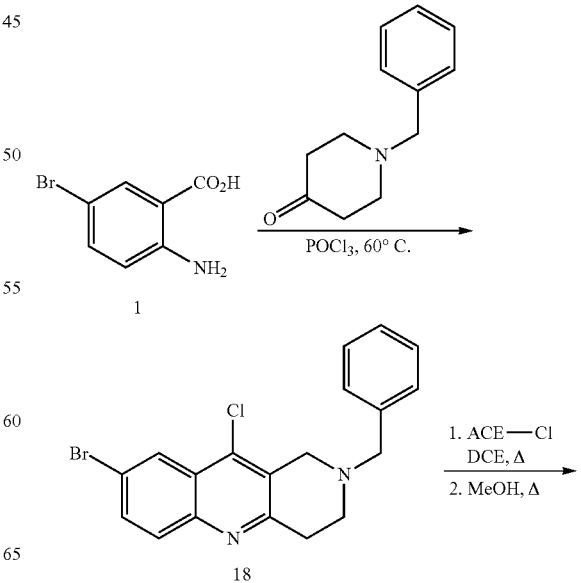

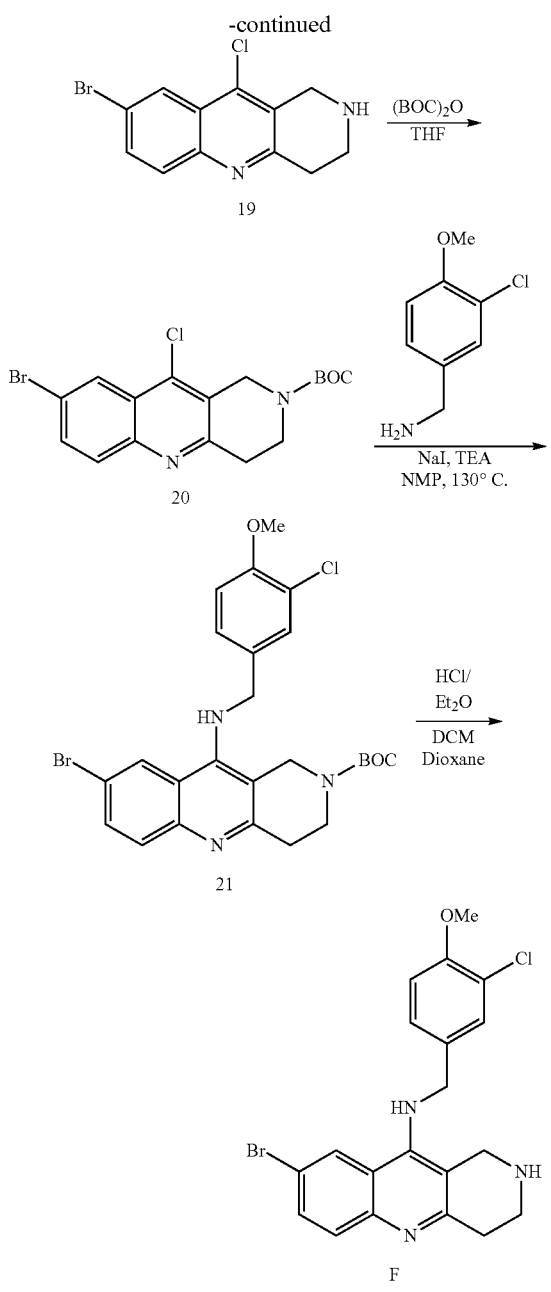

2-benzyl-8-bromo-10-chloro-1,2,3,4-tetrahydrobenzo[b][1,6]naphthyridine, 18

A mixture of 1 (13.9 mmol) and 1-benzylpiperidin-4-one (13.9 mmol) in POCl₃ (50 mL) was heated at 60° C. for 6 h. The excess of POCl₃ was evaporated off; the residue was treated with iced H₂O and NaOH 10% (50 mL) and extracted with CH₂Cl₂ (3×50 mL). The organic layers were dried over Na₂SO₄, filtered and evaporated under reduced pressure. The desired compound (60% yield) was purified by flash chromatography (5% MeOH in DCM). MS ESI (m/z) 387 (M+H)⁺. ¹H NMR (300 MHz, CDCl₃) δ 8.32 (d, 1H, J=1.8 Hz), 7.86 (d, 1H, J=9.0 Hz), 7.75 (dd, 1H, J₁=2.1, J₂=8.7 Hz), 7.43-7.31 (m, 5H), 3.92 (s, 2H), 3.82 (s, 2H), 3.21 (t, 2H, J=6.0 Hz), 2.90 (t, 2H, J=6.0 Hz).

8-bromo-10-chloro-1,2,3,4-tetrahydrobenzo[b][1,6]naphthyridine, 19

1-chloroethyl chloroformate (0.39 mmol) was added dropwise to a solution of 18 (0.26 mmol) in DCE (2 mL) at 0° C. The mixture was heated to reflux for 2 h. DCE was evaporated off; the residue was dissolved in MeOH (15 mL) and reflux for 1 h. The formation of a precipitate was observed. After the reaction mixture was cooled down to r.t., the precipitate was collected by filtration, partitioned between NaOH 1N (10 mL) and AcOEt (10 mL) and the aqueous phase was extracted twice with AcOEt (10 mL). The organic layers were dried over Na₂SO₄, filtered and evaporated under reduced pressure to provide the desired compound 19 (77% yield). ¹H NMR (300 MHz, CD₃OD) δ 8.38 (s, 1H), 7.89 (s, 2H), 4.36 (s, 2H), 3.41 (t, 2H, J=6.0 Hz), 3.21 (t, 2H, J=6.0 Hz).

tert-butyl 8-bromo-10-chloro-3,4-dihydrobenzo[b][1,6]naphthyridine-2(1H)-carboxylate, 20

Di-tert-butyl dicarbonate (0.7 mmol) was added to a solution of 19 (0.84 mmol) in THF (5 mL) at 0° C. The reaction was stirred at r.t. for 1 h. THF was evaporated off, the residue was partitioned between DCM (25 mL) and NaHCO₃ saturated sol. (25 mL). The aqueous portion was extracted with DCM (2×25 mL) and the organic layers were dried over Na₂SO₄, filtered and evaporated under reduced pressure to obtain the intermediate 20 (80% yield). MS ESI (m/z) 397 (M+H)⁺. ¹H NMR (300 MHz, CDCl₃) δ 8.34 (d, 1H, J=2.1 Hz), 7.86 (d, 1H, J=9.0 Hz), 7.77 (dd, 1H, J₁=2.1, J₂=8.7 Hz), 4.82 (s, 2H), 3.83 (t, 2H, J=6.0 Hz), 3.16 (t, 2H, J=6.0 Hz), 1.52 (s, 9H).

tert-butyl 8-bromo-10-((3-chloro-4-methoxybenzyl)amino)-3,4-dihydrobenzo[b][1,6]naphthyridine-2(1H)-carboxylate, 21

A mixture of 20 (0.075 mmol), 3-chloro-4-methoxybenzyl amine hydrochloride (0.38 mmol), TEA (0.38 mmol) and NaI (0.0037 mmol) in NMP (1 mL) was heated to 130° C. and stirred overnight. The reaction was diluted with Et₂O (10 mL) and washed with H₂O (2×20 mL) and brine (20 mL). The organic layers were dried over Na₂SO₄, filtered and evaporated under reduced pressure to give the desired intermediate 21 (40% yield). ¹H NMR (300 MHz, CDCl₃) δ 8.08 (s, 1H), 7.84 (s, 1H), 7.68 (d, 1H, J=9.0 Hz), 7.35 (s, 1H), 7.19 (d, 1H, J=8.1 Hz), 6.93 (d, 1H, J=8.1 Hz), 4.57 (s, 4H), 3.91 (s, 3H), 3.76 (t, 2H, J=6.0 Hz), 3.19 (t, 2H, J=5.7 Hz), 1.49 (s, 9H).

8-bromo-N-(3-chloro-4-methoxybenzyl)-1,2,3,4-tetrahydrobenzo[b][1,6]naphthyridin-10-amine, F A solution of Et₂O/HCl 2M was added dropwise to a solution of 21 in DCM:Dioxane (1:2) (1.5 mL). The mixture was stirred at r.t. overnight. The reaction mixture was diluted with HCl 1N and the organic layer was discarded. The aqueous layer was then basified by using NaHCO₃ and extracted with DCM (3×10 mL). The organic layers were dried over Na₂SO₄, filtered and evaporated under reduced pressure. Flash chromatography (DCM:MeOH 1:1) gave the desired product (15% yield). MS ESI (m/z) 432 (M+H)⁺. ¹H NMR (300 MHz, CDCl₃) δ 8.04 (s, 1H), 7.84-7.73 (m, 2H), 7.65-7.62 (m, 2H), 7.33 (s, 1H), 7.14 (d, 1H, J=8.4 Hz), 6.89

(d, 1H, J=8.4 Hz), 4.45 (d, 2H, J=4.5 Hz), 3.96 (s, 2H), 3.90 (s, 3H), 3.22 (t, 2H, J=6.0 Hz), 3.04 (t, 2H, J=6.0 Hz).

Example 7

10-((3-chloro-4-methoxybenzyl)amino)-1,2,3,4-tetrahydrobenzo[b][1,6]naphthyridine-8-carbonitrile Scheme 8:

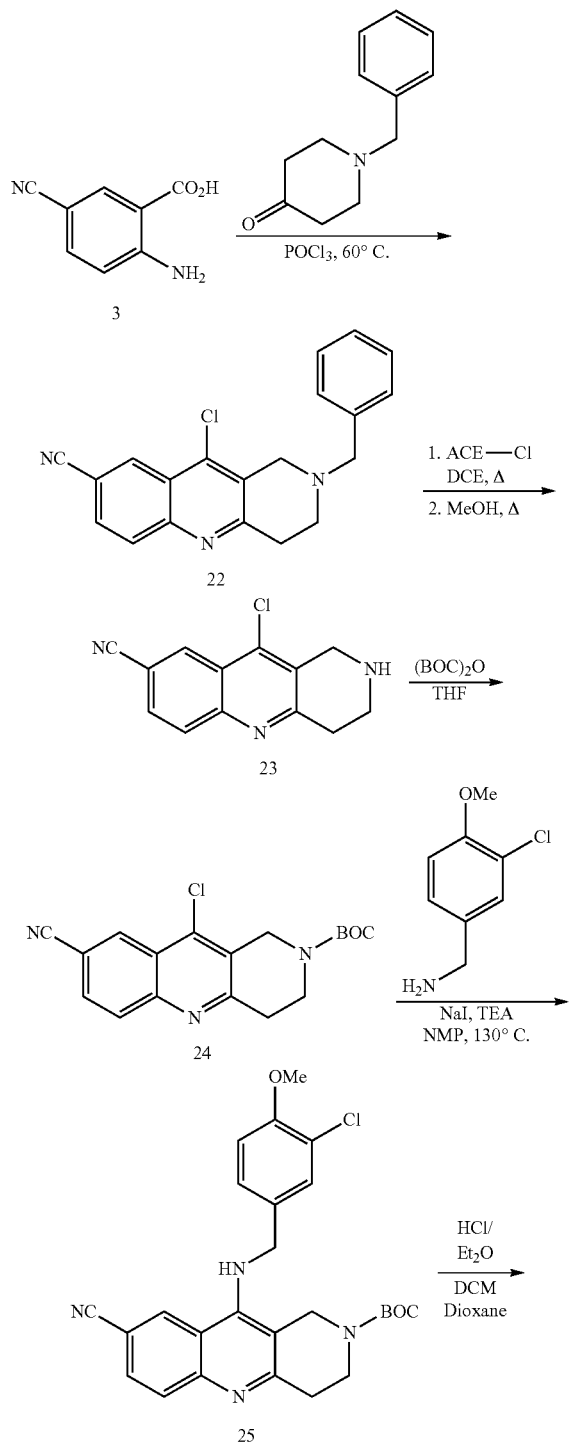

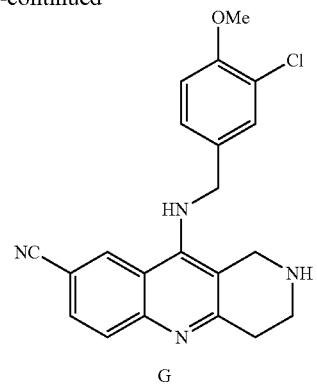

2-benzyl-10-chloro-1,2,3,4-tetrahydrobenzo[b][1,6]naphthyridine-8-carbonitrile, 22

A mixture of 3 (12.3 mmol) and 1-benzylpiperidin-4-one (12.3 mmol) in POCl$_3$ (50 mL) was heated at 60° C. for 6 h. The excess of POCl$_3$ was evaporated off; the residue was treated with iced H$_2$O and NaOH 10% (50 mL) and extracted with CH$_2$Cl$_2$ (3×50 mL). The organic layers were dried over Na$_2$SO$_4$, filtered and evaporated under reduced pressure. The residue was purified by flash chromatography (Hex: AcOEt, 1:2) to give the desired product (54% yield). MS ESI (m/z) 334 (M+H)$^+$; $^1$H NMR (300 MHz, CDCl$_3$) δ 8.56 (d, 1H, J=1.8 Hz), 8.04 (d, 1H, J=8.7 Hz), 7.82 (dd, 1H, J$_1$=1.8, J$_2$=8.7 Hz), 7.43-7.31 (m, 5H), 3.93 (s, 2H), 3.83 (s, 2H), 3.26 (t, 2H, J=6.0 Hz), 2.92 (t, 2H, J=6.0 Hz).

10-chloro-1,2,3,4-tetrahydrobenzo[b][1,6]naphthyridine-8-carbonitrile, 23

1-chloroethyl chloroformate (9.0 mmol) was added dropwise to a solution of 22 (6.0 mmol) in DCE (15 mL) at 0° C. The mixture was heated to reflux for 2 h. DCE was evaporated off and the residue was dissolved in MeOH (15 mL) and reflux for 1 h. The formation of a precipitate was observed. After the reaction mixture was cooled down to r.t., the precipitate was collected by filtration and partitioned between NaOH 1N (50 mL) and AcOEt (50 mL) and the aqueous layer was extracted twice with AcOEt (50 mL). The organic layers were dried over Na$_2$SO$_4$, filtered and evaporated under reduced pressure to yield the intermediate 23 (62% yield). MS ESI (m/z) 244 (M+H)$^+$; $^1$H NMR (300 MHz, CDCl$_3$) δ 8.57 (d, 1H, J=1.2 Hz), 8.04 (d, 1H, J=8.7 Hz), 7.82 (dd, 1H, J$_1$=1.8, J$_2$=8.4 Hz), 4.28 (s, 2H), 3.30 (t, 2H, J=6.0 Hz), 3.17 (t, 2H, J=6.0 Hz), 1.73 (s, 1H).

tert-butyl 10-chloro-8-cyano-3,4-dihydrobenzo[b][1,6]naphthyridine-2(1H)-carboxylate, 24

Di-tert-butyl dicarbonate (3.5 mmol) was added to a solution of 23 (3.5 mmol) in DCM (10 mL) at 0° C. The reaction was stirred at r.t. for 1 h. The reaction was washed with NaHCO$_3$ saturated solution (2×30 mL) and the organic layer was dried over Na$_2$SO$_4$, filtered and evaporated under reduced pressure to obtain the intermediate 24 (94% yield). MS ESI (m/z) 344 (M+H)$^+$.

tert-butyl 10-((3-chloro-4-methoxybenzyl)amino)-8-cyano-3,4-dihydrobenzo[b][1,6]naphthyridine-2(1H)-carboxylate, 25

A mixture of 24 (0.58 mmol), 3-chloro-4-methoxybenzyl amine hydrochloride (2.90 mmol), TEA (2.90 mmol) and NaI (0.03 mmol) in NMP (3 mL) was heated to 130° C. and stirred overnight. The reaction was diluted with Et$_2$O (20 mL) and washed with H$_2$O (2×20 mL) and brine (20 mL). The organic layers were dried over Na$_2$SO$_4$, filtered and evaporated under reduced pressure. Flash chromatography (Hex:AcOEt 1:2) gave the desired intermediate 25 (49% yield). MS ESI (m/z) 479 (M+H); $^1$H NMR (300 MHz, CDCl$_3$) δ 8.33 (d, 1H, J=1.5 Hz), 7.94 (d, 1H, J=8.7 Hz), 7.70 (dd, 1H, J$_1$=1.8, J$_2$=8.7 Hz), 7.31 (s, 1H), 7.17 (dd, 1H, J$_1$=2.1, J$_2$=8.4 Hz), 6.90 (d, 1H, J=8.1 Hz), 4.60-4.55 (m, 4H), 4.36 (s, 1H), 3.89 (2, 3H), 3.75 (t, 2H, J=6.0 Hz), 3.12 (t, 2H, J=6.0 Hz), 1.47 (s, 9H).

10-((3-chloro-4-methoxybenzyl)amino)-1,2,3,4-tetrahydrobenzo[b][1,6]naphthyridine-8-carbonitrile, G A solution of Et$_2$O/HCl 2M was added dropwise to a solution of 25 in DCM:Dioxane (1:2) (1.0 mL). The mixture was stirred at r.t. overnight. The reaction mixture was diluted with HCl 1N and the organic layer was discarded. The aqueous layer was then basified by using NaHCO$_3$ and extracted with DCM (3×10 mL). The organic layers were dried over Na$_2$SO$_4$, filtered and evaporated under reduced pressure. Flash chromatography (DCM:MeOH 1:1) gave the desired product (20% yield). MS ESI (m/z) 379 (M+H)$^+$; $^1$H NMR (300 MHz, CDCl$_3$) δ 8.32 (s, 1H), 7.97 (d, 1H, J=9.7 Hz), 7.71 (d, 1H, J=9.0 Hz), 7.33 (d, 1H, J=1.8 Hz), 7.17 (d, 1H, J=8.4 Hz), 6.93 (d, 1H, J=8.7 Hz), 4.56 (d, 2H, J=5.4 Hz), 4.09 (s, 1H), 3.97 (s, 2H), 3.92 (s, 3H), 3.25 (t, 2H, J=6.0 Hz), 3.11 (t, 2H, J=6.0 Hz).

Example 8

2-acetyl-10-[(3-chloro-4-methoxybenzyl)amino]-1,2,3,4-tetrahydrobenzo[b][1,6]naphthyridine-8-carbonitrile Scheme 9:

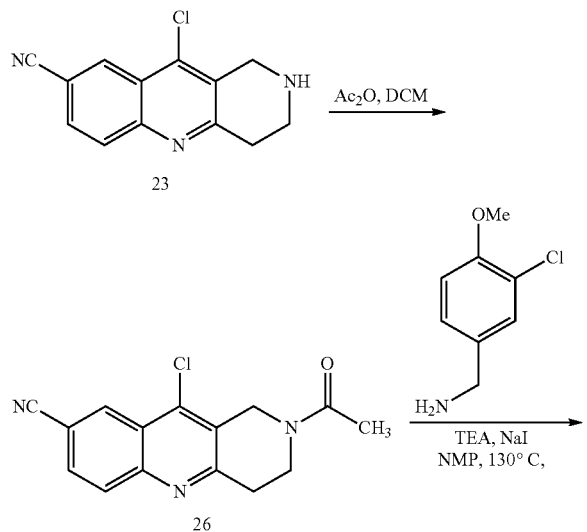

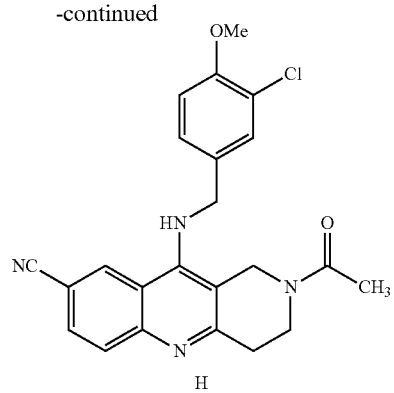

2-acetyl-10-chloro-1,2,3,4-tetrahydrobenzo[b][1,6]naphthyridine-8-carbonitrile, 26

Acetic anhydride (0.41 mmol) was slowly added to a stirring solution of 23 (0.205 mmol; prepared as above) in DCM (1 mL) at 0° C. The reaction was stirred at r.t. for 1 h. Then iced-water was added to the reaction and the organic layer was washed with H$_2$O (2×5 mL) and NaHCO$_3$ (5 mL), dried over Na$_2$SO$_4$, filtered and evaporated under reduced pressure to give the compound 26 (77% yield). MS ESI (m/z) 286 (M+H)$^+$; $^1$H NMR (300 MHz, CDCl$_3$) δ 8.59 (s, 2H), 8.12-8.06 (m, 2H), 7.88-7.84 (m, 2H), 5.01 (s, 2H, 62%), 4.87 (s, 2H, 38%), 4.01 (t, 2H, J=6.0 Hz, 32%), 3.88 (t, 2H, J=6.0 Hz, 68%), 3.30-3.21 (m, 4H), 2.27-2.25 (m, 6H).

2-acetyl-10-[(3-chloro-4-methoxybenzyl)amino]-1,2,3,4-tetrahydrobenzo[b][1,6]naphthyridine-8-carbonitrile, H A mixture of 26 (0.14 mmol), 3-chloro-4-methoxybenzyl amine hydrochloride (0.70 mmol), TEA (0.70 mmol) and NaI (0.007 mmol) in NMP (2 mL) was heated to 130° C. and stirred overnight. The mixture was diluted with CH$_2$Cl$_2$ (10 mL) and washed with H$_2$O (2×10 mL) and brine (10 mL). The organic layers were dried over Na$_2$SO$_4$, filtered and evaporated under reduced pressure. Flash Chromatography (AcOEt: MeOH 9:1) gave the desired product (20% yield). MS ESI (m/z) 421 (M+H)$^+$; $^1$H NMR (300 MHz, CDCl$_3$) δ 8.34 (s, 1H), 7.96 (d, 1H, J=8.7 Hz), 7.73 (dd, 1H, J$_1$=1.5, J$_2$=9.0 Hz), 7.31 (d, 1H, J=2.1 Hz), 7.20 (dd, 1H, J$_1$=2.1, J$_2$=8.4 Hz), 6.93 (d, 1H, J=8.1 Hz), 4.70 (s, 2H), 4.64 (d, 2H, J=6.0 Hz), 4.42 (s, 1H), 3.91 (s, 3H), 3.82 (t, 2H, J=6.0 Hz), 3.20 (t, 2H, J=6.0 Hz), 2.21 (s, 3H).

Example 9

PDE5 Inhibition Assay

Materials and Methods: PDE5 inhibition was assayed at BPS Bioscience (San Diego, Calif.) using BPS PDE assay kits (BPS Catalog number 60300, enzyme lot 090810). Test compounds were supplied as liquid solutions of 10 mM concentration in DMSO. Sildenafil, used as a standard was dissolved in DMSO. Intermediate dilutions were 10% DMSO in PDE assay buffer and tests at ranges from 0.1 to 100 nM. 0.1 ng of enzyme was used per reaction, and the substrate was 100 nM FAM-cGMP.

Assay conditions: A series of dilutions of the test compounds were prepared with 10% DMSO in assay buffer and 5 µl of the dilution was added to a 50 µl reaction so that the final concentration of DMSO is 1% in all of reactions. The enzymatic reactions were conducted at room temperature for 60 minutes in a 50 µl mixture containing PDE assay buffer, 100 nM FAM-cAMP or 100 nM FAM-cGMP, a PDE enzyme, and the test compound. After the enzymatic reaction, 100 µl of a binding solution (1:100 dilution of the binding agent with the binding agent diluent) was added to each reaction and the reaction was performed at room temperature for 60 minutes. Fluorescence intensity was measured at an excitation of 485 nm and an emission of 528 nm using a Tecan Infinite M1000 microplate reader.

Data analysis: PDE activity assays were performed in duplicate at each concentration.

Fluorescence intensity is converted to fluorescence polarization using the Tecan Magellan6 software. The fluorescence polarization data were analyzed using the computer software, Graphpad Prism. The fluorescence polarization ($FP_t$) in absence of the compound in each data set was defined as 100% activity. In the absence of PDE and the compound, the value of fluorescent polarization ($FP_b$) in each data set was defined as 0% activity. The percent activity in the presence of the compound was calculated according to the following equation: % activity=$(FP-FP_b)/(FP_t-FP_b) \times 100\%$, where FP=the fluorescence polarization in the presence of the compound.

The values of % activity versus a series of compound concentrations were then plotted using non-linear regression analysis of Sigmoidal dose-response curve generated with the equation $Y=B+(T-B)/1+10^{(LogEC50-X) \times Hill\ Slope}$, where Y=percent activity, B=minimum percent activity, T=maximum percent activity, X=logarithm of compound and Hill Slope=slope factor or Hill coefficient. The IC50 value was determined by the concentration causing a half-maximal percent activity.

Compounds exhibited PDE5 inhibition in the nanomolar range or below. Exemplary inhibition of representative compounds is shown in Table 1.

TABLE 1

PDE5 and PDE6 Inhibition of Representative Compounds.

| Compound | PDE5 IC$_{50}$ (nM) | PDE6 IC$_{50}$ (nM) |
|---|---|---|
| A | 21.6 | |
| B | 1.0 | |
| C | 0.2 | |
| D | 0.07 | 30.0 |
| E | 43.8 | 6617 |
| F | 5.4 | |
| G | 1.55 | >100 |
| H | 0.056 | 30.1 |

Example 10

Hippocampal cGMP Assay 2-3 month old male and female mice (20-25 g; C57B16 mice) were injected with compound H (3 mg/kg and 10 mg/Kg, 2% DMSO & 2% Tween, i.p.) or Vehicle (2% DMSO & 2% Tween, i.p.). 30 min after administration of vehicle or compound H, mice were subjected to foot shock and sacrificed 10 sec, 1 min and 3 min aftershock by cervical dislocation and decapitation. The hippocampal samples were extracted and snap frozen in liquid nitrogen. Levels of cGMP were quantitated by Enzyme Immunoassay procedure (Cayman Chemical Company, Item no. 581021) following the manufacturer's guidelines in duplicate. cGMP levels were normalized with the protein concentration calculated using BCA Protein Assay Reagent (Thermo Scientific).

cGMP levels in adult mice after treatment with compound H were measured. In a series of preliminary experiments, foot shock induces an immediate increase in cGMP levels in the hippocampus (FIG. 1). Concentration of cGMP was measured by enzyme immunoassay. Basal represents cGMP levels without foot shock. Values are the mean of duplicate determinations. Error bars show S.E.M. (n=3 per group); *p<0.01; ‡p=0.033. Compound H (3 mg/kg and 10 mg/Kg, i.p., 30 minutes prior to electric shock) further enhanced cGMP levels at 10 sec, 60 sec, and 180 sec (0.48±0.014, 0.58±0.033, and 0.58±0.044 pmol/mg, respectively, at the concentration of 3 mg/kg; 0.56±0.033, 0.70±0.028, and 0.63±0.013 pmol/mg, respectively, at the concentration of 10 mg/Kg) as compared to vehicle (0.32±0.015, 0.41±0.028, and 0.46±0.038 pmol/mg after 10 sec, 60 sec and 3 min, respectively).

Example 11

Long-Term Potentiation Electrophysiological Studies

Experimental Section

Transverse hippocampal slices (400 µm) were cut with a tissue chopper (EMS, PA) and maintained in an interface chamber at 29° C. for 90 min prior to recording, as described in Vitolo et al, *Proc. Natl. Acad. Sci. USA* 2002, 13217-13221, herein incorporated by reference in its entirety. The extracellular bath solution consisted of 124.0 mM NaCl, 4.4 mM KCl, 1.0 mM Na$_2$HPO$_4$, 25.0 mM NaHCO$_3$, 2.0 mM CaCl$_2$, 2.0 mM MgSO$_4$, and 10.0 mM glucose, continuously aerated with 95% O$_2$/5% CO$_2$ to a final pH of 7.4. Field extracellular postsynaptic responses (fEPSPs) were recorded by placing the stimulating and recording electrodes in CA1 stratum radiatum. A bipolar tungsten electrode (FHC, Bowdoin, Me.) was used as a stimulating electrode, and a glass pipette filled with bath solution was used as a recording electrode. Basal synaptic transmission was first assessed by plotting the stimulus voltages (V) against slopes of fEPSP to generate input-output relations. A 20-30 min baseline was first recorded every minute at an intensity that evoked a response at approximately 35% of the maximum evoked response. LTP was induced using a theta-burst stimulation (4 pulses at 100 Hz, with the bursts repeated at 5 Hz, and each tetanus consisting of 3 ten-burst trains separated by 15 sec). Responses were measured as fEPSP slopes expressed as percentage of baseline.

Figure 2:
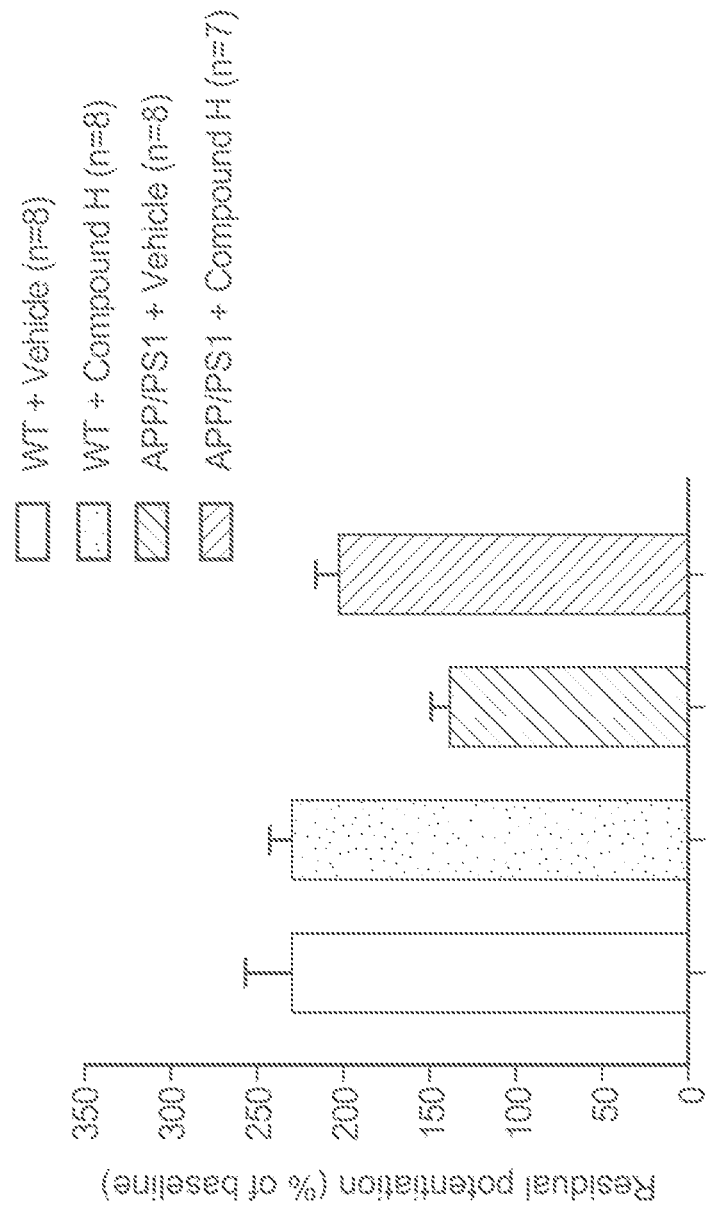
FIG. 2 shows the effects of compound H in wild-type and APP/PS1 mice, a transgenic mouse model of AD, on residual potentiation recorded during the last 5 minutes of a 2 hr recording following tetanic stimulation of the Schaffer collateral fibers at the CA3-CA1 connection.

It was determined whether compound H (50 nM, through the bath perfusion, for 5 min prior to the tetanus) rescues the defect in LTP in 3-4 month old APP/PS1 animals. 201.76%±14.09 potentiation was found in slices from transgenic mice treated with compound compared to 137.30%±10.83 potentiation in slices from APP/PS1 mice treated with vehicle (FIG. 2). Compound H rescues the defect in LTP of APP/PS1 slices. Residual potentiation recorded during the last 5 minutes of a 2 hr recording following tetanic stimulation of the Schaffer collateral fibers at the CA3-CA1 connection. The compound had no effect onto WT slices. P<0.05 comparing compound-treated slices vs vehicle-treated slices in APP/PS1 mice.

Figure 3:
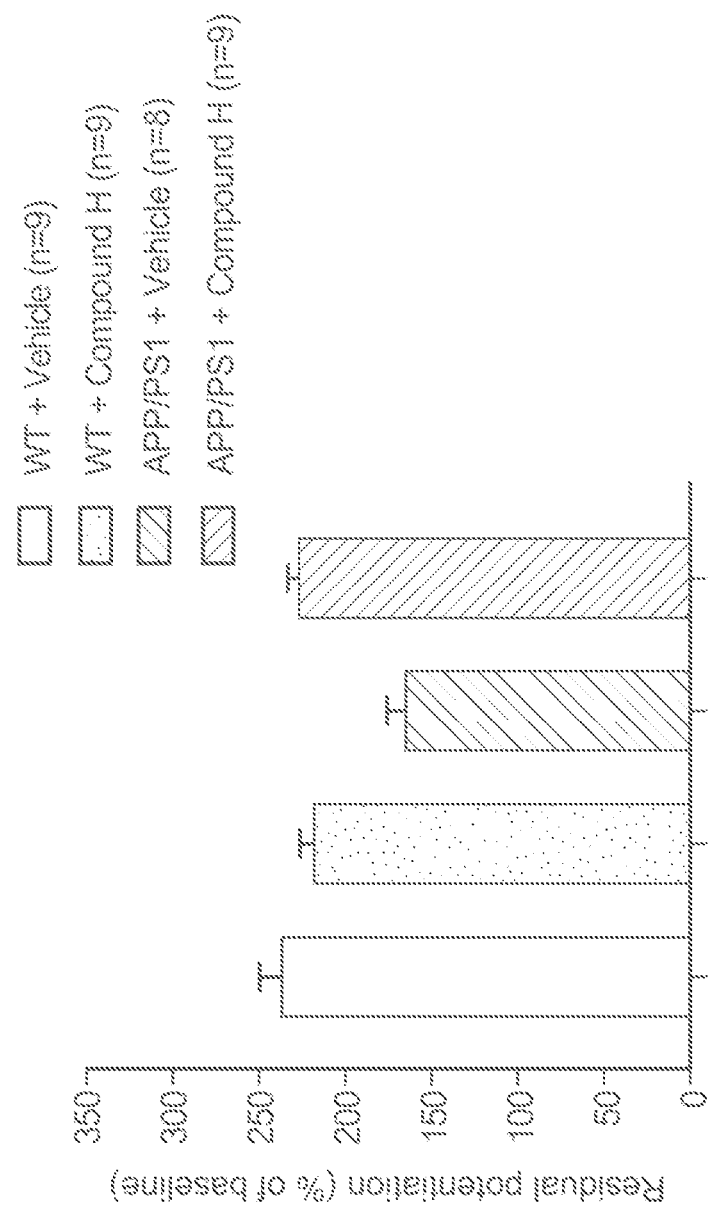
FIG. 3 shows the effects of compound H in wild-type and APP/PS1 mice, a transgenic mouse model of AD, on residual potentiation recorded during the last 5 minutes of a 2 hr recording following tetanic stimulation of the Schaffer collateral fibers at the CA3-CA1 connection. Daily treatment with compound H (3 mg/kg, i.p.) for 3 weeks at the age of 3-4 months re-established normal potentiation when slices were recorded at 6-7 months of age.

Preliminary studies with sildenafil have demonstrated that PDE5 inhibition has prolonged beneficial effects on synaptic and cognitive abnormalities in APP/PS1 mice that persist beyond the administration of the inhibitor. This finding suggests the possibility of using these drugs to interfere with the progression of the memory deficits. It was decided to investigate whether this important therapeutic possibility occurs with compound H. In these experiments, both APP/PS1 and WT mice of 3 months of age were i.p. injected with 3 mg/kg/day with compound H for 3 weeks, then the treatment was stopped for 9-12 weeks prior to testing. Slices from transgenic mice treated with the compound had 226.23%±6.72 potentiation compared to 164.12%±10.37 in slices from vehicle-treated transgenic mice (FIG. 3). Residual potentiation recorded during the last 5 minutes of a 2 hr recording following tetanic stimulation of the Schaffer collateral fibers at the CA3-CA1 connection. Daily treatment with compound H (3 mg/kg, i.p.) for 3 weeks at the age of 3-4 months re-established normal potentiation when slices were recorded at 6-7 months of age.

Example 12

Behavior Studies

Experimental Section

The radial arm water maze task, a hybrid of the classic Morris Water Maze and the radial arm land maze, was performed as described in J. Alamed, D. M. Wilcock, D. M. Diamond, M. N. Gordon, D. Morgan, Two-day radial-arm water maze learning and memory task; robust resolution of amyloid-related memory deficits in transgenic mice, *Nat. Prot.* 1 (2006) 1671-1679, herein incorporated by reference in its entirety. The mouse had to swim in 6 alleys (arms) radiating from a central area until it found a hidden (submerged) platform at the end of one of the arms, based on visual cues placed in the room. The first day of the protocol was a training day on which mice were trained to identify the platform location by alternating between a visible and a hidden platform in a goal arm. The final 3 trials on that day and all 15 trials on day 2 used a hidden escape platform to force mice to use spatial cues to identify the location of the goal arm. To avoid learning limitations imposed by exhausting practice and to avoid fatigue that may result from consecutive trials, spaced practice training was established by running the mice in cohorts of 4 and alternating different cohorts through the 15 training trials over 3-hour testing periods each day. The number of incorrect arm entries (entries to arms with no platform) was counted. If the animal entered the incorrect arm it was gently pulled back to the start arm. Failure to select an arm after 15 sec was counted as an error and the mouse was returned to the start arm. Each trial lasted up to 1 min. After 1 min, if the platform had not been located, the mouse was guided gently through the water by placing a hand behind it to direct it towards the platform. The mouse rested on the platform for 15 sec. The goal platform location was different for each mouse. On day 2, the same procedure was repeated as on day 1 for all 15 trials using only the hidden platform. For data analysis, averages for each mouse were calculated using blocks of 3 trials.

Fear conditioning was assessed as described in B. Gong, O. V. Vitolo, F. Trinchese, S. Liu, M. Shelanski, O. Arancio, Persistent improvement in synaptic and cognitive functions in an Alzheimer mouse model after rolipram treatment, *J. Clin. Invest.* 114 (2004) 1624-1634; F. Trinchese, S. Liu, F. Battaglia, S. Walter, P. M. Mathews, O. Arancio, Progressive age-related development of Alzheimer-like pathology in APP/PS1 mice, *Ann. Neurol.* 55 (2004) 801-814; and B. Gong, Z. Cao, P. Zheng, O. V. Vitolo, S. Liu, A. Staniszewski, D. Moolman, H. Zhang, M. Shelanski, O. Arancio, Ubiquitin hydrolase Uch-L1 rescues beta-amyloid-induced decreases in synaptic function and contextual memory, *Cell* 126 (2006) 775-788; each herein incorporated by reference in its entirety. First, sensory perception of electric foot shock was examined in different groups of mice through the threshold assessment test. Animals were placed in the conditioning chamber and the electric current (0.1 mA for 1 sec) was increased at 30 s intervals from 0.1 mA to 0.7 mA. Threshold to flinching (first visible response to shock), jumping (first extreme motor response), and vocalized response were quantified for each animal by averaging the shock intensity at which each animal showed the behavioral response to that type of shock. Training of fear conditioning was performed by placing the mouse in a conditioning chamber for 2 min before the onset of a tone (Conditioned Stimulus (CS), 30 sec, 85 dB sound at 2800 Hz). In the last 2 sec of the CS, mice were given a 2 sec, 0.7 mA mild foot shock (Unconditioned Stimulus, (US)) through the bars of the floor. After the US, the mice were left in the chamber for another 30 s. Freezing behavior, defined as the absence of movements except for respiratory excursions, was scored using Freezeview software (Med Associates, St. Albans, Vt.). Contextual fear learning was evaluated 24 hrs after training by measuring freezing responses for 5 min in the same chamber where the mice were trained. Cued fear learning was evaluated 24 hrs after contextual testing. The mice were placed in a novel context for 2 min (pre-CS test), after which they were given a CS for 3 min (CS test), and freezing behavior was measured during the first 30 sec that mimic the CS-US conditioning and the remaining 2.5 min.

Figure 4:
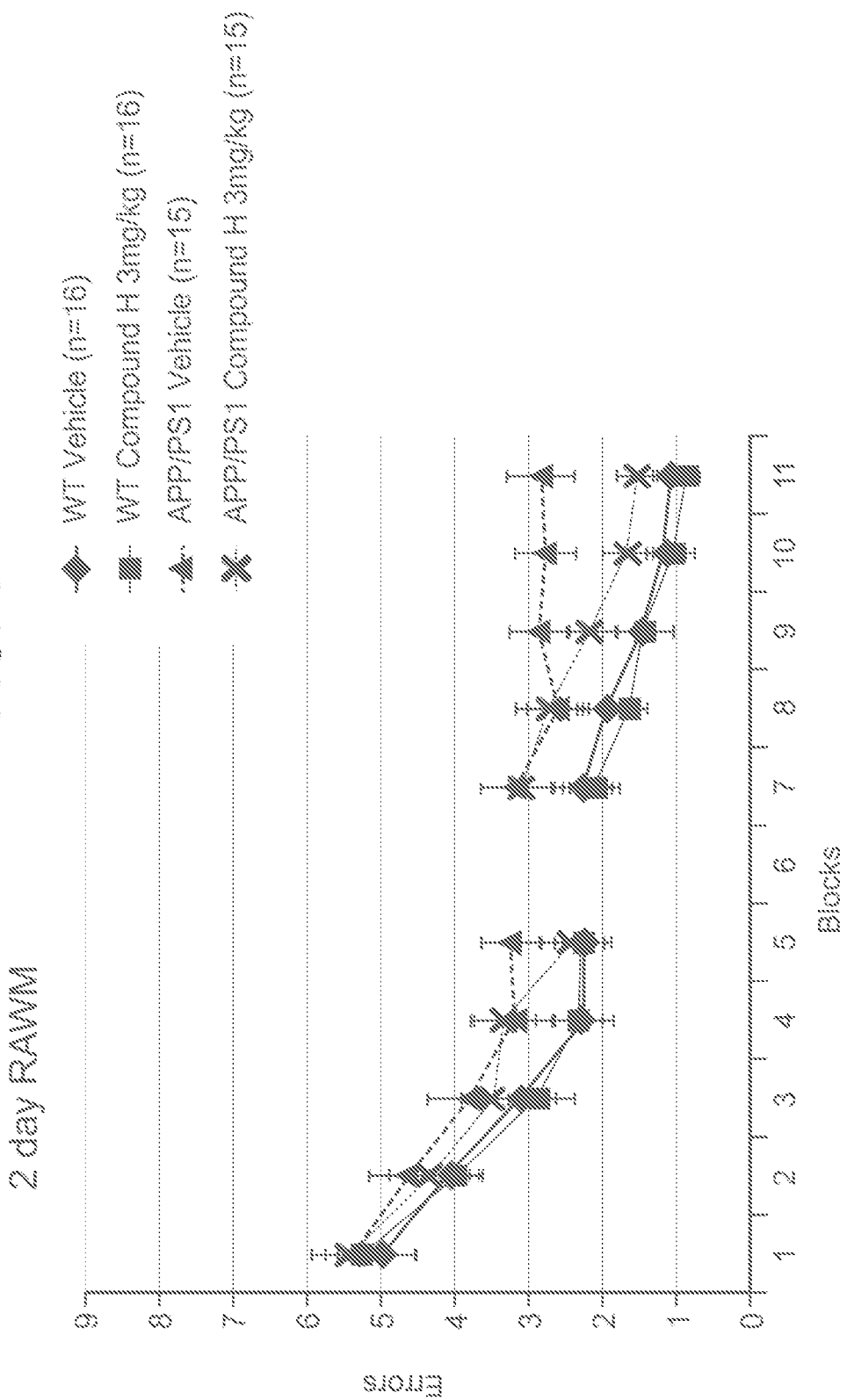
FIG. 4 shows the effects of compound H on defects in reference memory in wild-type and APP/PS1 mice, a transgenic mouse model of AD, in the 2 day radial arm water maze. Daily treatment with the compound for 3 weeks at the age of 3-4 months reduced the number of errors with the 2-day radial arm water maze in APP/PS1 mice.

It was determined whether compound H (3 mg/kg, i.p, for 3 weeks) rescues the defect in reference memory in 3-4 month old APP/PS1 animals. Transgenic mice treated with the compound made between 1 to 2 errors in the last trial of the 2-day RAWM test in contrast to transgenic littermates treated with vehicle that made about 3 errors (FIG. 4). Compound H rescues the defect in reference memory of APP/PS1 mice. Daily treatment with the compound for 3 weeks at the age of 3-4 months reduced the number of errors with the 2-day radial arm water maze in APP/PS1 mice. The compound had no effect on WT mice. p<0.05 comparing compound-treated transgenic mice vs vehicle-treated APP/PS1 mice.

Figure 5:
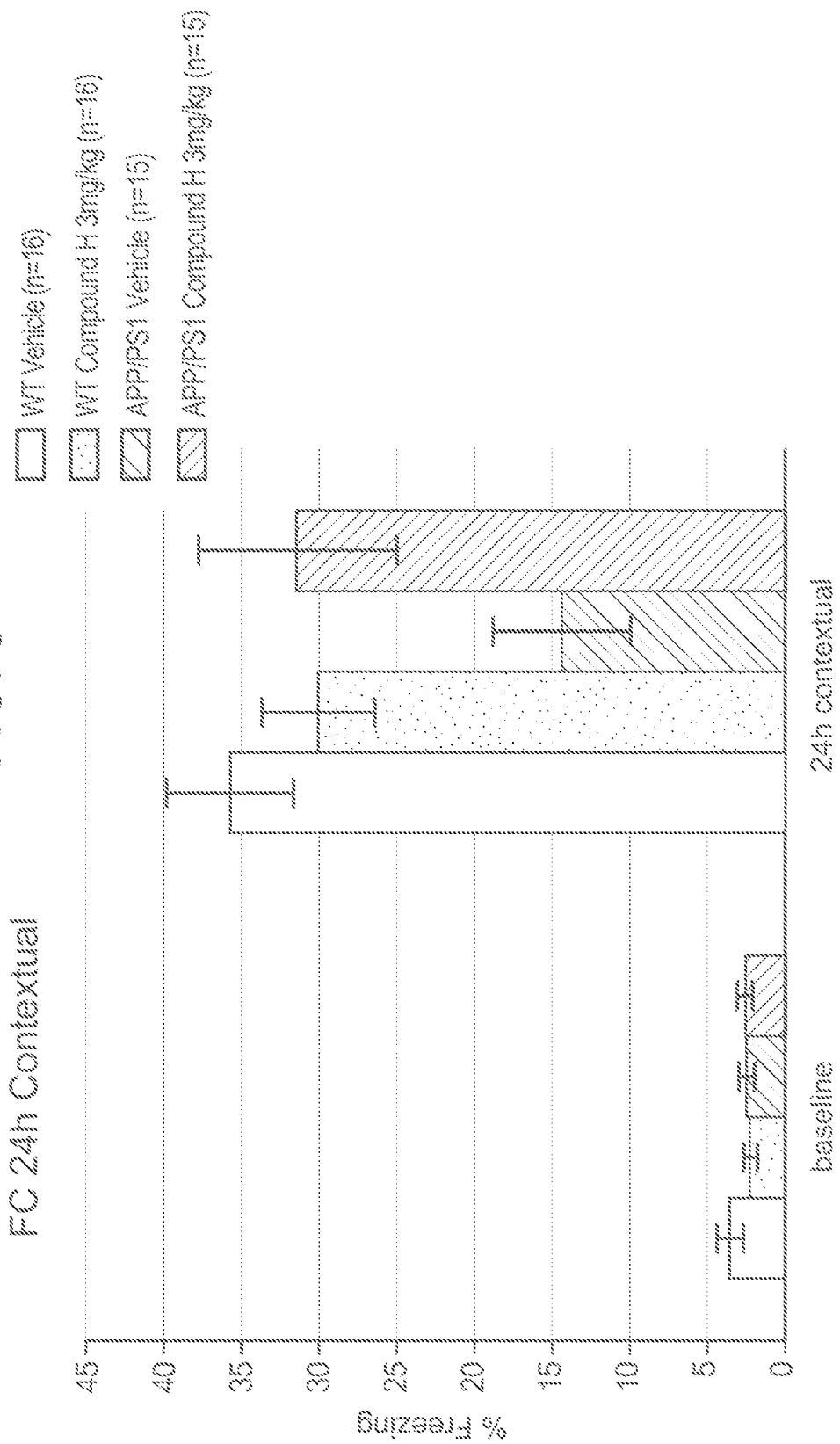
FIG. 5 shows the effects of compound H on defects in fear memory in wild-type and APP/PS1 mice, a transgenic mouse model of AD, on contextual fear memory. Daily treatment with the compound for 3 weeks at the age of 3-4 months re-established normal freezing in a test for contextual fear memory in APP/PS1 mice.

It was also determined if compound H (3 mg/kg, i.p, for 3 weeks) rescues the defect in fear memory in 3-4 month old APP/PS1 animals. Transgenic mice treated with the compound froze ~30% of the time when they were exposed after 24 hrs to the same context in which they had received an electric shock compared to about 15% for vehicle-treated APP/PS1 mice (FIG. 5). Compound H rescues the defect in fear memory of APP/PS1 mice. Daily treatment with the compound for 3 weeks at the age of 3-4 months re-established normal freezing in a test for contextual fear memory in APP/PS1 mice. The compound had no effect on WT mice. p<0.05 comparing compound-treated transgenic mice vs vehicle-treated APP/PS1 mice.

Figure 6:
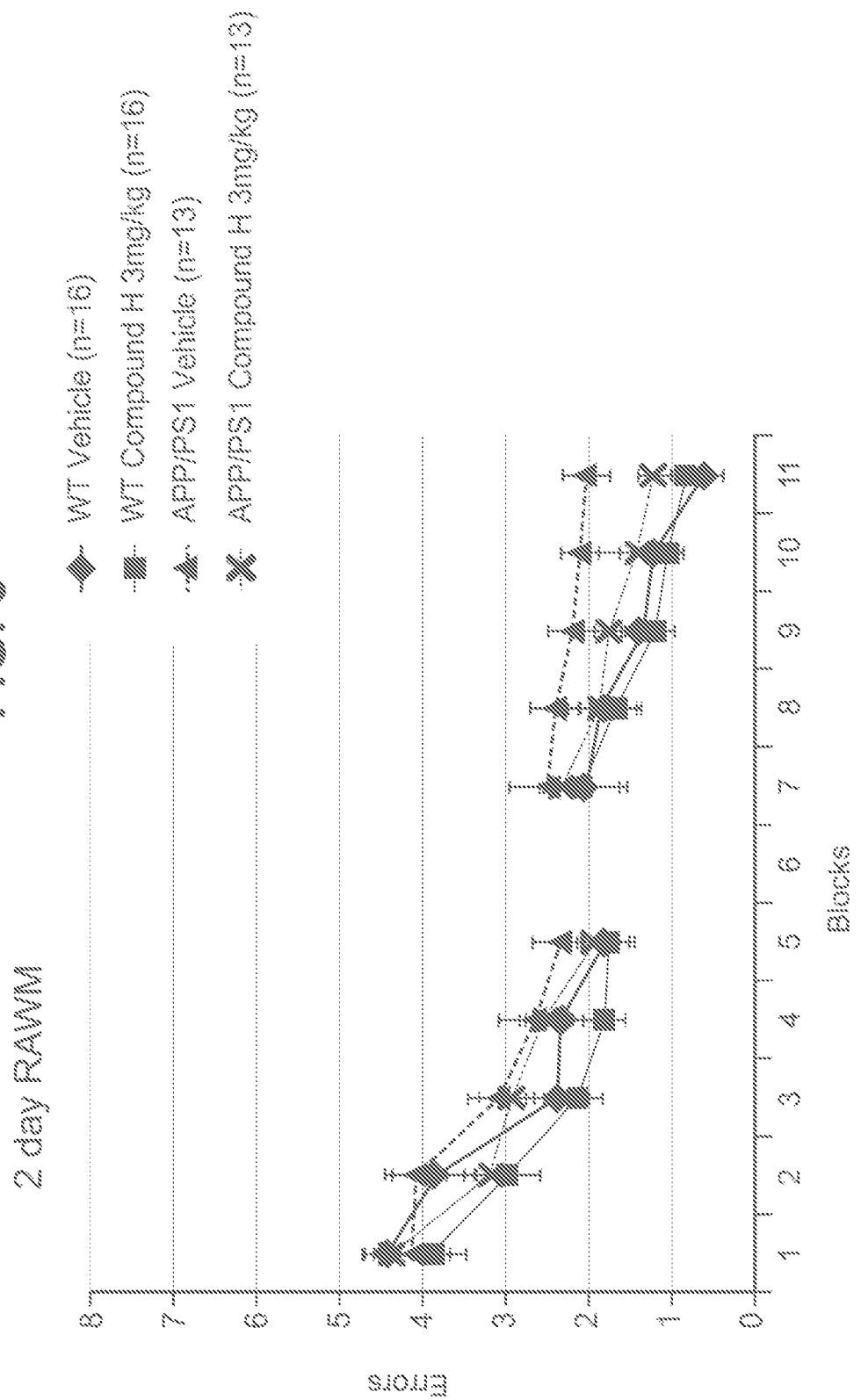
FIG. 6 shows the effects of compound H on defects in reference memory in wild-type and APP/PS1 mice, a transgenic mouse model of AD, in the 2 day radial arm water maze. Daily treatment with compound (3 mg/kg, i.p.) for 3 weeks at the age of 3-4 months reduced the number of errors with the 2-day radial arm water maze when mice were examined at 6-7 months of age.
Figure 7:
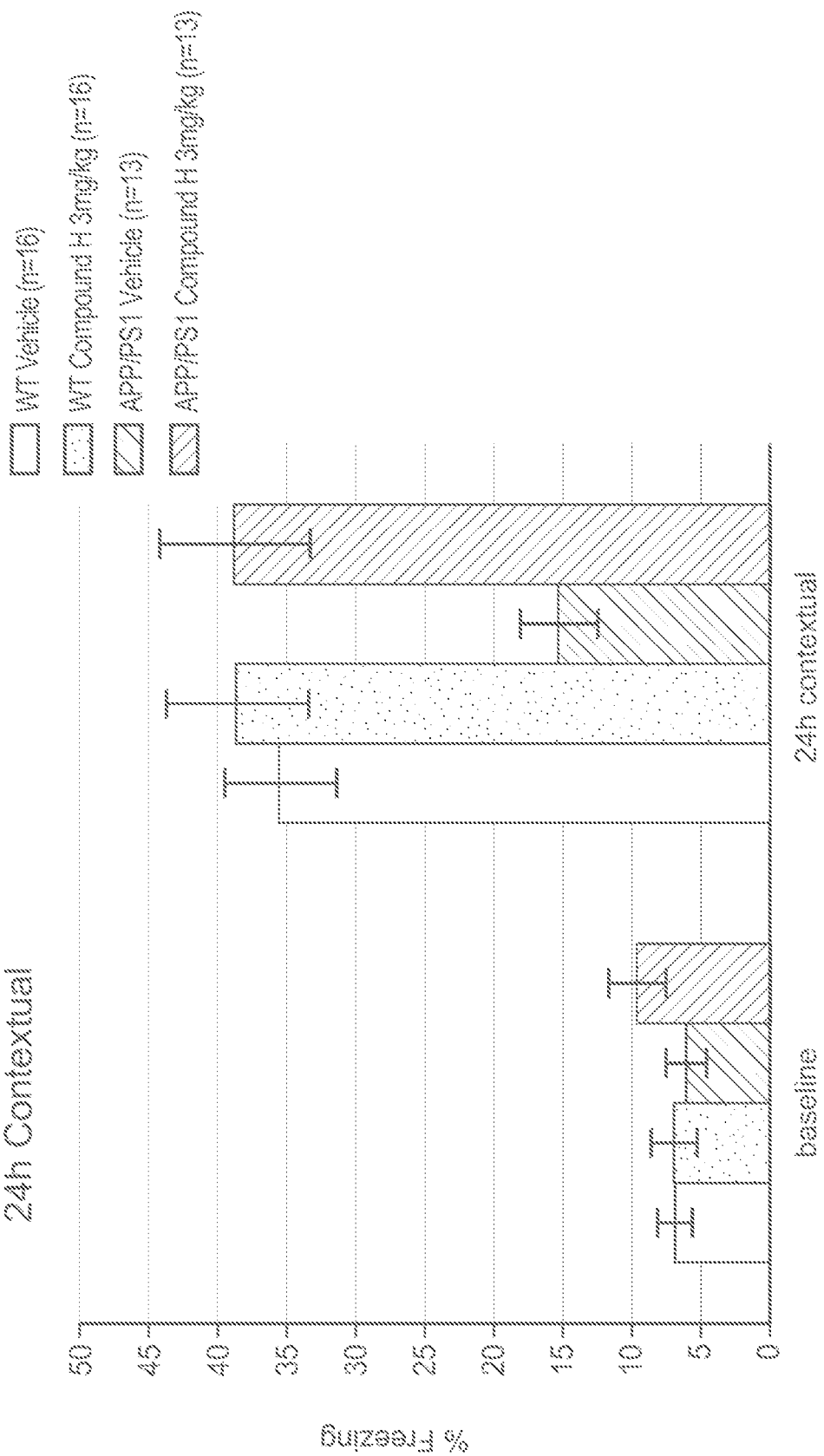
FIG. 7 shows the effects of compound H on defects in fear memory in wild-type and APP/PS1 mice, a transgenic mouse model of AD, on contextual fear memory. Daily treatment with compound (3 mg/kg, i.p.) for 3 weeks at the age of 3-4 months re-established normal freezing in a test for contextual fear memory when mice were examined at 6-7 months of age.

The possibility of compound H to interfere with the progression of memory deficits was investigated. Both APP/PS1 and WT mice of 3-4 months of age were i.p. injected with compound H (3 mg/kg/day) for 3 weeks, then the treatment was stopped for 9-12 weeks prior to testing. Mice were next subjected to 2-day RAWM and fear conditioning. Transgenic mice treated with the compound made ~1 error in the 2-day RAWM test compared to ~2 errors in vehicle-treated transgenic mice (FIG. 6). Daily treatment with compound H (3 mg/kg, i.p.) for 3 weeks at the age of 3-4 months reduced the number of errors with the 2-day radial arm water maze when mice were examined at 6-7 months of age. Contextual memory experiments revealed ~40% freezing in transgenic mice treated with the compound compared to ~15% in vehicle-treated transgenic mice (FIG. 7). Daily treatment with compound H (3 mg/kg, i.p.) for 3 weeks at the age of 3-4 months re-established normal freezing in a test for contextual fear memory when mice were examined at 6-7 months of age. Thus, synaptic and cognitive improvements persist beyond the administration of the inhibitor.

Example 13

Pharmacokinetic Studies

Figure 8:
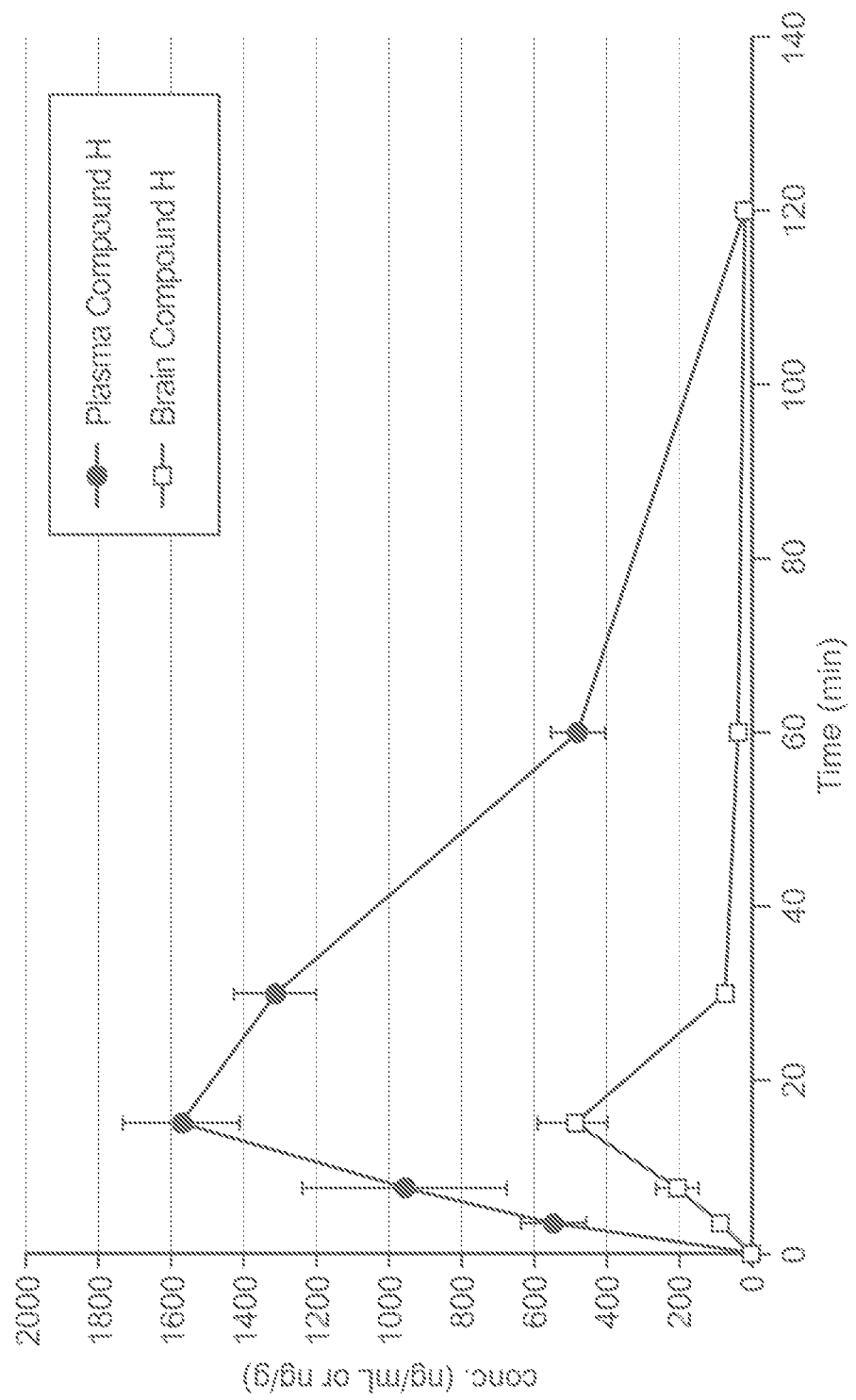
FIG. 8 shows concentrations-time course of compound H in mice brain and plasma following i.p. administration of 25 mg/kg dose.

The PK study of compound H (25 mg/kg, i.p.) was conducted in male C57B16 mice. The plasma and brain concentrations of compound H at different time points are shown in FIG. 8.

Following i.p. administration of 25 mg/kg to C57B16 mice, compound H was rapidly absorbed as indicated by peak plasma concentration occurring at 0.25 h after dosing (Table 2). The distribution of compound H to brain was fast with a similar $T_{max}$ value in the brain. The exposure of compound H in brain was lower than in plasma with a $C_{max}$ ratio of 0.31. The elimination half-lives of compound H in brain and plasma were 0.65 and 1.07 h, respectively.

TABLE 2

Pharmacokinetic parameters for Compound H in mice.

| Parameters | | Brain | Plasma | Ratio (brain/plasma) |
|---|---|---|---|---|
| Tmax | (h) | 0.25 | 0.25 | — |
| Cmax | (ng/mL or ng/g) | 492.25 | 1571.44 | 0.313 |
| t½ | (h) | 0.65 | 1.07 | — |
| MRT | (h) | 0.95 | 1.56 | — |

$C_{max}$: the maximum observed concentration; $T_{max}$: time corresponding to $C_{max}$; MRT: Mean Residence Time; $t_{1/2}$: the elimination half-life.

Example 14

Acute Toxicity Studies

Figure 9:
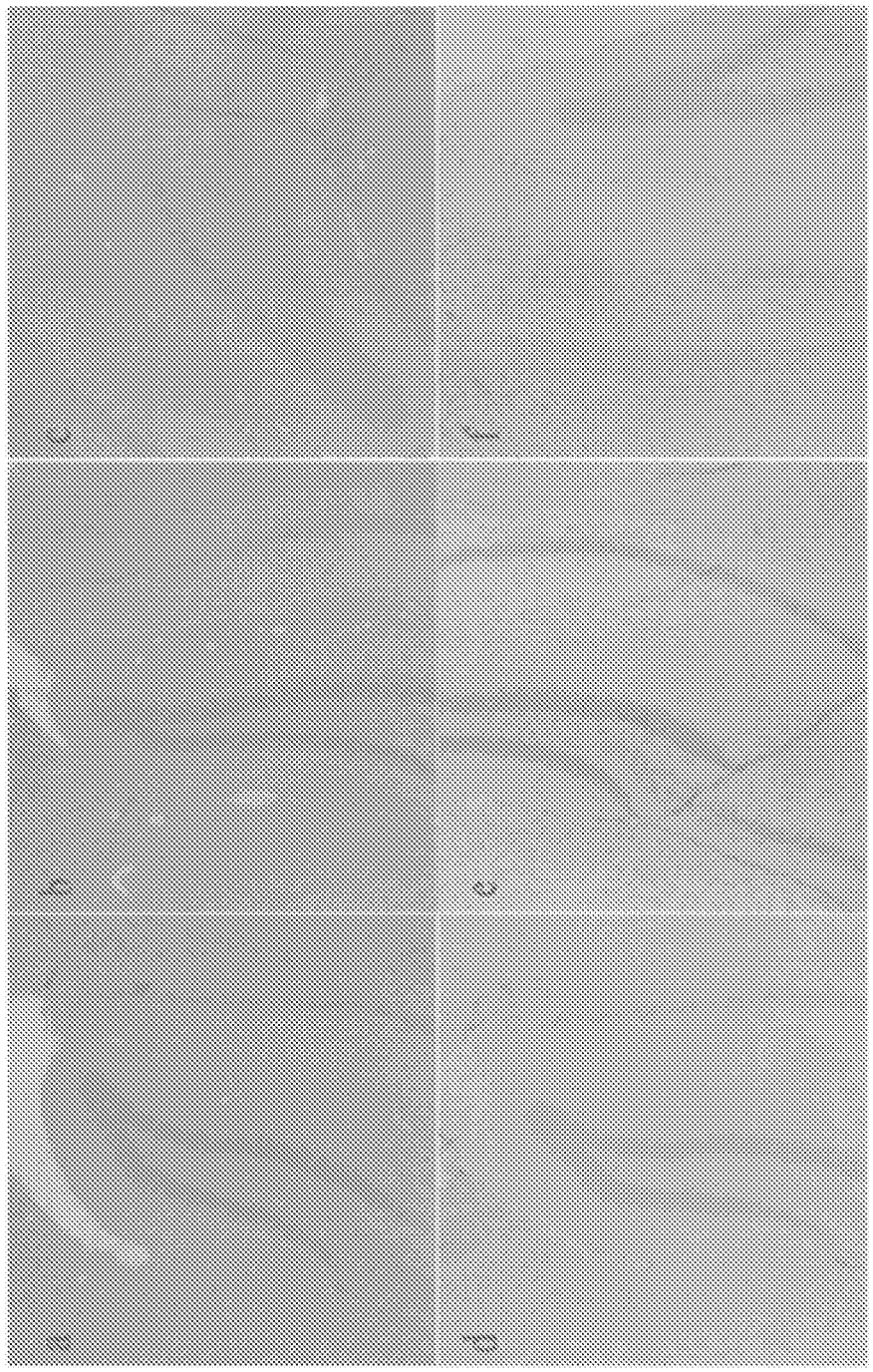
FIG. 9 shows H&E staining for three groups (A: vehicle; B: 120 mg/kg compound H; C: 240 mg/kg compound H); and a GFAP immunostain for three groups (D: vehicle; E: 120 mg/kg compound H, F: 240 mg/kg compound H).

Mice were given compound H at two different concentrations (120 or 240 mg/kg, i.p.) or vehicle, and sacrificed afterwards (compound H at a concentration of 480 mg/kg, i.p. was fatal, however the efficacious dose of compound H was 3 mg/kg). Brain, muscle, kidney, and liver were harvested from each mouse, and tissue from each organ was examined histologically by a board-certified pathologist for signs of toxicity. Sections of brain did not show any signs of toxicity by H&E, and a GFAP immunostain showed no signs of gliosis (FIG. 9). Additional stains on sections of brain with LFB-PAS revealed no signs of demyelination, and an immunostain for CD45 showed no signs of inflammation. Sections of muscle showed no signs of toxicity by H&E, and a trichrome stain showed no muscle fibrosis. Sections of kidney showed no toxicity by H&E staining. Additional staining of kidney sections with PAS did not show any abnormalities in the glomerular basement membrane, and trichrome staining showed no fibrosis. Sections of liver did not show any signs of toxicity by H&E staining, and a trichrome stain showed no fibrosis or cirrhotic liver disease. The compound showed no signs of neurotoxicity in the brain. H&E staining shows no difference between the three groups (FIG. 9A: vehicle; FIG. 9B: 120 mg/kg; FIG. 9C: 240 mg/kg). In addition, a GFAP immunostain shows no signs of gliosis in any of the three groups (FIG. 9D: vehicle; FIG. 9E: 120 mg/kg, FIG. 9F: 240 mg/kg).

Example 15

1-(10-((3-chloro-4-methoxybenzyl)amino)-3,4-dihydrobenzo[b][1,6]naphthyridin-2(1H)-yl)ethan-1-one

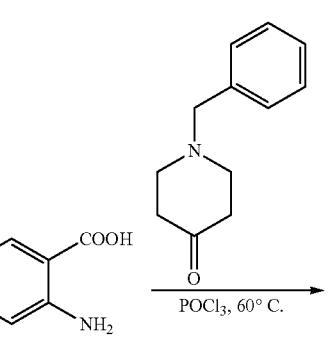

2-benzyl-10-chloro-1,2,3,4-tetrahydrobenzo[b][1,6] naphthyridine 28

A mixture of 2-aminobenzoic acid 27 (7.3 mmol) and 1-methylpiperidin-4-one (7.3 mmol) in POCl3 (5 mL) was heated at 60° C. for 6 h. The excess POCl₃ was evaporated off; the residue was treated with iced H₂O and NaHCO₃ and extracted with CH₂Cl₂ (3×25 mL). The organic layer was dried over Na₂SO₄, filtered and evaporated under reduced pressure. Purification by Flash Chromatography (5% MeOH in AcOEt) gave the desired compound 28. MS ESI (m/z) 309 (M+H)⁺; ¹H NMR (400 MHz, CDCl₃) δ 8.16 (dd, 1H, $J_1$=1.2, $J_2$=8.4 Hz), 8.0 (d, 1H, J=8.4 Hz), 7.71-7.67 (m, 1H), 7.58-7.54 (m, 1H), 7.44-7.42 (m, 2H), 7.39-7.35 (m, 2H), 7.33-7.30 (m, 1H), 3.95 (s, 2H), 3.84 (s, 2H), 3.25 (t, 2H, J=5.6 Hz), 2.93 (t, 2H, J=5.6 Hz).

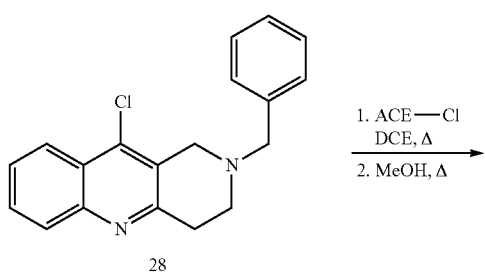

28

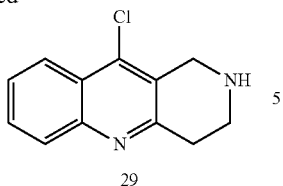

10-chloro-1,2,3,4-tetrahydrobenzo[b][1,6]naphthyridine 29

1-chloroethyl chloroformate (6.3 mmol) was added dropwise to a solution of 28 (4.2 mmol) in DCE (5 mL) at 0° C. The mixture was heated to reflux for 2 h. DCE was evaporated off and the residue was dissolved in MeOH (5 mL) and reflux for 1 h. The formation of a precipitate was observed. After the reaction mixture was cooled down to r.t., the precipitate was collected by filtration and partitioned between NaOH 1N (50 mL) and AcOEt (50 mL) and the aqueous layer was extracted twice with AcOEt (50 mL). The organic layers were dried over Na$_2$SO$_4$, filtered and evaporated under reduced pressure to yield 29. MS ESI (m/z) 219 (M+H)$^+$.

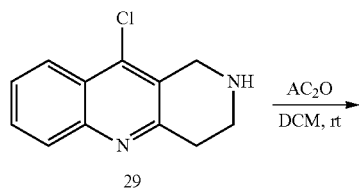

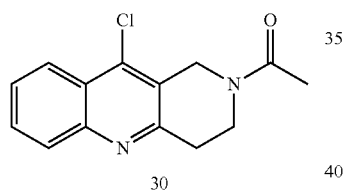

1-(10-chloro-3,4-dihydrobenzo[b][1,6]naphthyridin-2(1H)-yl)ethan-1-one 30

Acetic anhydride (3.65 mmol) was slowly added to a stirring solution of 29 (1.83 mmol) in DCM (4 mL) at 0° C. The reaction was stirred at r.t. for 1 h. Then iced-water was added to the reaction and the organic layer was washed with H$_2$O (2×10 mL) and NaHCO$_3$ (10 mL), dried over Na$_2$SO$_4$, filtered and evaporated under reduced pressure to give compound 30.

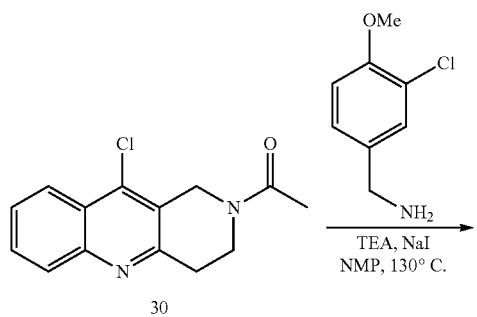

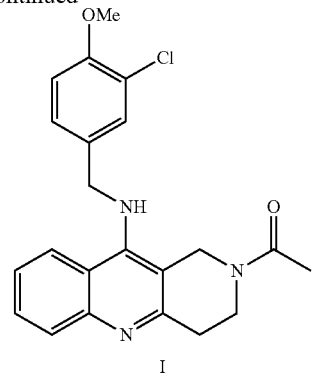

1-(10-((3-chloro-4-methoxybenzyl)amino)-3,4-dihydrobenzo[b][1,6]naphthyridin-2(1H)-yl)ethan-1-one, I A solution of 30 (1.15 mmol), 3-chloro-4-methoxybenzylamine hydrochloride (3.45 mmol), NaI (0.06 mmol), and triethylamine (3.45 mmol) in NMP (5.0 mL) was heated at 130° C. for 6 h. The solvent was evaporated off and the residue was purified by Flash Chromatography (AcOEt:MeOH 8:2) to give I. MS ESI (m/z) 396 (M+H); $^1$H NMR (400 MHz, CDCl$_3$) δ 8.05-8.02 (m, 1H), 7.92 (d, 1H, J=9.2 Hz), 7.67-7.63 (m, 1H), 7.45-7.40 (m, 1H), 7.35 (d, 1H, J=2.4 Hz), 7.22 (dd, 1H, J$_1$=2.0, J$_2$=8.4 Hz), 6.92 (d, 1H, J=8.4 Hz), 4.75 (s, 2H), 4.65 (d, 2H, J=5.2 Hz), 3.90 (s, 4H), 3.81 (t, 2H, J=6.0 Hz), 3.27 (t, 2H, J=6.4 Hz), 2.20 (s, 3H).

Example 16

1-(10-((3-chloro-4-methoxybenzyl)amino)-8-methoxy-3,4-dihydrobenzo[b][1,6]naphthyridin-2(1H)-yl)ethan-1-one

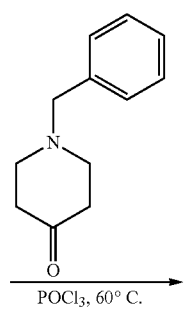

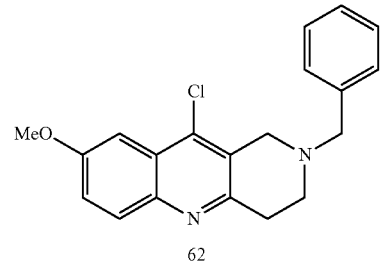

2-benzyl-10-chloro-8-methoxy-1,2,3,4-tetrahydrobenzo[b][1,6]naphthyridine 62

A mixture of 2-amino-5-methoxybenzoic acid 61 (1.2 mmol) and 1-methylpiperidin-4-one (1.2 mmol) in POCl$_3$ (2.0 mL) was heated at 60° C. for 3 h. The excess POCl$_3$ was evaporated off; the residue was treated with iced NH$_3$ aq. and extracted with AcOEt (3×20 mL). The organic layer was dried over Na$_2$SO$_4$, filtered and evaporated under reduced pressure. Purification by Flash Chromatography (AcOEt) gave the desired compound 62. MS ESI (m/z) 339 (M+H)$^+$; $^1$H NMR (400 MHz, CDCl$_3$) δ 7.86 (d, 1H, J=9.2 Hz), 7.41-7.23 (m, 7H), 3.93 (s, 3H), 3.90 (s, 2H), 3.80 (s, 2H), 3.18 (t, 2H, J=6.0 Hz), 2.87 (t, 2H, J=5.6 Hz).

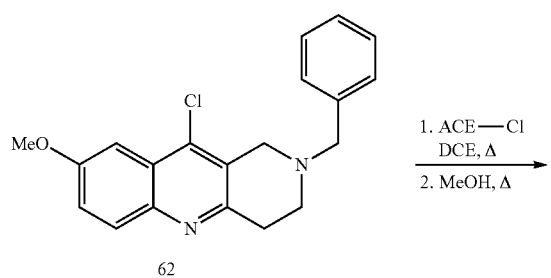

10-chloro-8-methoxy-1,2,3,4-tetrahydrobenzo[b][1,6]naphthyridine 63

1-chloroethyl chloroformate (0.62 mmol) was added dropwise to a solution of 62 (0.41 mmol) in DCE (3.0 mL) at 0° C. The mixture was heated to reflux for 2 h. DCE was evaporated off and the residue was dissolved in MeOH (5.0 mL) and reflux for 1 h. The formation of a precipitate was observed. After the reaction mixture was cooled down to r.t., the precipitate was collected by filtration and partitioned between NaOH 1N (20 mL) and AcOEt (20 mL) and the aqueous layer was extracted twice with AcOEt (20 mL). The organic layers were dried over Na$_2$SO$_4$, filtered and evaporated under reduced pressure to yield 63. MS ESI (m/z) 249 (M+H)$^+$; $^1$H NMR (400 MHz, CDCl$_3$) δ 7.89 (d, 1H, J=8.8 Hz), 7.39 (d, 1H, J=2.8 Hz), 7.34 (dd, 1H, J$_1$=2.4, J$_2$=8.8 Hz), 4.25 (s, 2H), 3.96 (s, 3H), 3.28 (t, 2H, J=6.0 Hz), 3.11 (t, 2H, J=6.4 Hz).

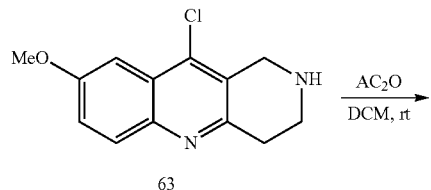

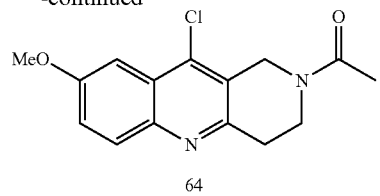

1-(10-chloro-8-methoxy-3,4-dihydrobenzo[b][1,6]naphthyridin-2(1H)-yl)ethan-1-one 64

Acetic anhydride (0.56 mmol) was slowly added to a stirring solution of 63 (0.28 mmol) in DCM (1.0 mL) at 0° C. The reaction was stirred at r.t. for 1 h. Then iced-water was added to the reaction and the organic layer was washed with H$_2$O (2×10 mL) and NaHCO$_3$ (10 mL), dried over Na$_2$SO$_4$, filtered and evaporated under reduced pressure to give compound 64. MS ESI (m/z) 291 (M+H)$^+$; $^1$H NMR (400 MHz, CDCl$_3$) δ 7.91 (d, 1H, J=9.2 Hz), 7.42-7.40 (m, 1H), 7.39-7.36 (m, 1H), 4.98 (s, 2H), 3.97 (s, 3H), 3.86 (t, 2H, J=6.0 Hz), 3.22 (t, 2H, J=6.0 Hz), 2.25 (s, 3H).

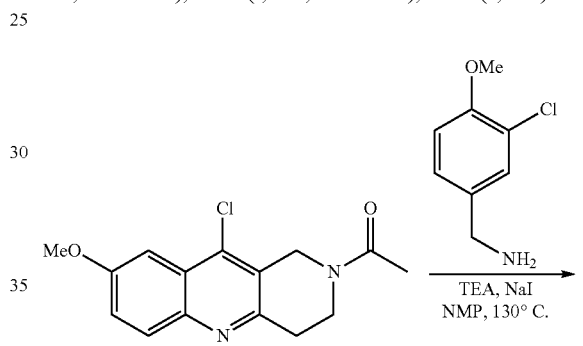

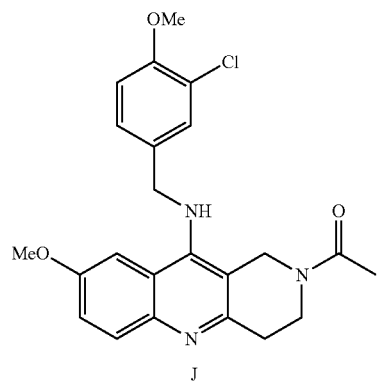

1-(10-((3-chloro-4-methoxybenzyl)amino)-8-methoxy-3,4-dihydrobenzo[b][1,6]naphthyridin-2(1H)-yl)ethan-1-one J A solution of 64 (0.15 mmol), 3-chloro-4-methoxybenzylamine hydrochloride (0.69 mmol), NaI (0.007 mmol), and triethylamine (0.69 mmol) in NMP (3.0 mL) was heated at 130° C. for 6 h. The solvent was evaporated off and the residue was purified by Flash Chromatography (AcOEt: MeOH 8:2) to give product J. MS ESI (m/z) 426 (M+H)$^+$. $^1$H NMR (400 MHz, CDCl$_3$) δ 7.86 (d, 1H, J=8.8 Hz), 7.37 (d, 1H, J=2.0 Hz), 7.29 (dd, 1H, J$_1$=2.8, J$_2$=9.6 Hz), 7.23

(dd, 1H, J$_1$=2.4, J$_2$=8.0 Hz), 7.15 (d, 1H, J=2.8 Hz), 6.91 (d, 1H, J=8.4 Hz), 4.73 (s, 2H), 4.53 (d, 2H, J=5.6 Hz), 3.90 (s, 4H), 3.80 (t, 2H, J=6.4 Hz), 3.75 (s, 3H), 3.18 (t, 2H, J=6.0 Hz), 2.21 (s, 3H).

The following general scheme can be used to prepare additional compounds in accordance with certain aspects of the invention:

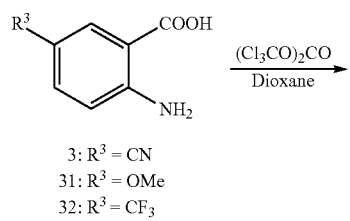

3: R$^3$ = CN
31: R$^3$ = OMe
32: R$^3$ = CF$_3$

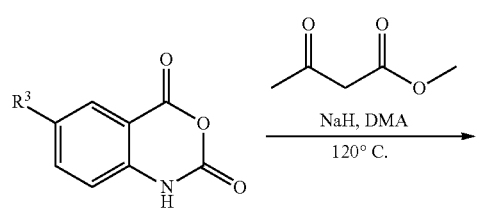

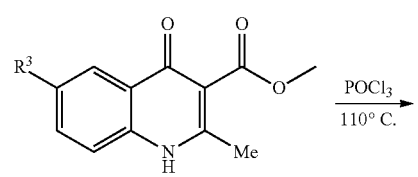

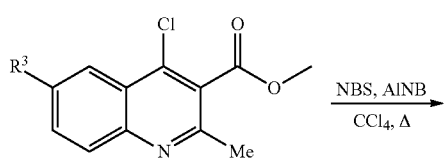

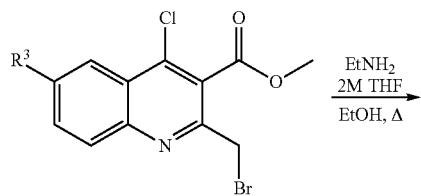

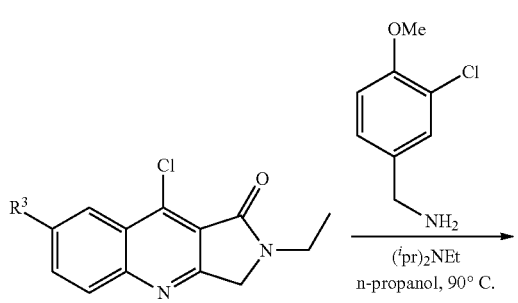

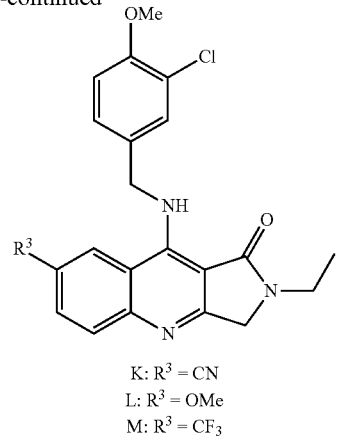

K: R$^3$ = CN
L: R$^3$ = OMe
M: R$^3$ = CF$_3$

Example 17

9-[(3-chloro-4-methoxybenzyl)amino]-2-ethyl-1-oxo-2,3-dihydro-1H-pyrrolo[3,4-b]quinoline-7-carbonitrile

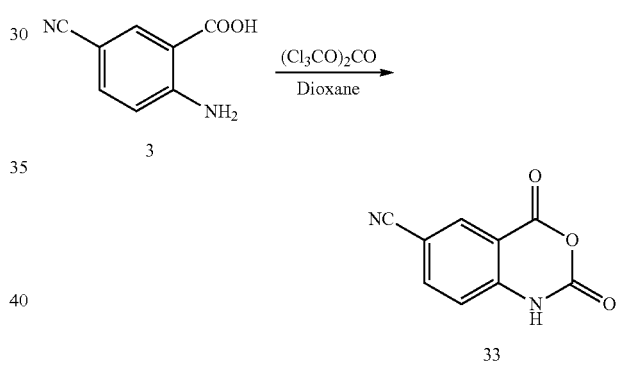

2,4-dioxo-1,4-dihydro-2H-benzo[d][1,3]oxazine-6-carbonitrile 33

(Cl$_3$CO)$_2$CO (3.08 mmol) was added to a suspension of 2-amino-5-cyanobenzoic acid 3 (9.25 mmol) in 1,4-dioxane at 0° C. The homogeneous reaction mixture was heated to 90° C. for 5 h and then cooled down. The resulting precipitate 33 was isolated by filtration. $^1$H NMR (400 MHz, DMSO-d$_6$) δ 12.15 (s, 1H), 8.38 (d, 1H, J=1.6 Hz), 8.11 (dd, 1H, J$_1$=1.6, J$_2$=8.8 Hz), 7.25 (d, 1H, J=8.4 Hz)

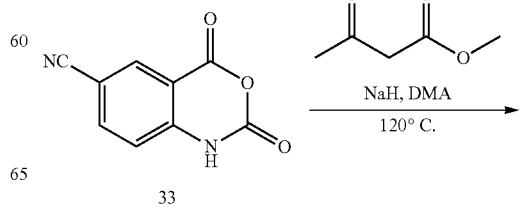

-continued

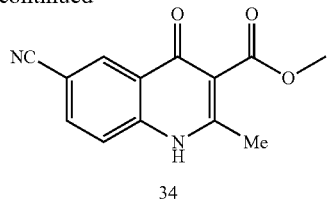

methyl 6-cyano-4-hydroxy-2-methyl-1,4-dihydro-quinoline-3-carboxylate 34

NaH (6.38 mmol) was added portionwise to a solution of methyl acetoacetate (6.38 mmol) in DMA (2 mL). Compound 33 (5.32 mmol) was added and the reaction mixture was stirred to 120° C. for 30 min. The solvent was reduced and water was added. The resulting precipitate 34 was collected by filtration. 1H NMR (400 MHz, DMSO-$d_6$) δ 12.25 (s, 1H), 8.39 (d, 1H, J=2.0 Hz), 8.01 (dd, 1H, $J_1$=2.0, $J_2$=8.8 Hz), 7.66 (d, 1H, J=8.8 Hz), 3.70 (s, 3H), 2.41 (s, 3H)

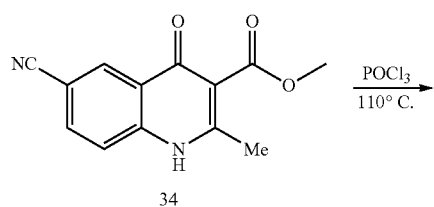

methyl 4-chloro-6-cyano-2-methylquinoline-3-carboxylate 35

Compound 34 (2.0 mmol) was suspended in $POCl_3$ (4 mL) and heated to 110° C. for 20 min. the homogeneous reaction mixture was slowly poured into iced $NH_3$ aq. The aqueous phase was extracted with AcOEt (3×50 mL). The organic layers were dried over $Na_2SO_4$, filtered and evaporated under reduce pressure to give the desire compound 35. MS ESI (m/z) 261 (M+H)$^+$; $^1$H NMR (400 MHz, CDCl$_3$) δ 8.61 (d, 1H, J=2.0 Hz), 8.12 (d, 1H, J=8.8 Hz), 7.92 (dd, 1H, $J_1$=1.6, $J_2$=8.4 Hz), 4.05 (s, 3H), 2.75 (s, 3H).

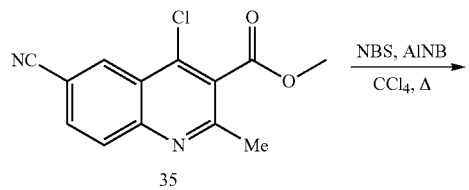

-continued

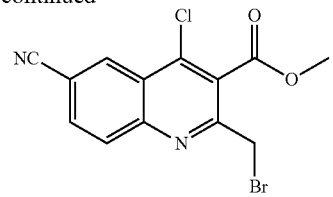

methyl 2-(bromomethyl)-4-chloro-6-cyanoquinoline-3-carboxylate 36

A solution of 35 (0.14 mmol), N-bromosuccinimide (0.22 mmol) and 2,2'-Azobis(2-methylpropionitrile) (0.03 mmol) in CCl$_4$ (1 mL) was heated to reflux for 4 h. The reaction mixture was cooled down and the solid was filtered off. The filtrate was concentrated and the residue was purified by flash chromatography (hexanes: AcOEt 9:1) to give the desired product 36.

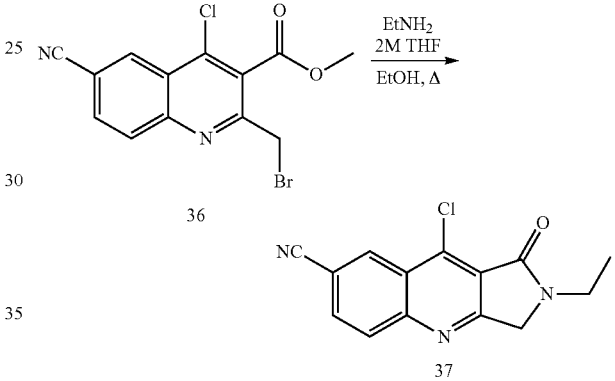

9-chloro-2-ethyl-1-oxo-2,3-dihydro-1H-pyrrolo[3,4-b]quinoline-7-carbonitrile 37

To a solution of 36 (0.15 mmol) in ethanol was added EtNH$_2$ (2M in THF, 0.46 mmol). The reaction mixture was heated to reflux for 2 h. The solvent was evaporated off and the residue was purified by flash chromatography (Hexanes: AcOEt 3:7) to give the desired product 37. MS ESI (m/z) 272 (M+H)$^+$; $^1$H NMR (400 MHz, CDCl$_3$) δ 8.84 (d, 1H, J=2.0 Hz), 8.23 (d, 1H, J=1.4 Hz), 7.99 (dd, 1H, $J_1$=1.6, $J_2$=8.8 Hz), 4.57 (s, 2H), 3.78 (q, 2H, J=7.2 Hz), 1.35 (t, 3H, J=6.8 Hz)

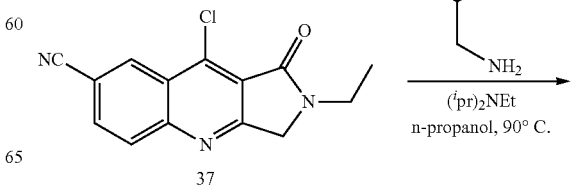

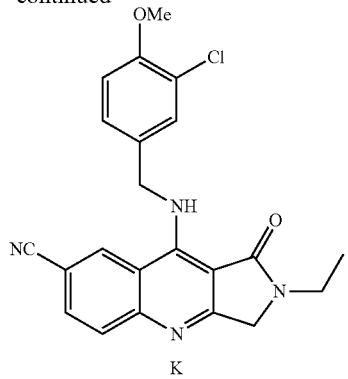

9-[(3-chloro-4-methoxybenzyl)amino]-2-ethyl-1-oxo-2,3-dihydro-1H-pyrrolo[3,4-b]quinoline-7-carbonitrile, K A solution of 37 (0.037 mmol), 3-chloro-4-methoxybenzylamine hydrochloride (0.055 mmol) and ($^i$pr)$_2$NEt (0.22 mmol) in n-propanol (1 mL) was heated to 90° C. for 1 h. After cooling down, the resulting precipitate K was collected by filtration. MS ESI (m/z) 407 (M+H)$^+$; $^1$H NMR (400 MHz, CDCl$_3$) δ 8.58 (t, 1H, J=6.0 Hz), 8.53 (d, 1H, J=1.6 Hz), 7.94 (d, 1H, J=9.2 Hz), 7.75 (dd, 1H, J$_1$=1.6, J$_2$=8.4 Hz), 7.42 (d, 1H, J=1.6 Hz), 7.30 (dd, 1H, J$_1$=2.4, J$_2$=8.4 Hz), 6.96 (d, 1H, J=8.4 Hz), 4.93 (d, 2H, J=5.6 Hz), 4.38 (s, 2H), 3.89 (s, 3H), 3.63 (q, 2H, J=7.2 Hz), 1.27 (t, 3H, J=7.2 Hz)

Example 18

9-((3-chloro-4-methoxybenzyl)amino)-2-ethyl-7-methoxy-2,3-dihydro-1H-pyrrolo[3,4-b]quinolin-1-one

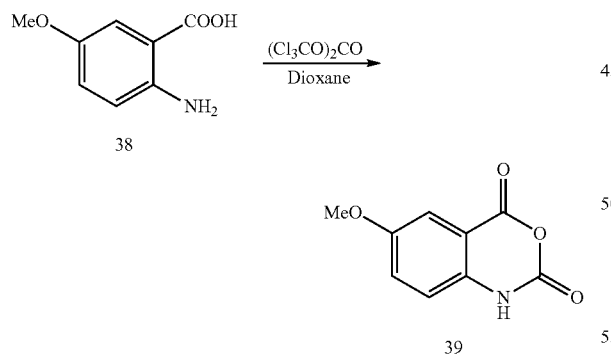

6-methoxy-2H-benzo[d][1,3]oxazine-2,4(1H)-dione 39

(Cl$_3$CO)$_2$CO (1.0 mmol) was added to a suspension of 2-amino-5-methoxybenzoic acid 38 (3.0 mmol) in 1,4-dioxane (3 mL) at 0° C. The homogeneous reaction mixture was heated to 90° C. for 2 h and then cooled down. The resulting precipitate 39 was isolated by filtration. MS ESI (m/z) 192 (M−1); $^1$H NMR (400 MHz, DMSO-d$_6$) δ 11.61 (s, 1H), 7.38 (dd, 1H, J$_1$=2.8, J$_2$=8.4 Hz), 7.34 (d, 1H, J=2.4 Hz), 7.11 (d, 1H, J=8.4 Hz), 3.80 (s, 3H)

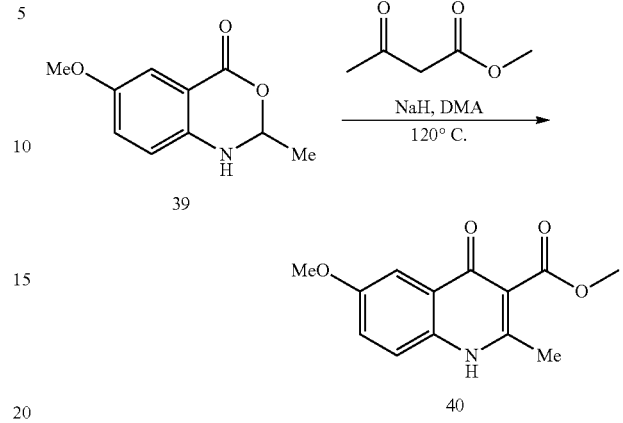

methyl 6-methoxy-2-methyl-4-oxo-1,4-dihydroquinoline-3-carboxylate 40

NaH (3.1 mmol) was added portionwise to a solution of methyl acetoacetate (3.1 mmol) in DMA (3 mL). Compound 39 (2.6 mmol) was added and the reaction mixture was stirred to 120° C. for 30 min. The solvent was reduced and water was added. The resulting precipitate 40 was collected by filtration. 1H NMR (400 MHz, DMSO-d$_6$) δ 11.87 (s, 1H), 7.49 (d, 1H, J=8.8 Hz), 7.45 (d, 1H, J=2.8 Hz), 7.31 (dd, 1H, J$_1$=3.2, J$_2$=8.8 Hz), 3.82 (s, 3H), 3.75 (s, 3H), 2.37 (s, 3H)

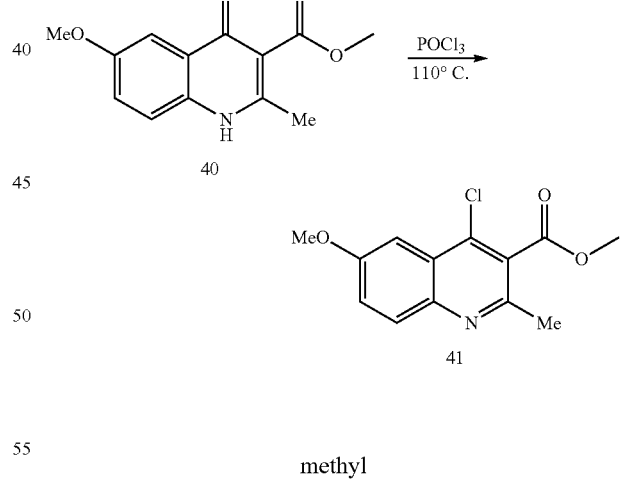

methyl 4-chloro-6-methoxy-2-methylquinoline-3-carboxylate 41

Compound 40 (1.62 mmol) was suspended in POCl$_3$ (3 mL) and heated to 110° C. for 30 min. the homogeneous reaction mixture was slowly poured into iced NH$_3$ aq. The aqueous phase was extracted with AcOEt (3×50 mL). The organic layers were dried over Na$_2$SO$_4$, filtered and evaporated under reduce pressure to give the desire compound 41. $^1$H NMR (400 MHz, CDCl$_3$) δ 7.93 (d, 1H, J=9.6 Hz), 7.43-7.41 (m, 2H), 4.03 (s, 3H), 3.97 (s, 3H), 2.67 (s, 3H).

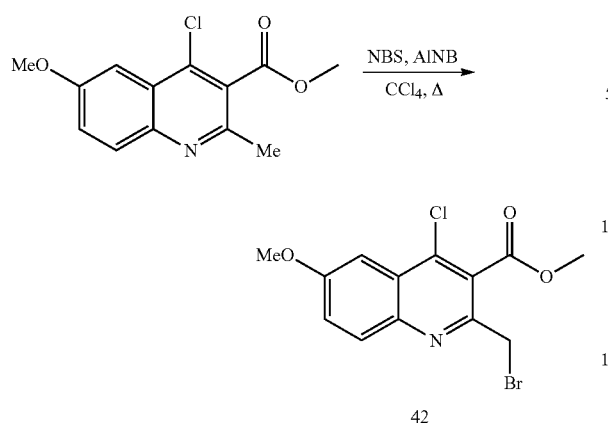

methyl 2-(bromomethyl)-4-chloro-6-methoxyquino-
line-3-carboxylate 42

A solution of 41 (1.47 mmol), N-bromosuccinimide (2.20 mmol) and 2,2'-Azobis(2-methylpropionitrile) (0.3 mmol) in CCl$_4$ (3 mL) was heated to reflux for 5 h. The reaction mixture was cooled down and the solid was filtered off. The filtrate was concentrated and the residue was purified by flash chromatography (hexanes: AcOEt 9:1) to give the desired product 42. $^1$H NMR (400 MHz, CDCl$_3$) δ 7.98 (d, 1H, J=10.4 Hz), 7.47-7.44 (m, 2H), 4.77 (s, 2H), 4.07 (s, 3H), 3.99 (s, 3H).

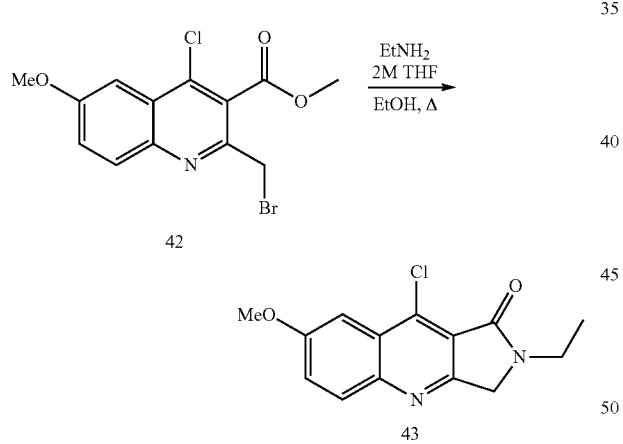

9-chloro-2-ethyl-7-methoxy-2,3-dihydro-1H-pyrrolo
[3,4-b]quinolin-1-one 43

To a solution of 42 (0.17 mmol) in ethanol (1 mL) was added EtNH$_2$ (2M in THF, 0.52 mmol). The reaction mixture was heated to reflux for 3 h. The solvent was evaporated off and the residue was purified by flash chromatography (Hexanes: AcOEt 3:7) to give the desired product 43. $^1$H NMR (400 MHz, CDCl$_3$) δ 8.01 (d, 1H, J=8.8 Hz), 7.64 (d, 1H, J=2.8 Hz), 7.50 (dd, 1H, J$_1$=2.8, J$_2$=9.6 Hz), 4.49 (s, 2H), 4.01 (s, 3H), 3.76 (q, 2H, J=7.2 Hz), 1.33 (t, 3H, J=7.2 Hz)

9-((3-chloro-4-methoxybenzyl)amino)-2-ethyl-7-
methoxy-2,3-dihydro-1H-pyrrolo[3,4-b]quinolin-1-
one L A solution of 43 (0.11 mmol), 3-chloro-4-methoxyben-zylamine hydrochloride (0.16 mmol) and ($^i$pr)$_2$NEt (0.66 mmol) in n-propanol (1.5 mL) was heated to 90° C. for 1 h. The solvent was evaporated off and the residue was purified by flash chromatography (AcOEt: MeOH 19:1) to give the final product L. MS ESI (m/z) 412 (M+H)$^+$; $^1$H NMR (400 MHz, CDCl$_3$) δ 8.14 (t, 1H, J=6.4 Hz), 7.85 (d, 1H, J=9.6 Hz), 7.48 (d, 1H, J=2.4 Hz), 7.37-7.29 (m, 3H), 6.95 (d, 1H, J=8.8 Hz), 4.95 (d, 2H, J=6.8 Hz), 4.38 (s, 2H), 3.90 (s, 3H), 3.66 (q, 2H, J=7.2 Hz), 3.59 (s, 3H), 1.28 (t, 3H, J=7.2 Hz)

Example 19

9-[(3-chloro-4-methoxybenzyl)amino]-2-ethyl-7-
(trifluoromethyl)-2,3-dihydro-1H-pyrrolo[3,4-b]
quinolin-1-one

6-(trifluoromethyl)-2H-benzo[d][1,3]oxazine-2,4 (1H)-dione 45

$(Cl_3CO)_2CO$ (1.3 mmol) was added to a suspension of 2-amino-5-(trifluoromethyl)benzoic acid 44 (3.9 mmol) in 1,4-dioxane (3 mL) at 0° C. The homogeneous reaction mixture was heated to 90° C. for 2 h and then cooled down. The resulting precipitate 45 was isolated by filtration. $^1$H NMR (400 MHz, DMSO-$d_6$) δ 12.09 (s, 1H), 8.14 (d, 1H, J=1.2 Hz), 8.07 (dd, 1H, $J_1$=1.6, $J_2$=8.8 Hz), 7.32 (d, 1H, J=8.8 Hz)

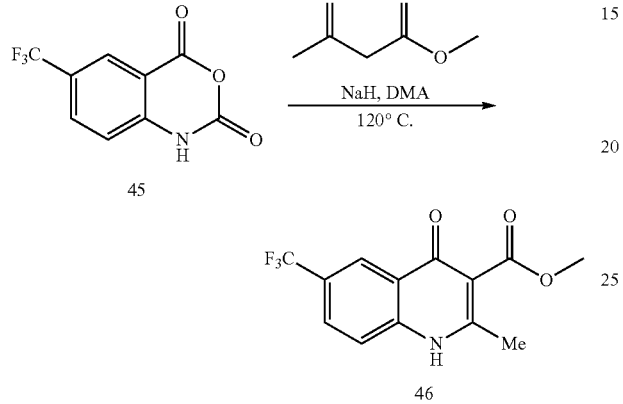

methyl 2-methyl-4-oxo-6-(trifluoromethyl)-1,4-dihydroquinoline-3-carboxylate 46

NaH (3.1 mmol) was added portionwise to a solution of methyl acetoacetate (3.1 mmol) in DMA (2 mL). Compound 45 (2.6 mmol) was added and the reaction mixture was stirred to 120° C. for 30 min. The solvent was reduced and water was added. The resulting precipitate 46 was collected by filtration. MS ESI (m/z) 286 (M+H)$^+$.

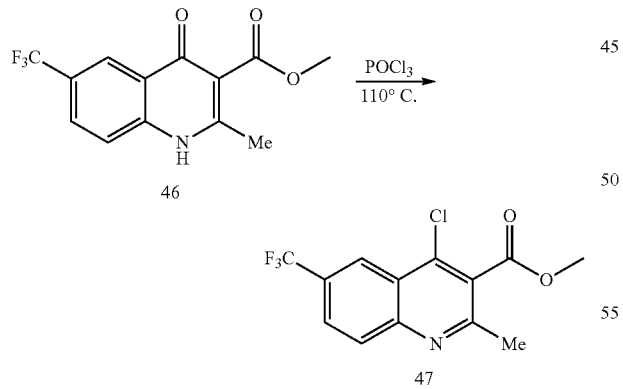

methyl 4-chloro-2-methyl-6-(trifluoromethyl)quinoline-3-carboxylate 47

Compound 46 (1.6 mmol) was suspended in POCl$_3$ (1 mL) and heated to 110° C. for 20 min. the homogeneous reaction mixture was slowly poured into iced NH$_3$ aq. The aqueous phase was extracted with AcOEt (3×50 mL). The organic layers were dried over Na$_2$SO$_4$, filtered and evaporated under reduce pressure to give the desire compound 47. MS ESI (m/z) 304 (M+H)$^+$.

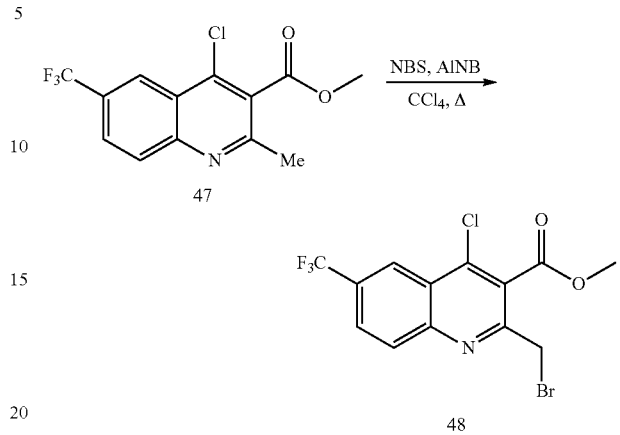

methyl 2-(bromomethyl)-4-chloro-6-(trifluoromethyl)quinoline-3-carboxylate 48

A solution of 47 (0.43 mmol), N-bromosuccinimide (0.64 mmol) and 2,2'-Azobis(2-methylpropionitrile) (0.03 mmol) in CCl$_4$ (2.0 mL) was heated to reflux for 4 h. The reaction mixture was cooled down and the solid was filtered off. The filtrate was concentrated and the residue was purified by flash chromatography (hexanes: AcOEt 9:1) to give the desired product 48.
MS ESI (m/z) 384 (M+H)$^+$; $^1$H NMR (400 MHz, CDCl$_3$) δ 8.58 (d, 1H, J=1.2 Hz), 8.22 (d, 1H, J=8.8 Hz), 8.01 (dd, 1H, $J_1$=2.0, $J_2$=8.8 Hz), 4.77 (s, 2H), 4.06 (s, 3H).

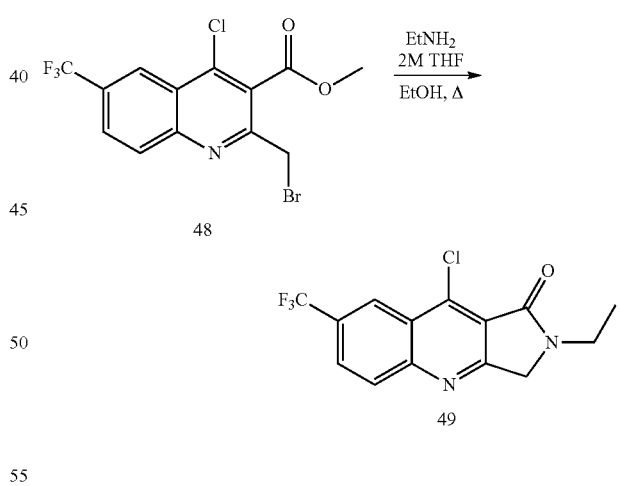

9-chloro-2-ethyl-7-(trifluoromethyl)-2,3-dihydro-1H-pyrrolo[3,4-b]quinolin-1-one 49

To a solution of 48 (0.21 mmol) in ethanol was added EtNH$_2$ (2M in THF, 0.63 mmol). The reaction mixture was heated to reflux for 2.5 h. The solvent was evaporated off and the residue was purified by flash chromatography (Hexanes: AcOEt 1:1) to give the desired product 49.
MS ESI (m/z) 315 (M+H)$^+$; $^1$H NMR (400 MHz, CDCl$_3$) δ 8.76 (s, 1H), 8.26 (d, 1H, J=8.8 Hz), 8.03 (dd, 1H, $J_1$=2.0, $J_2$=8.8 Hz), 4.57 (s, 2H), 3.79 (q, 2H, J=6.8 Hz), 1.35 (t, 3H, J=6.8 Hz)

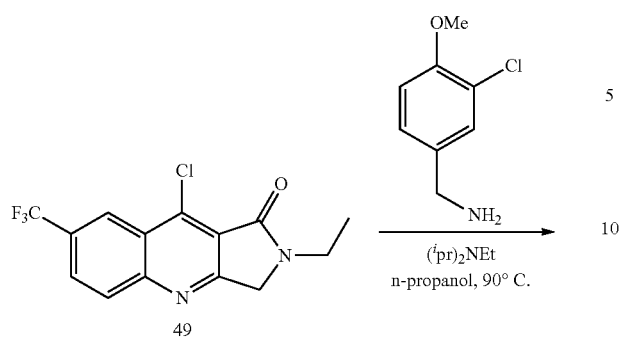

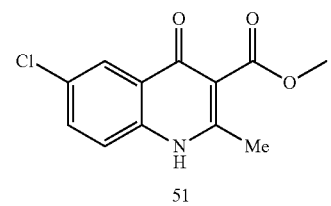

methyl 6-chloro-2-methyl-4-oxo-1,4-dihydroquinoline-3-carboxylate 51

NaH (9.1 mmol) was added portionwise to a solution of methyl acetoacetate (9.1 mmol) in DMA (2 mL). Compound 50 (7.6 mmol) was added and the reaction mixture was stirred to 120° C. for 30 min. The solvent was reduced and water was added. The resulting precipitate 51 was collected by filtration. 1H NMR (400 MHz, DMSO-$d_6$) δ 12.07 (s, 1H), 7.98 (d, 1H, J=2.4 Hz), 7.71 (dd, 1H, $J_1$=2.4, $J_2$=8.4 Hz), 7.57 (d, 1H, J=8.8 Hz), 3.76 (s, 3H), 2.39 (s, 3H).

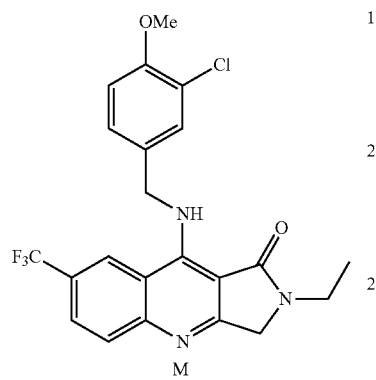

9-[(3-chloro-4-methoxybenzyl)amino]-2-ethyl-7-(trifluoromethyl)-2,3-dihydro-1H-pyrrolo[3,4-b]quinolin-1-one M A solution of 49 (0.095 mmol), 3-chloro-4-methoxybenzylamine hydrochloride (0.14 mmol) and ($^i$pr)$_2$NEt (0.57 mmol) in n-propanol (1.0 mL) was heated to 90° C. for 1 h. The solvent was evaporated off and the residue was purified by flash chromatography (AcOEt) to give the final product M. MS ESI (m/z) 450 (M+H)$^+$; $^1$H NMR (400 MHz, CDCl$_3$) δ 8.58 (t, 1H, J=6.0 Hz), 8.46 (s, 1H), 8.0 (d, 1H, J=8.8 Hz), 7.80 (dd, 1H, $J_1$=2.0, $J_2$=9.2 Hz), 7.45 (d, 1H, J=2.0 Hz), 7.32 (dd, 1H, $J_1$=2.4, $J_2$=8.4 Hz), 6.95 (d, 1H, J=8.0 Hz), 4.95 (d, 2H, J=6.0 Hz), 4.41 (s, 2H), 3.90 (s, 3H), 3.67 (q, 2H, J=7.2 Hz), 1.3 (t, 3H, J=7.2 Hz)

Example 20

7-chloro-9-[(3-chloro-4-methoxybenzyl)amino]-2-ethyl-2,3-dihydro-1H-pyrrolo[3,4-b]quinolin-1-one

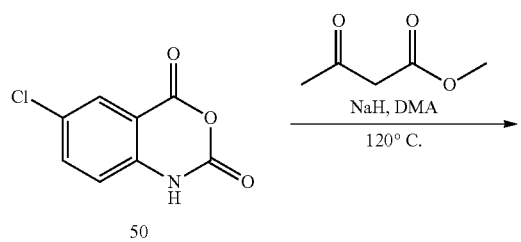

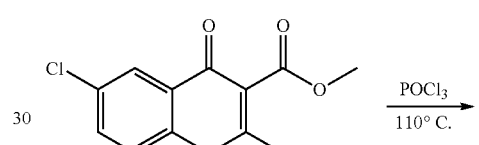

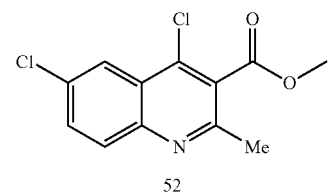

methyl 4,6-dichloro-2-methylquinoline-3-carboxylate 52

Compound 51 (3.0 mmol) was suspended in POCl$_3$ (4 mL) and heated to 110° C. for 20 min. the homogeneous reaction mixture was slowly poured into iced NH$_3$ aq. The aqueous phase was extracted with AcOEt (3×50 mL). The organic layers were dried over Na$_2$SO$_4$, filtered and evaporated under reduce pressure to give the desire compound 52. $^1$H NMR (400 MHz, DMSO-$d_6$) δ 8.21 (d, 1H, J=2.4 Hz), 8.08 (d, 1H, J=9.2 Hz), 7.95 (dd, 1H, $J_1$=2.4, $J_2$=8.8 Hz), 4.01 (s, 3H), 2.63 (s, 3H).

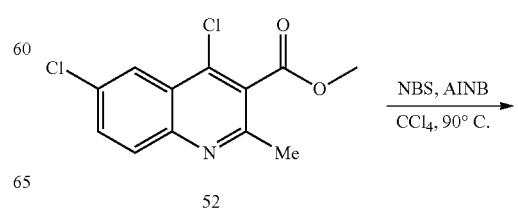

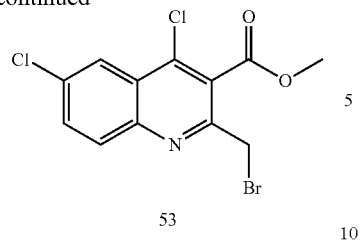

methyl 2-(bromomethyl)-4,6-dichloroquinoline-3-carboxylate 53

A solution of 52 (1.5 mmol), N-bromosuccinimide (3.0 mmol) and 2,2'-Azobis(2-methylpropionitrile) (0.3 mmol) in CCl$_4$ (1 mL) was heated to reflux for 4 h. The reaction mixture was cooled down and the solid was filtered off. The filtrate was concentrated and the residue was purified by flash chromatography (hexanes: AcOEt 2:1) to give the desired product 53. $^1$H NMR (400 MHz, CDCl$_3$) δ 8.26 (d, 1H, J=2.0 Hz), 8.04 (d, 1H, J=8.4 Hz), 7.78 (dd, 1H, J$_1$=2.4, J$_2$=8.8 Hz), 4.78 (s, 2H), 4.08 (s, 3H).

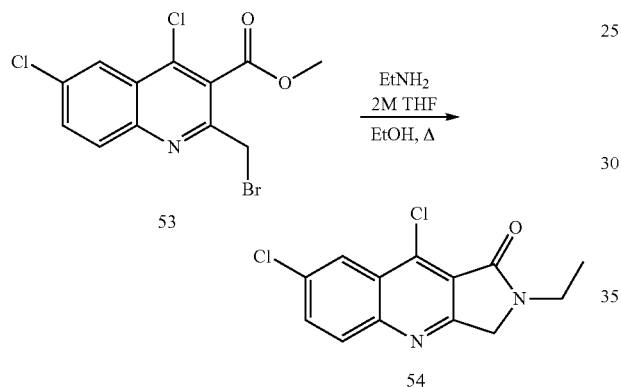

7,9-dichloro-2-ethyl-2,3-dihydro-1H-pyrrolo[3,4-b]quinolin-1-one 54

To a solution of 53 (0.41 mmol) in ethanol was added EtNH$_2$ (2M in THF, 1.24 mmol). The reaction mixture was heated to reflux for 2 h. The solvent was evaporated off and the residue was purified by flash chromatography (Hexanes: AcOEt 3:7) to give the desired product 54.

MS ESI (m/z) 281 (M+H)$^+$; $^1$H NMR (400 MHz, CDCl$_3$) δ 8.43 (d, 1H, J=2.0 Hz), 8.07 (d, 1H, J=8.8 Hz), 7.79 (dd, 1H, J$_1$=2.4, J$_2$=8.8 Hz), 4.52 (s, 2H), 3.78 (q, 2H, J=7.6 Hz), 1.33 (t, 3H, J=7.6 Hz).

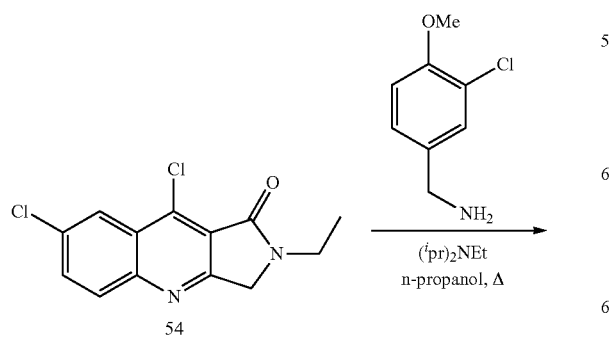

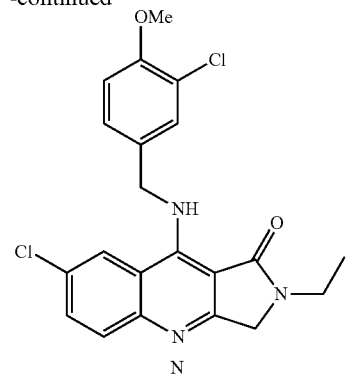

7-chloro-9-[(3-chloro-4-methoxybenzyl)amino]-2-ethyl-2,3-dihydro-1H-pyrrolo[3,4-b]quinolin-1-one N A solution of 54 (0.18 mmol), 3-chloro-4-methoxybenzylamine hydrochloride (0.27 mmol) and ($^i$pr)$_2$NEt (1.08 mmol) in n-propanol (1 mL) was heated to 90° C. for 2 h. After cooling down, the resulting precipitate N was collected by filtration. MS ESI (m/z) 416 (M+H)$^+$; $^1$H NMR (400 MHz, CDCl$_3$) δ 8.29 (t, 1H, J=5.6 Hz), 8.14 (d, 1H, J=2.0 Hz), 7.86 (d, 1H, J=9.2 Hz), 7.58 (dd, 1H, J$_1$=2.0, J$_2$=9.2 Hz), 7.45 (d, 1H, J=1.2 Hz), 7.32 (d, 1H, J=8.8 Hz), 6.95 (d, 1H, J=8.4 Hz), 4.93 (d, 2H, J=6.0 Hz), 4.37 (s, 2H), 3.91 (s, 3H), 3.64 (q, 2H, J=7.6 Hz), 1.28 (t, 3H, J=7.2 Hz).

Example 21

9-[(3-chloro-4-methoxybenzyl)amino]-2-ethyl-2,3-dihydro-1H-pyrrolo[3,4-b]quinolin-1-one

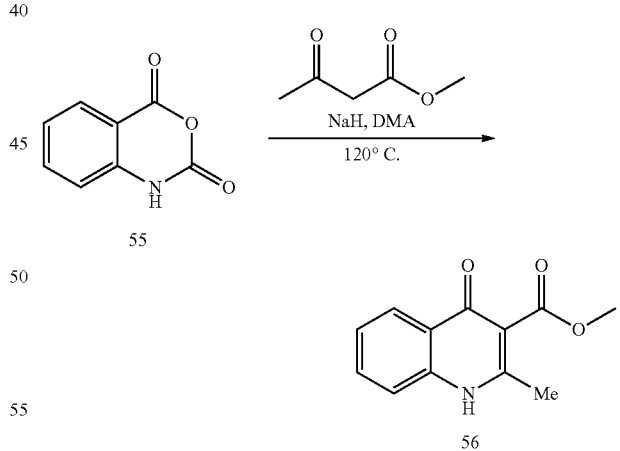

methyl 2-methyl-4-oxo-1,4-dihydroquinoline-3-carboxylate 56

NaH (7.35 mmol) was added portionwise to a solution of methyl acetoacetate (7.35 mmol) in DMA (2.0 mL). N-methylisatoic anhydride 55 (6.13 mmol) was added and the reaction mixture was stirred to 120° C. for 30 min. The solvent was reduced and water was added. The resulting precipitate 56 was collected by filtration. MS ESI (m/z) 218 (M+H)+; 1H NMR (400 MHz, DMSO-d6) δ 11.88 (s, 1H), 8.05 (d, 1H, J=8.0 Hz), 7.69-7.65 (m, 1H), 7.53 (d, 1H, J=8.4 Hz), 7.36 (m, 1H), 3.76 (s, 3H), 2.39 (s, 3H).

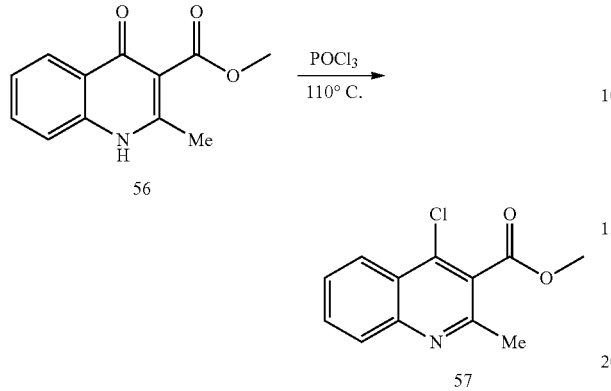

methyl 4-chloro-2-methylquinoline-3-carboxylate 57

Compound 56 (3.9 mmol) was suspended in POCl3 (3.0 mL) and heated to 110° C. for 30 min. the homogeneous reaction mixture was slowly poured into iced NH3 aq. The aqueous phase was extracted with AcOEt (3×50 mL). The organic layers were dried over Na2SO4, filtered and evaporated under reduce pressure to give the desire compound 57. MS ESI (m/z) 236 (M+H)+; 1H NMR (400 MHz, CDCl3) δ 8.4 (d, 1H, J=8.4 Hz), 8.03 (d, 1H, J=8.4 Hz), 7.79 (td, 1H, J1=1.2, J2=7.2), 7.63 (t, 1H, J=8.4), 4.04 (s, 3H), 2.72 (s, 3H).

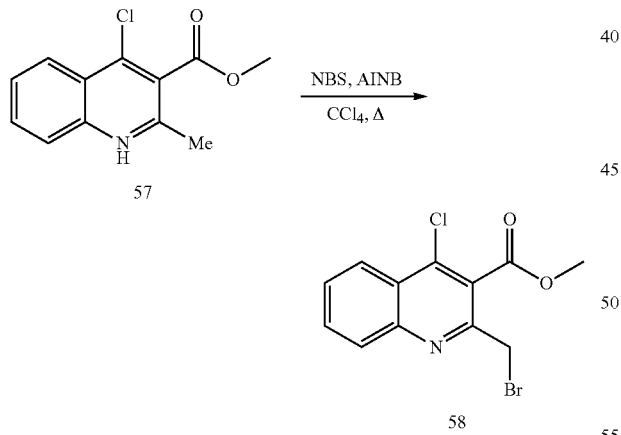

methyl 2-(bromomethyl)-4-chloroquinoline-3-carboxylate 58

A solution of 57 (3.44 mmol), N-bromosuccinimide (5.15 mmol) and 2,2'-Azobis(2-methylpropionitrile) (0.7 mmol) in CCl4 (4.0 mL) was heated to reflux for 4 h. The reaction mixture was cooled down and the solid was filtered off. The filtrate was concentrated and the residue was purified by flash chromatography (hexanes: AcOEt 2:1) to give the desired product 58. MS ESI (m/z) 315 (M+H)+; 1H NMR (400 MHz, CDCl3) δ 8.28 (dd, 1H, J1=1.2, J2=8.0 Hz), 8.09 (d, 1H, J=8.0 Hz), 7.86-7.82 (m, 1H), 7.73-7.68 (m, 1H), 4.80 (s, 2H), 4.08 (s, 3H).

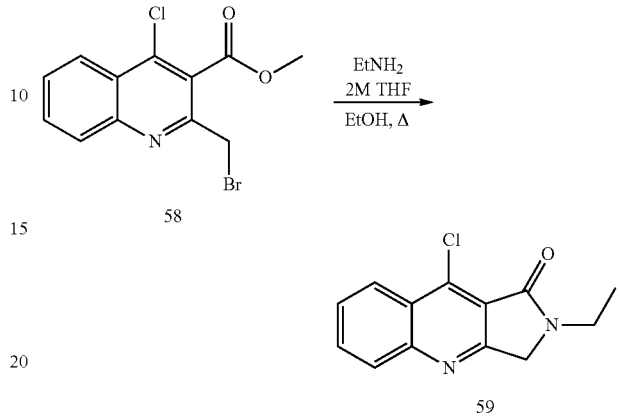

9-chloro-2-ethyl-2,3-dihydro-1H-pyrrolo[3,4-b]quinolin-1-one 59

To a solution of 58 (0.26 mmol) in ethanol (1 mL) was added EtNH2 (2M in THF, 0.76 mmol). The reaction mixture was heated to reflux for 2 h. The solvent was evaporated off and the residue was purified by flash chromatography (Hexanes: AcOEt 3:7) to give the desired product 59. MS ESI (m/z) 247 (M+H)+; 1H NMR (400 MHz, CDCl3) δ 8.46 (d, 1H, J=8.4 Hz), 8.13 (d, 1H, J=8.4 Hz), 7.87 (m, 1H), 7.72 (m, 1H), 4.53 (s, 2H), 3.77 (q, 2H, J=7.2 Hz), 1.34 (t, 3H, J=7.2 Hz).

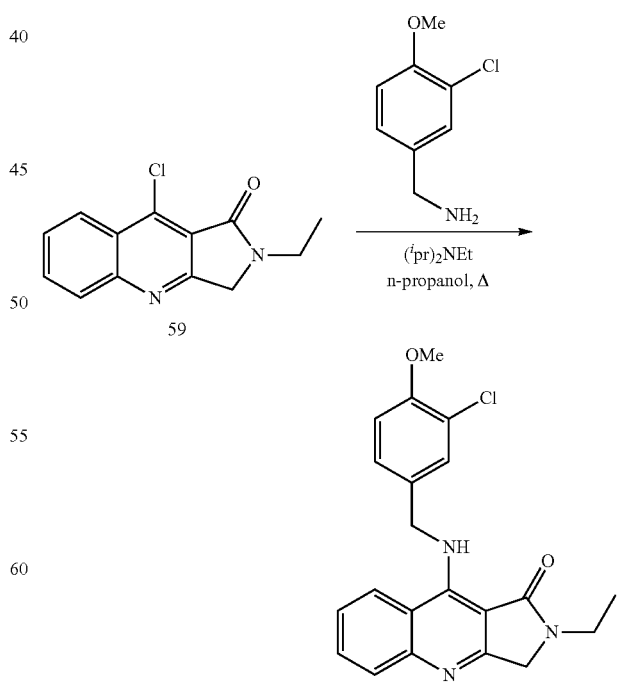

9-[(3-chloro-4-methoxybenzyl)amino]-2-ethyl-2,3-dihydro-1H-pyrrolo[3,4-b]quinolin-1-one O A solution of 59 (0.22 mmol), 3-chloro-4-methoxybenzylamine hydrochloride (0.33 mmol) and ($^i$pr)$_2$NEt (1.31 mmol) in n-propanol (2.0 mL) was heated to 90° C. for 2 h. After cooling down, the resulting precipitate O was collected by filtration. MS ESI (m/z) 382 (M+H); $^1$H NMR (400 MHz, CDCl$_3$) δ 8.26 (t, 1H, J=6.0 Hz), 8.14 (dd, 1H, J$_1$=1.2, J$_2$=8.0 Hz), 7.94 (dd, 1H, J$_1$=1.2, J$_2$=8.8 Hz), 7.68-7.64 (m, 1H), 7.45 (d, 1H, J=2.4 Hz), 7.33-7.29 (m, 1H), 6.95 (d, 1H, J=8.4 Hz), 4.98 (d, 2H, J=5.6 Hz), 4.39 (s, 2H), 3.90 (s, 3H), 3.65 (q, 2H, J=7.6 Hz), 1.29 (t, 3H, J=7.6 Hz).

Example 22

2-(tert-butyl)-9-[(3-chloro-4-methoxybenzyl)amino]-2,3-dihydro-1H-pyrrolo[3,4-b]quinolin-1-one

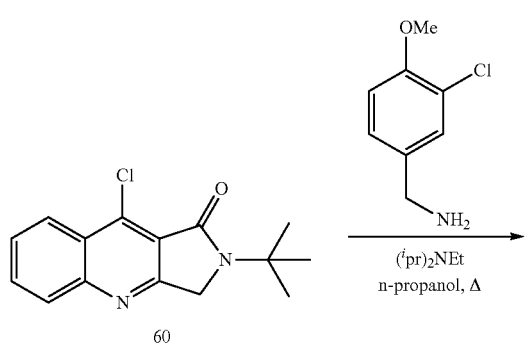

2-(tert-butyl)-9-chloro-2,3-dihydro-1H-pyrrolo[3,4-b]quinolin-1-one 60

To a solution of 58 (0.32 mmol) in ethanol (2.0 mL) was added tert-butylamine (2M in THF, 0.95 mmol). The reaction mixture was heated to reflux for 2 h. The solvent was evaporated off and the residue was purified by flash chromatography (Hexanes: AcOEt 3:7) to give the desired product 60. $^1$H NMR (400 MHz, CDCl$_3$) δ 8.46 (dd, 1H, J$_1$=1.2, J$_2$=8.4 Hz), 8.12 (d, 1H, J=8.8 Hz), 7.88-7.84 (m, 1H), 7.73-7.69 (m, 1H), 4.60 (s, 2H), 1.63 (s, 9H).

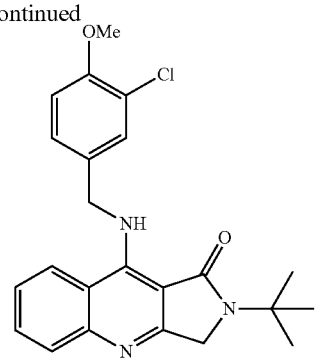

2-(tert-butyl)-9-[(3-chloro-4-methoxybenzyl)amino]-2,3-dihydro-1H-pyrrolo[3,4-b]quinolin-1-one P A solution of 60 (0.07 mmol), 3-chloro-4-methoxybenzylamine hydrochloride (0.11 mmol) and ($^i$pr)$_2$NEt (0.44 mmol) in n-propanol (1.0 mL) was heated to 90° C. for 2 h. After cooling down, the resulting precipitate P was collected by filtration. MS ESI (m/z) 410 (M+H)$^+$; $^1$H NMR (400 MHz, CDCl$_3$) δ 8.53 (t, 1H, J=6.4 Hz), 8.10 (d, 1H, J=8.4 Hz), 7.92 (d, 1H, J=8.0 Hz), 7.63 (t, 1H, J=7.6 Hz), 7.45 (d, 1H, J=2.0 Hz), 7.33-7.25 (m, 2H), 6.94 (d, 1H, J=8.8 Hz), 4.95 (d, 2H, J=6.8 Hz), 4.46 (s, 2H), 1.57 (s, 9H).

Compounds exhibited PDE5 inhibition in the nanomolar range or below. Exemplary inhibition of representative compounds is shown in Table 3.

TABLE 3

PDE5 Inhibition of Representative Compounds.

| Entry | Structure | Cmpd | PDE5 IC$_{50}$ (nM) |
|---|---|---|---|
| 11 | 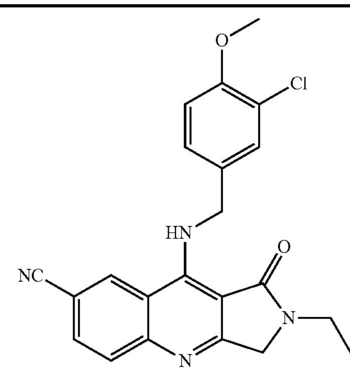 | K | 0.059 |
| 12 | 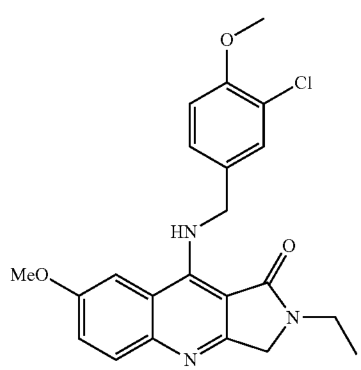 [SMILES: CCN1Cc2nc3ccc(OC)cc3c(NCc3ccc(OC)c(Cl)c3)c2C1=O] | L | 3.8 |

TABLE 3-continued

PDE5 Inhibition of Representative Compounds.

| Entry | Structure | Cmpd | PDE5 IC$_{50}$ (nM) |
|---|---|---|---|
| 13 | 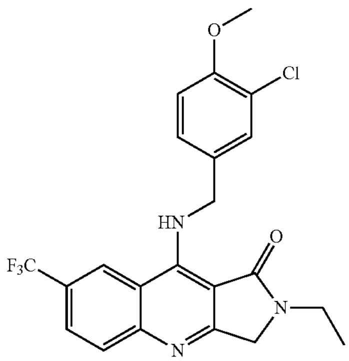 [SMILES: CCN1Cc2nc3ccc(C(F)(F)F)cc3c(NCc3ccc(OC)c(Cl)c3)c2C1=O] | M | 0.29 |
| 14 | 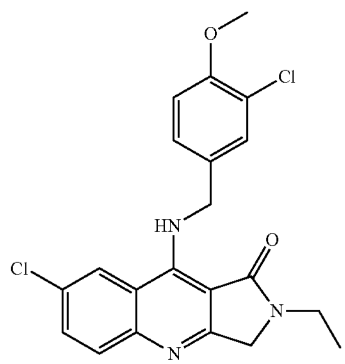 [SMILES: CCN1Cc2nc3ccc(Cl)cc3c(NCc3ccc(OC)c(Cl)c3)c2C1=O] | N | 1.7 |
| 15 | 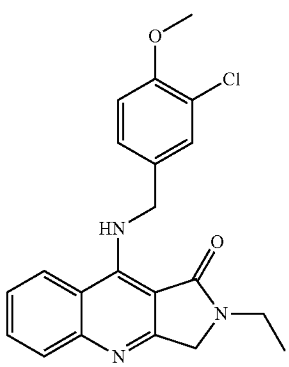 [SMILES: CCN1Cc2nc3ccccc3c(NCc3ccc(OC)c(Cl)c3)c2C1=O] | O | 64.0 |
| 16 | 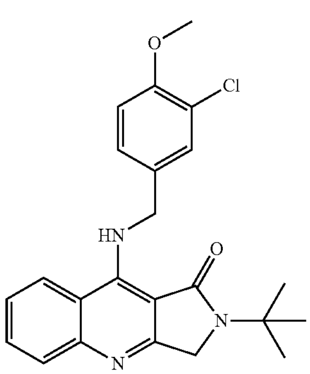 [SMILES: COc1ccc(CNc2c3c(nc4ccccc24)CN(C(C)(C)C)C3=O)cc1Cl] | P | 333.0 |

Example 23

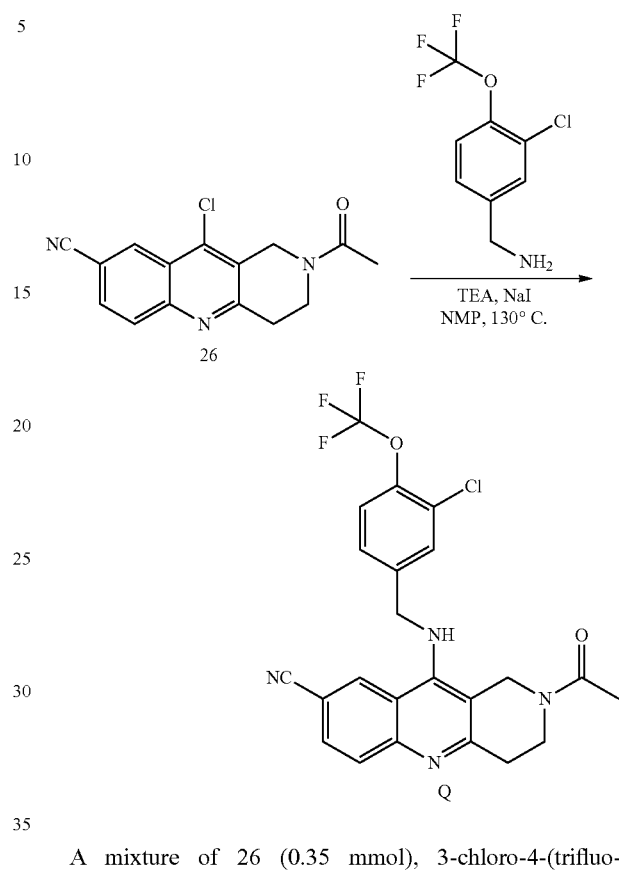

A mixture of 26 (0.35 mmol), 3-chloro-4-(trifluoromethoxy)benzyl amine (1.05 mmol), TEA (1.05 mmol) and NaI (0.035 mmol) in NMP (2 mL) was heated to 130° C. and stirred for 24 h. The mixture was diluted with AcOEt (10 mL) and washed with H$_2$O (2×10 mL). The organic layers were dried over Na$_2$SO$_4$, filtered and evaporated under reduce pressure. Flash Chromatography (eluent: 5% MeOH in AcOEt) gave the desired product Q (37% yield). MS ESI (m/z) 475 (M+H)$^+$; $^1$H NMR (400 MHz, CDCl$_3$) δ 8.38 (s, 1H), 8.07 (s, 1H), 7.77 (dd, 1H, J$_1$=1.6, J$_2$=8.4 Hz), 7.49 (d, 1H, J=2.0 Hz), 7.35 (dd, 1H, J$_1$=0.8, J$_2$=8.4 Hz), 7.30 (dd, 1H, J$_1$=2.4, J$_2$=8.4 Hz), 4.75 (s, 5H), 3.83 (t, 2H, J=6.4 Hz), 3.27 (s, 2H), 2.2 (s, 3H).

Example 24

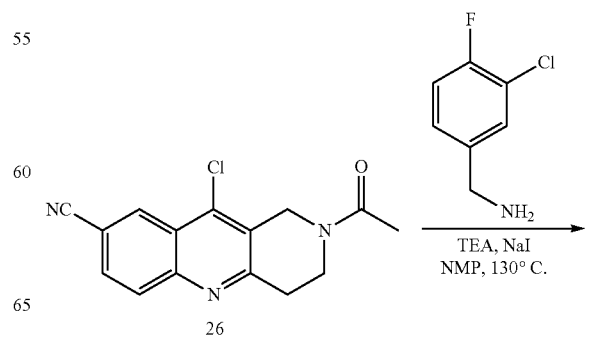

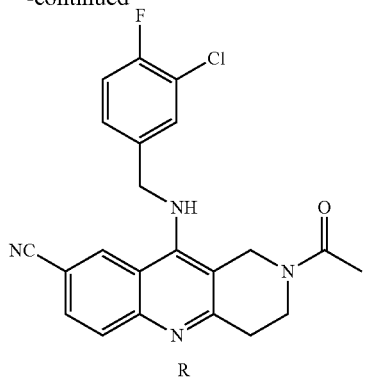

R

A mixture of 26 (0.28 mmol), 3-chloro-4-fluorobenzyl amine (0.84 mmol), TEA (0.84 mmol) and NaI (0.028 mmol) in NMP (2 mL) was heated to 130° C. and stirred for 24 h. The mixture was diluted with AcOEt (10 mL) and washed with H₂O (2×10 mL). The organic layers were dried over Na₂SO₄, filtered and evaporated under reduce pressure. Flash Chromatography (eluent: 5% MeOH in AcOEt) gave the desired product R (18% yield). MS ESI (m/z) 409 (M+H)⁺; ¹H NMR (400 MHz, CDCl₃) δ 8.34 (s, 1H), 8.03 (s, 1H), 7.74-7.71 (m, 1H), 7.36 (dd, 1H, $J_1$=2.4, $J_2$=7.2 Hz), 7.20-7.12 (m, 2H), 4.70 (s, 4H), 4.63 (s, 1H), 3.79 (t, 2H, J=6 Hz), 3.24 (s, 2H), 2.18 (s, 3H).

Example 25

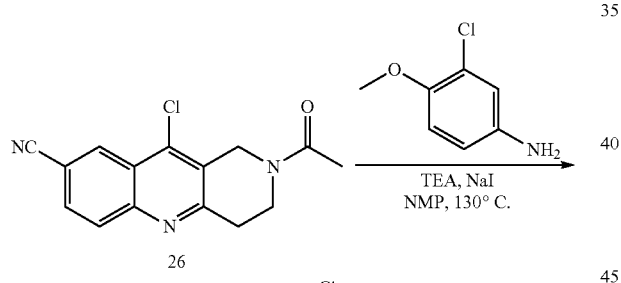

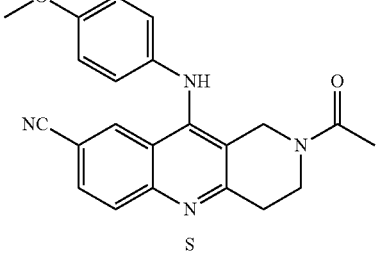

S

A mixture of 26 (0.27 mmol), 3-chloro-4-methoxyaniline (0.82 mmol), TEA (0.82 mmol) and NaI (0.027 mmol) in NMP (2 mL) was heated to 130° C. and stirred overnight. The mixture was diluted with AcOEt (10 mL) and washed with H₂O (2×10 mL). The organic layers were dried over Na₂SO₄, filtered and evaporated under reduce pressure. Flash Chromatography (eluent: 5% MeOH in AcOEt) gave the desired product S (14% yield). MS ESI (m/z) 407 (M+H)⁺.

Example 26

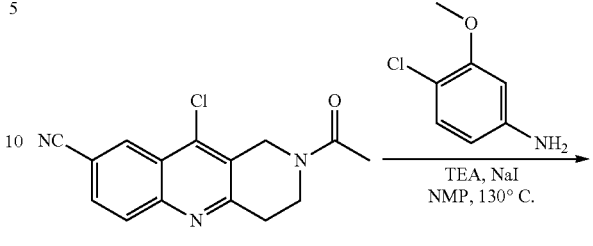

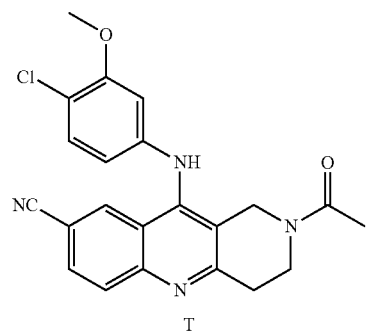

T

A mixture of 26 (0.25 mmol), 3-chloro-4-methoxyaniline (0.75 mmol), TEA (0.75 mmol) and NaI (0.025 mmol) in NMP (2 mL) was heated to 130° C. and stirred overnight. The mixture was diluted with AcOEt (10 mL) and washed with H₂O (2×10 mL). The organic layers were dried over Na₂SO₄, filtered and evaporated under reduce pressure. Flash Chromatography (eluent: 5% MeOH in AcOEt) gave the desired product T (10% yield). MS ESI (m/z) 407 (M+H)⁺.

Example 27

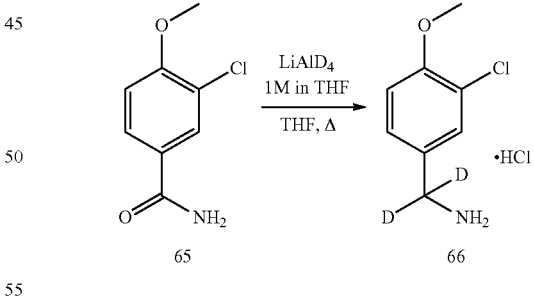

LiAlD₄ was added slowly to a solution of 65 in THF (2 mL) at 0° C. The solution was heated to 70° C. for 2 h. The reaction mixture was quenched by adding NaOH 1M at 0° C. The aqueous phase was extracted with AcOEt (3×10 mL), dried over Na₂SO₄, filtered and evaporated under reduce pressure. The residue was treated with HCl 2M in diethyl ether and the resulting precipitate (66) was collected by filtration (80% yield). 1H NMR (400 MHz, DMSO-d₆) δ 8.37 (s, 3H), 7.61 (d, 1H, J=2.4 Hz), 7.45-7.42 (m, 1H), 7.18 (d, 1H, J=8.8 Hz), 3.95 (s, 2H), 3.86 (s, 3H).

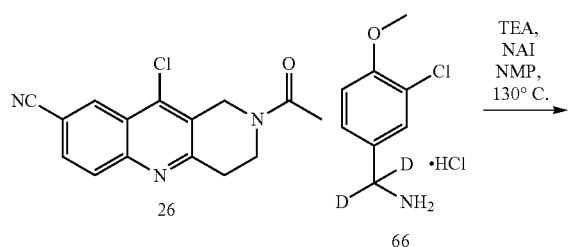

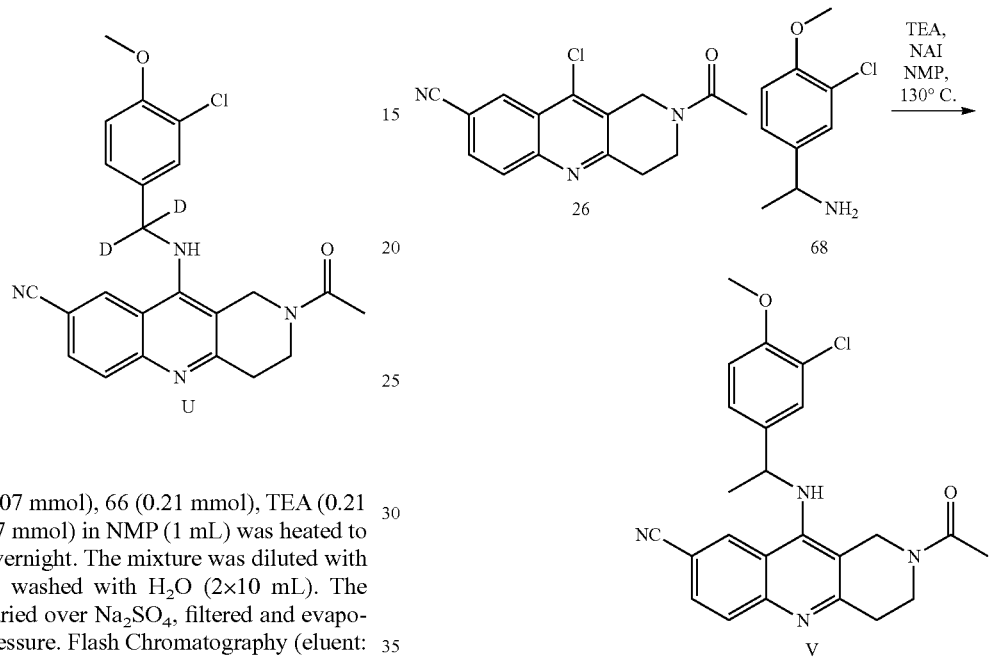

A mixture of 26 (0.07 mmol), 66 (0.21 mmol), TEA (0.21 mmol) and NaI (0.007 mmol) in NMP (1 mL) was heated to 130° C. and stirred overnight. The mixture was diluted with AcOEt (10 mL) and washed with H₂O (2×10 mL). The organic layers were dried over Na₂SO₄, filtered and evaporated under reduce pressure. Flash Chromatography (eluent: 2% MeOH in DCM) gave the desired product U (12% yield). MS ESI (m/z) 423 (M+H)⁺; ¹H NMR (400 MHz, CDCl₃) δ 8.35 (s, 1H), 7.97 (d, 1H, J=8.8 Hz), 7.74 (dd, 1H, J₁=1.8, J₂=9.0 Hz), 7.31 (d, 1H, J=2.0 Hz), 7.21 (dd, 1H, J₁=2.0, J₂=8.4 Hz), 6.94 (d, 1H, J=8.0 Hz), 4.71 (s, 2H, CH₂), 4.56 (s, 1H, NH), 3.92 (s, 3H, OCH₃), 3.82 (t, 2H, J=6.4 Hz, CH₂), 3.21 (t, 2H, J=6.4 Hz, CH₂), 2.22 (s, 3H, COCH₃).

Substitution of H with D as shown in compound U led to the formation of only 1 metabolite instead of three.

Example 28

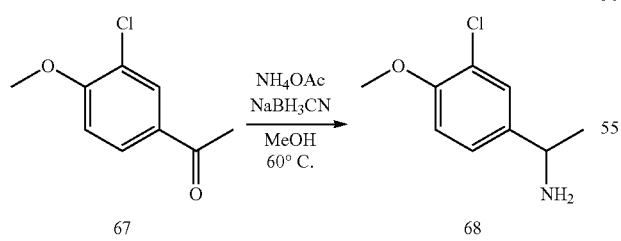

NaBH₃CN (10.52 mmol) was added to a solution of 67 (5.26 mmol) and NH₄OAc (52.6 mmol) in MeOH (15 mL). The reaction mixture was stirred overnight at 60° C. and then cooled to room temperature and partitioned between AcOEt (50 mL) and H₂O (50 mL). The aqueous layer was discarded and the organic phase was washed with water (2×50 mL), dried over Na₂SO₄, filtered and evaporated under reduce pressure to yield compound 68 (61%). ¹H NMR (400 MHz, CDCl₃) δ 7.37 (d, 1H, J=2.0 Hz), 7.20 (dd, 1H, J₁=2.0, J₂=8.4 Hz), 6.88 (d, 1H, J=8.0 Hz), 4.07 (q, 1H, J=6.4 Hz, CHCH₃), 3.88 (s, 3H, OCH₃), 1.84 (br s, 2H, NH₂), 1.36 (d, 3H, J=6.4 Hz, CHCH₃).

A mixture of 26 (0.175 mmol), 68 (0.526 mmol), TEA (0.7 mmol) and NaI (0.017 mmol) in NMP (1 mL) was heated to 130° C. and stirred overnight. The mixture was cooled down and AcOEt (10 mL) was added. The organic layer was washed with H₂O (2×10 mL), dried over Na₂SO₄, filtered and evaporated under reduce pressure. Flash Chromatography (eluent: 2% MeOH in DCM) gave the desired product V (17% yield). MS ESI (m/z) 435 (M+H)⁺; ¹H NMR (400 MHz, CDCl₃) δ 8.29 (S, 1H), 7.94 (d, 1H, J=8.4 Hz), 7.72 (d, 1H, J=8.8 Hz), 7.25 (s, 1H), 7.16 (d, 1H, J=8.8 Hz), 6.88 (d, 1H, J=8.4 Hz), 4.86 (t, 1H, J=6.8 Hz, NH), 4.71 (s, 2H, CH₂), 3.88 (s, 3H, OCH₃), 3.84-3.72 (m, 3H, CH₂ and CH), 3.18 (t, 2H, J=5.6 Hz, CH₂), 2.22 (s, 3H, COCH₃), 1.68 (d, 3H, J=5.2 Hz, CHCH₃).

Example 29

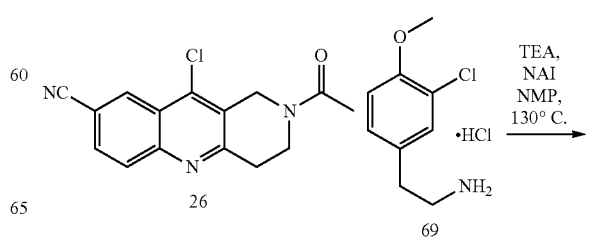

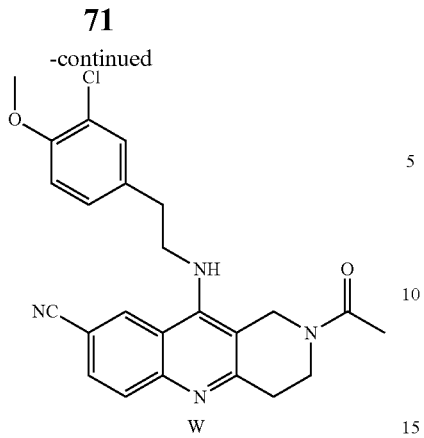

W

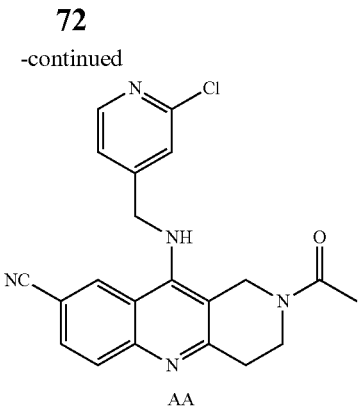

AA

A mixture of 26 (0.175 mmol), 69 (0.526 mmol), TEA (0.7 mmol) and NaI (0.017 mmol) in NMP (1 mL) was heated to 130° C. and stirred overnight. The mixture was cooled down and AcOEt (10 mL) was added. The organic layer was washed with $H_2O$ (2×10 mL), dried over $Na_2SO_4$, filtered and evaporated under reduce pressure. Flash Chromatography (eluent: 2% MeOH in DCM) gave the desired product W (21% yield). MS ESI (m/z) 435 (M+H)$^+$; $^1$H NMR (400 MHz, CDCl$_3$) δ 8.19 (s, 1H), 8.01 (s, 1H), 7.73 (d, 1H, J=8.8 Hz), 7.17 (s, 1H), 7.11 (dd, 1H, J$_1$=2.0, J$_2$=8.4 Hz), 6.92 (d, 1H, J=9.0 Hz), 4.62 (s, 2H), 3.91-3.85 (m, 6H), 3.81 (t, 2H, J=6.0 Hz), 3.23 (s, 2H), 2.95 (t, 2H, J=6.0 Hz), 2.22 (s, 3H).

Compounds exhibited PDE5 inhibition in the nanomolar range or below. Exemplary inhibition of representative compounds is shown in Table 4.

TABLE 4

PDE5 Inhibition of Representative Compounds.

| R$^3$ | R$^8$ | R$^5$ | A  | X      | V    | W    | m | n | R$^2$ | R$^1$ | cmpd | PDE5 IC$_{50}$ (nM) |
|-------|-------|-------|----|--------|------|------|---|---|-------|-------|------|----------------------|
| CN    | H     | Ac    | NH | CH$_2$ | bond | bond | 1 | 2 | OCF$_3$ | Cl  | Q    | 337                  |
| CN    | H     | Ac    | NH | CH$_2$ | bond | bond | 1 | 2 | F     | Cl    | R    | 1.5                  |
| CN    | H     | Ac    | NH | bond   | bond | bond | 1 | 2 | OMe   | Cl    | S    | 593                  |
| CN    | H     | Ac    | NH | bond   | bond | bond | 1 | 2 | Cl    | OMe   | T    | 425                  |
| CN    | H     | Ac    | NH | CD$_2$ | bond | bond | 1 | 2 | OMe   | Cl    | U    | 0.044                |
| CN    | H     | Ac    | NH | CHMe   | bond | bond | 1 | 2 | OMe   | Cl    | V    | 26.9                 |
| CN    | H     | Ac    | NH | (CH$_2$)$_2$ | bond | bond | 1 | 2 | OMe | Cl | W | 10.6                 |

Benzo[b][1,6]naphthyridine derivatives—Formula Ia

Example 30

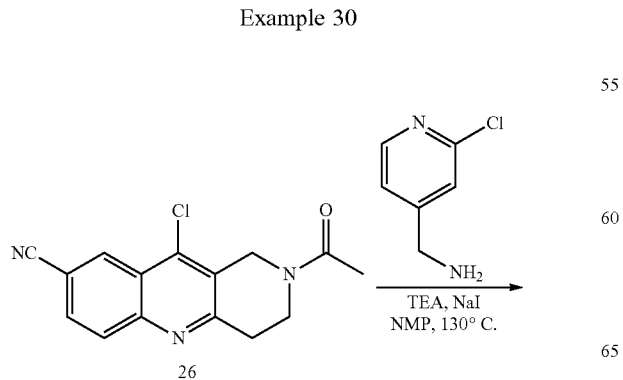

Example 31

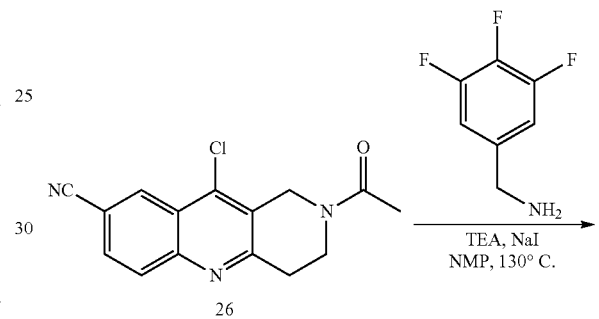

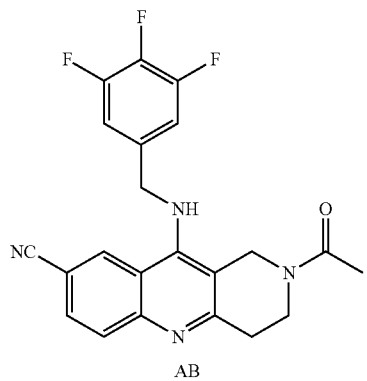

AB

Example 32
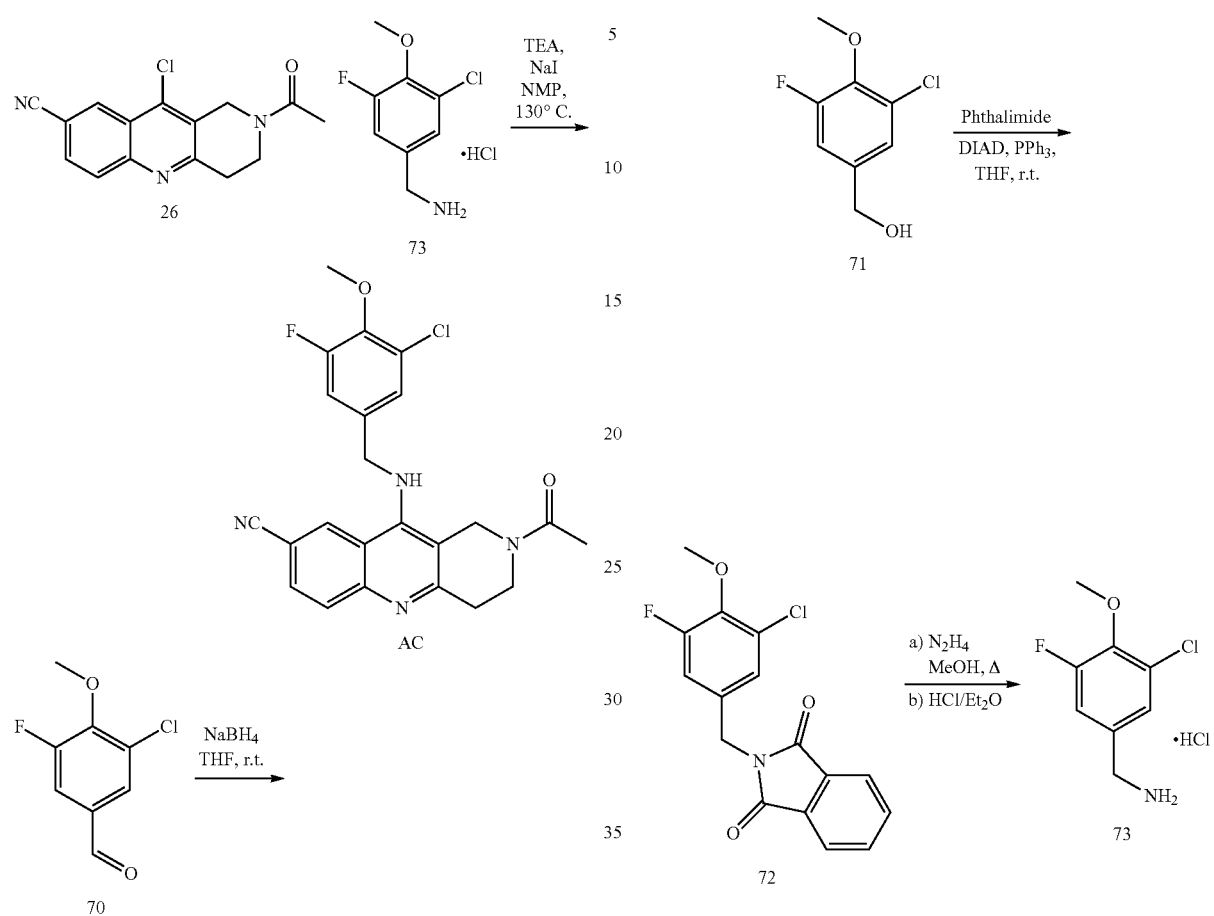
TABLE 5
PDE5 Inhibition of Representative Compounds-Formula Ia.
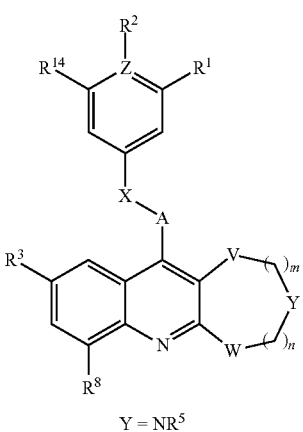
Y = NR$^5$
| R$^3$ | R$^8$ | R$^5$ | A | X | V | W | m | n | R$^2$ | R$^1$ | Z | R | cmpd | PDE5 IC$_{50}$ (nM) |
|---|---|---|---|---|---|---|---|---|---|---|---|---|---|---|
| CN | H | Ac | NH | CH$_2$ | bond | bond | 1 | 2 | — | Cl | N | H | AA | 57 |
| CN | H | Ac | NH | CH$_2$ | bond | bond | 1 | 2 | F | F | C | F | AB | 3.3 |
| CN | H | Ac | NH | CH$_2$ | bond | bond | 1 | 2 | OMe | Cl | C | F | AC | 0.32 |

2,3-dihydro-1H-pyrrolo[3,4-b]quinolin-1-one derivatives, with deuterium (D)

Example 33

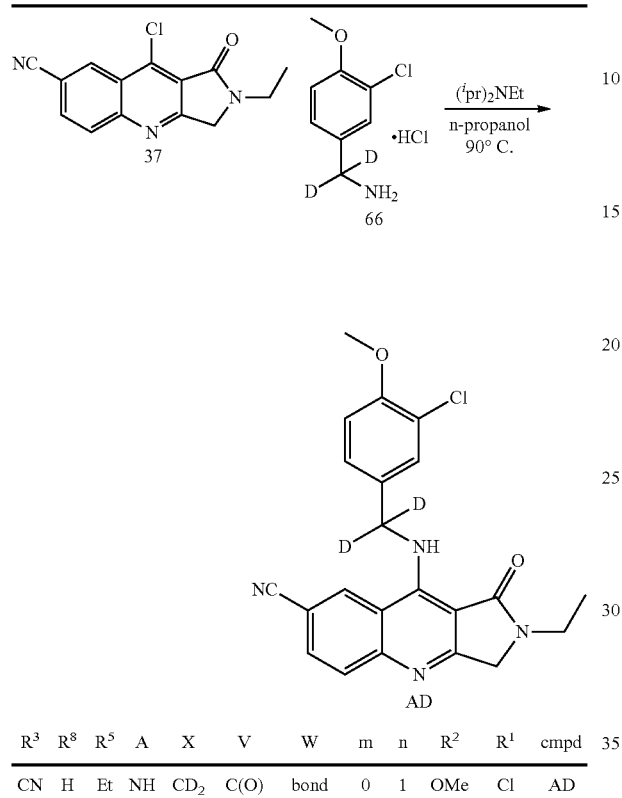

| R³ | R⁸ | R⁵ | A | X | V | W | m | n | R² | R¹ | cmpd |
|---|---|---|---|---|---|---|---|---|---|---|---|
| CN | H | Et | NH | CD₂ | C(O) | bond | 0 | 1 | OMe | Cl | AD |

The following prophetic examples are provided to illustrate other aspects of the present invention:

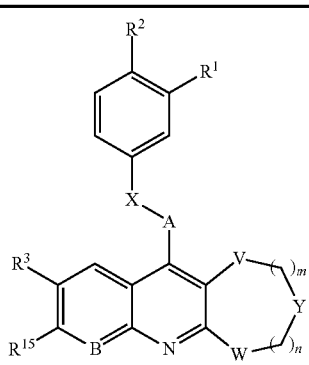

Y = NR⁵; B = CR¹⁶ or N

| R³ | R⁵ | R¹⁵ | R¹⁶ | B | A | X | V | W | m | n | R² | R¹ | cmpd |
|---|---|---|---|---|---|---|---|---|---|---|---|---|---|
| CN | Ac | H | — | N | NH | CD₂ | bond | bond | 1 | 2 | OMe | Cl | BA |
| CN | Ac | H | F | C | NH | CD₂ | bond | bond | 1 | 2 | OMe | Cl | BB |
| CN | Ac | F | H | C | NH | CD₂ | bond | bond | 1 | 2 | OMe | Cl | BC |
| CN | Ac | H | OH | C | NH | CD₂ | bond | bond | 1 | 2 | OMe | Cl | BD |
| CN | Ac | OH | H | C | NH | CD₂ | bond | bond | 1 | 2 | OMe | Cl | BE |
| CN | Ac | H | OMe | C | NH | CD₂ | bond | bond | 1 | 2 | OMe | Cl | BF |
| CN | Ac | OMe | H | C | NH | CD₂ | bond | bond | 1 | 2 | OMe | Cl | BG |

Example 34
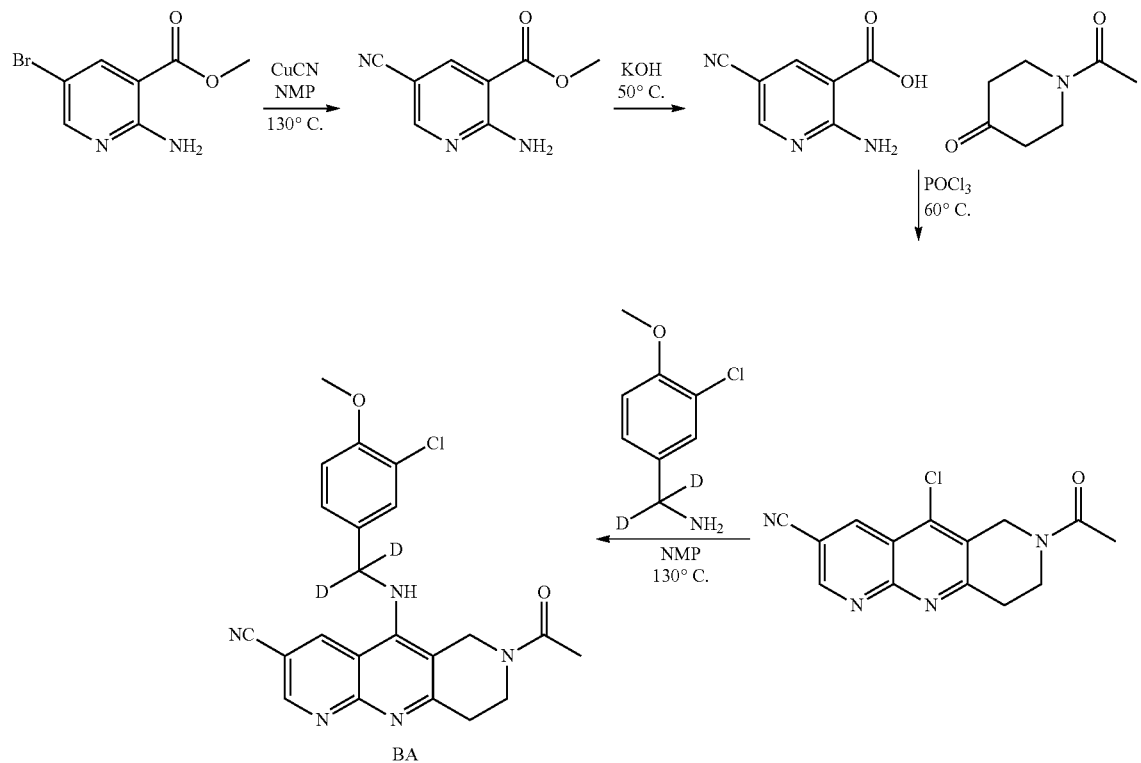
Example 35
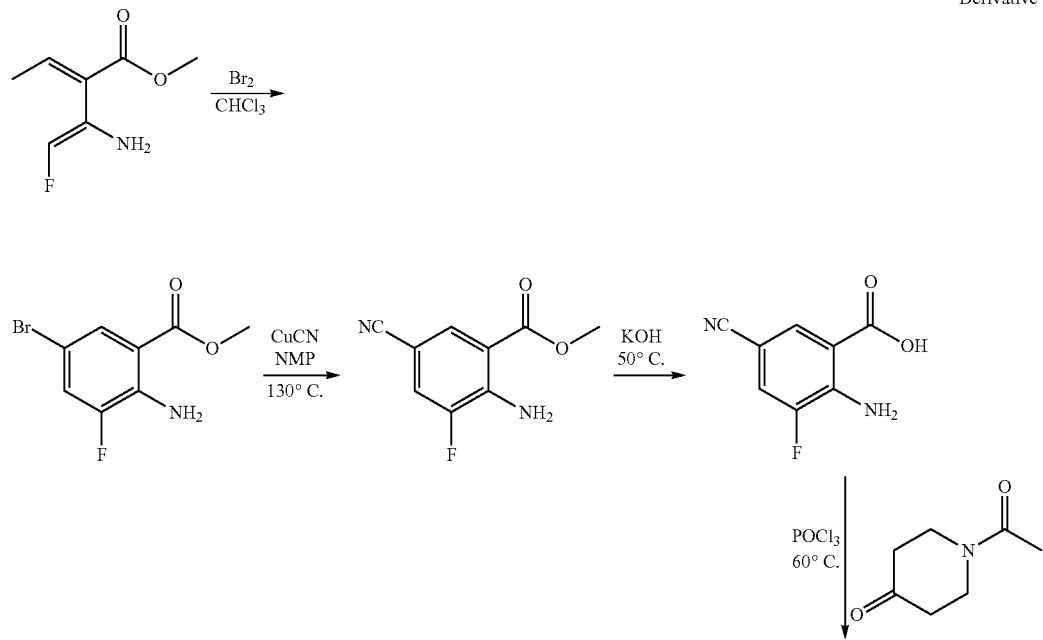

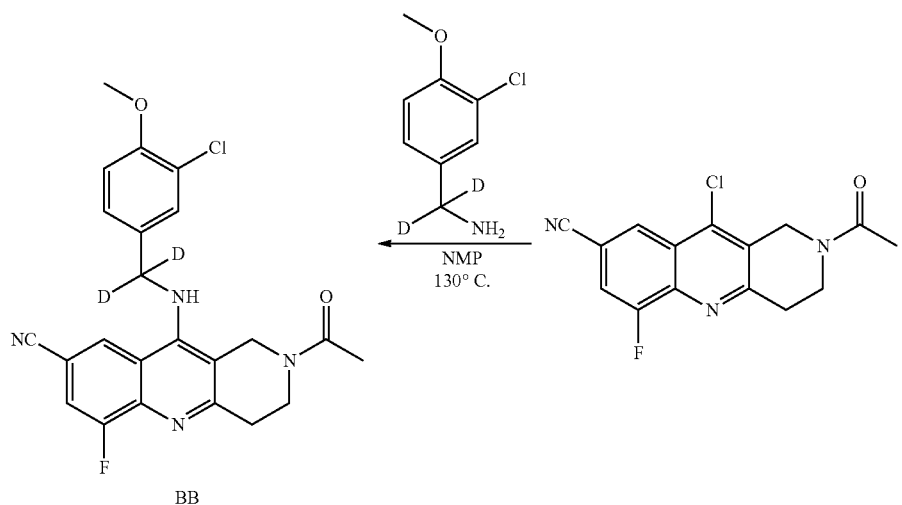
Example 36
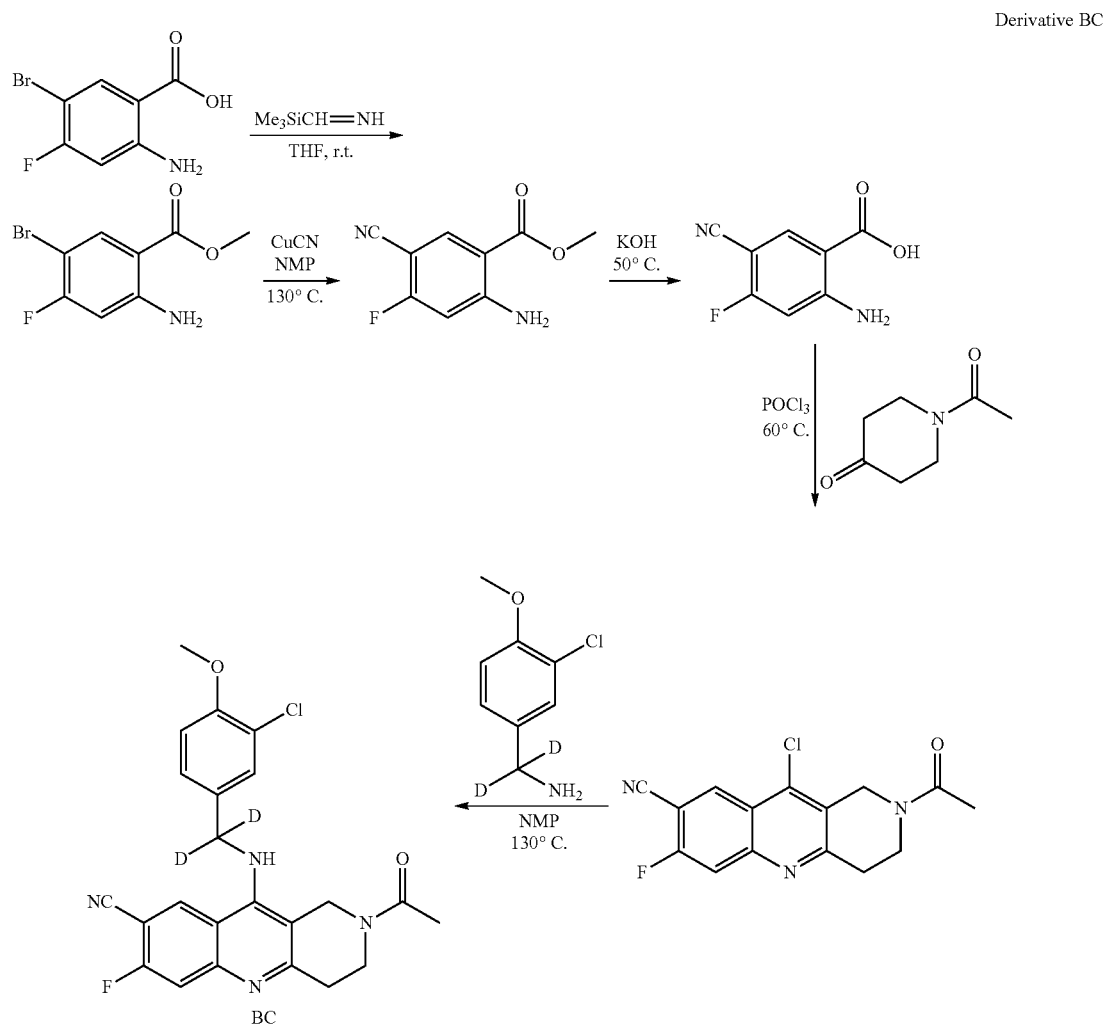

Example 37
Derivative BD & BF
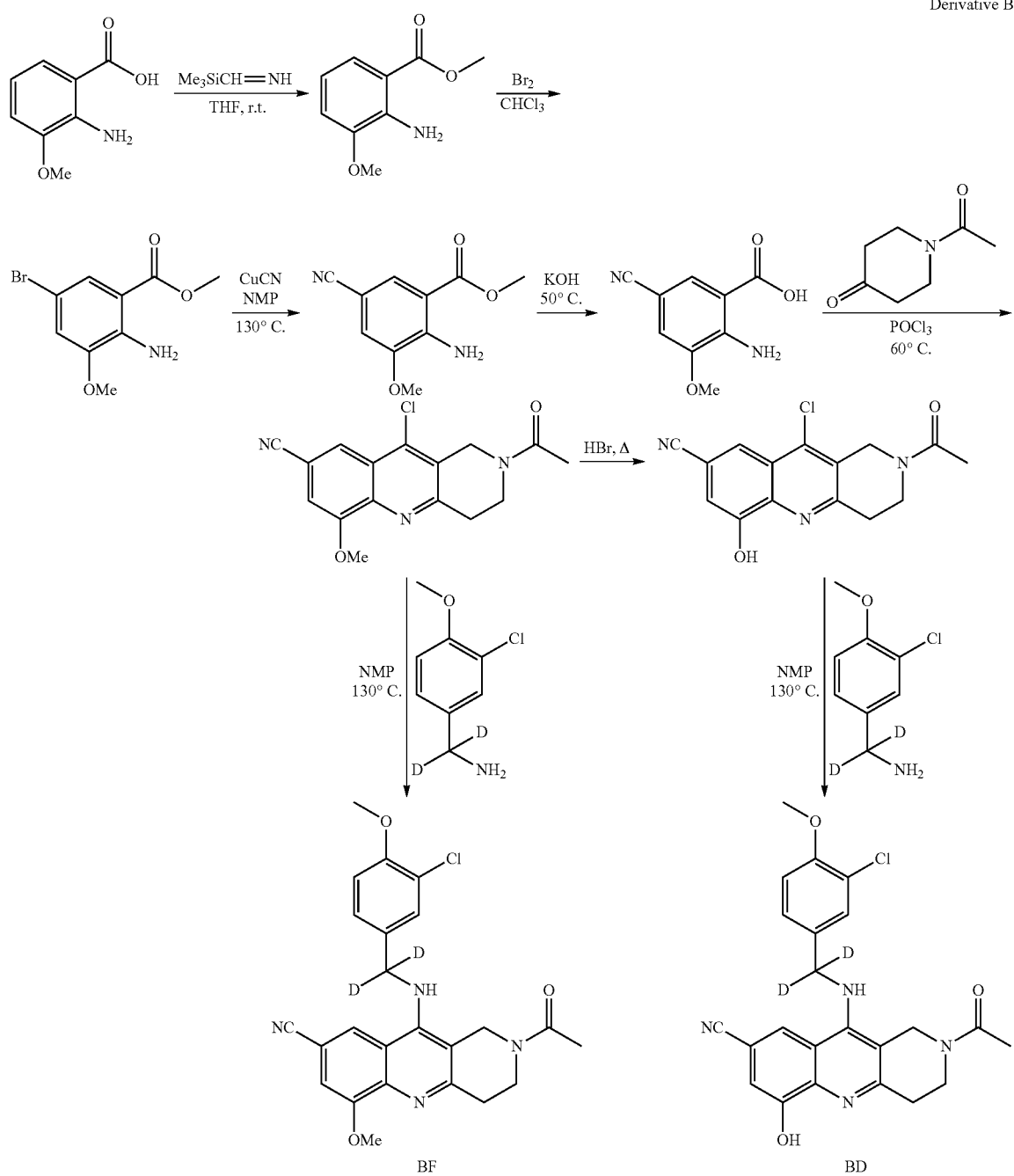
Example 38
Derivative BE & BG
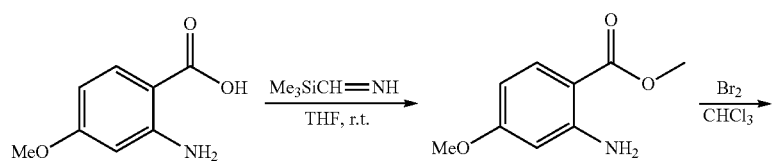

-continued

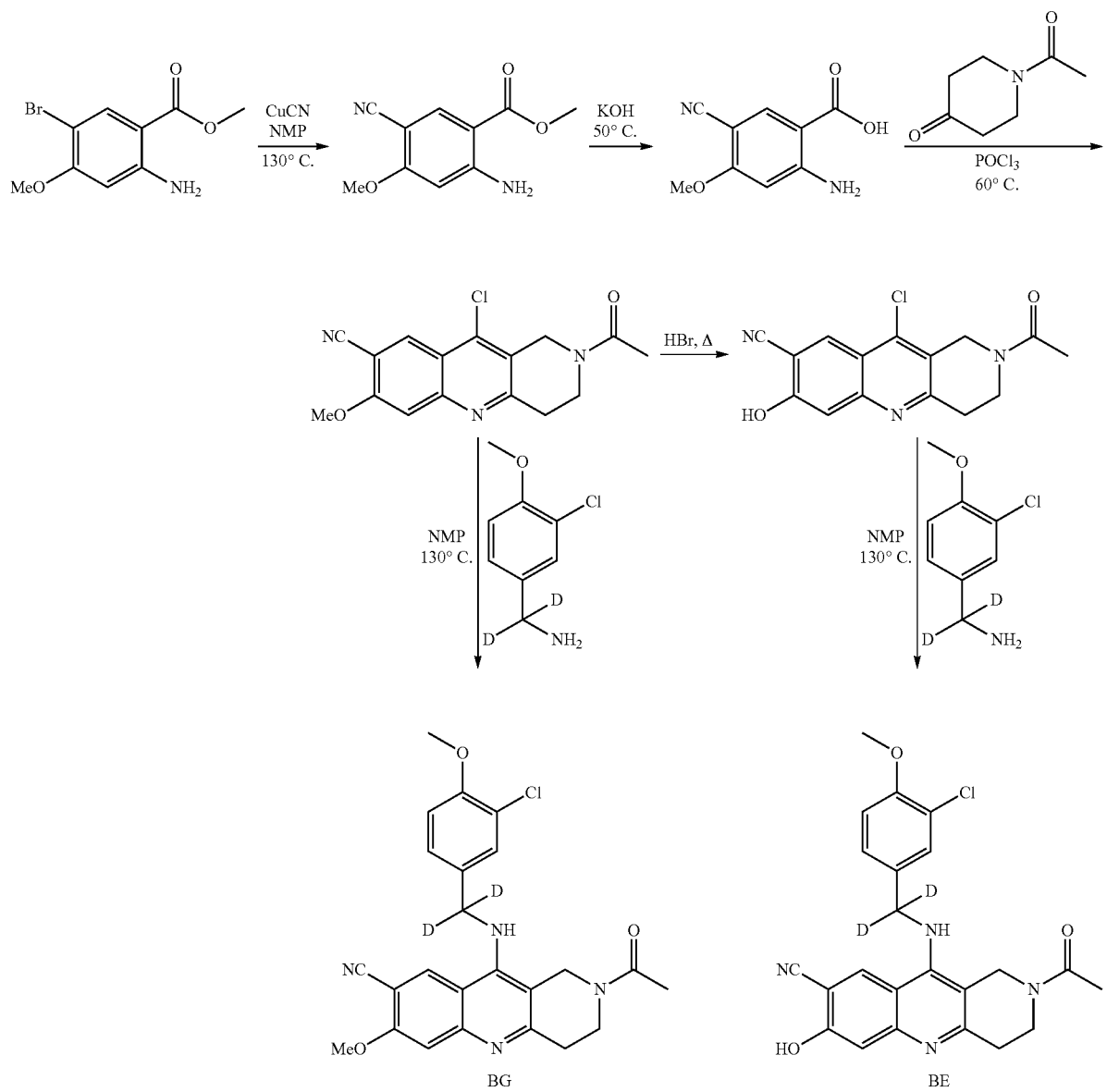

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of formula (I),

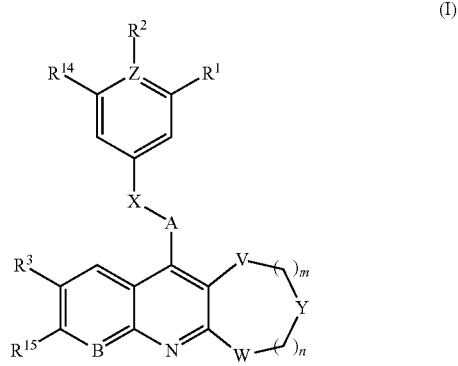

or a pharmaceutically acceptable salt or tautomer thereof, wherein
A is O or $NR^4$;
B is $CR^{16}$ or N;
V is a bond or C(O);
W is a bond;
X is —($C_1$-$C_3$)-alkyl, C(O), S, S(O), $S(O)_2$ or ($C_1$-$C_3$)-alkyl substituted with at least one D;
Y is $NR^5$ or O;
Z is $CR^2$ or N;
$R^1$ is halogen or —($C_1$-$C_6$)-haloalkyl;
$R^2$ is —$OR^6$;
$R^3$ is hydrogen, —OMe, —$CF_3$, —CN or halogen;
$R^4$ is hydrogen or —($C_1$-$C_3$)-alkyl;
$R^5$ is hydrogen, —($C_1$-$C_3$)-alkyl, —($C_3$-$C_5$)-cycloalkyl, —C(O)$R^7$, —C(O)O$R^7$, —C(O)N($R^7$)$_2$, or —S(O)$_2R^7$;
$R^6$ is hydrogen, —($C_1$-$C_6$)-alkyl, —($C_1$-$C_6$)-haloalkyl, or —($C_3$-$C_8$)-cycloalkyl;
$R^7$ is independently hydrogen, —($C_1$-$C_6$)-alkyl, —($C_1$-$C_6$)-haloalkyl, or aryl;
$R^{14}$ is hydrogen, halogen or —($C_1$-$C_6$)-haloalkyl;
$R^{15}$ is hydrogen, —$OR^{17}$, —OH or halogen;
$R^{16}$ is hydrogen, —($C_1$-$C_6$)-alkyl, —($C_1$-$C_6$)-haloalkyl, —($C_3$-$C_8$)-cycloalkyl, heterocycle, —$OR^{17}$, —OH or halogen;
$R^{17}$ is hydrogen, —($C_1$-$C_6$)-alkyl, —($C_1$-$C_6$)-haloalkyl, or —($C_3$-$C_8$)-cycloalkyl; and
m and n are each 0, 1, 2, or 3, provided that the sum of m+n is an integer from 1.

2. The compound of claim 1, having formula (Ia):

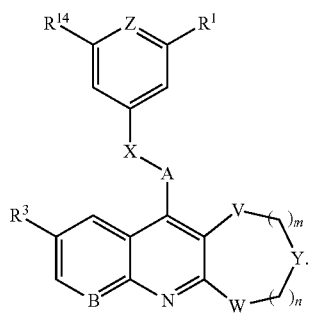

3. The compound of claim 1, having formula (Ib):

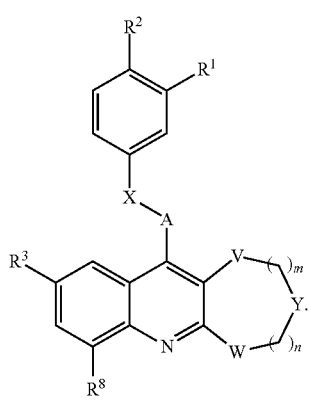

4. The compound of claim 1, having formula (Ic):

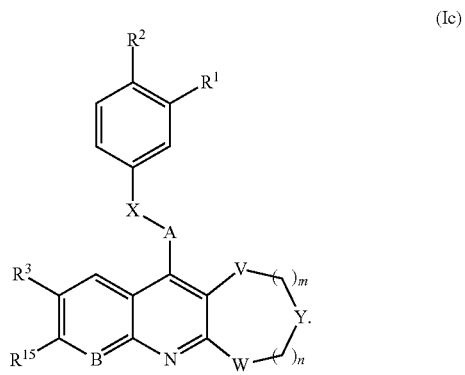

5. The compound of claim 1, wherein X is —($C_1$-$C_3$)-alkyl.

6. The compound of claim 1, wherein X is —($C_1$-$C_3$)-alkyl substituted with at least one D.

7. The compound of claim 1, wherein
A is $NR^4$;
V is a bond or C(O);
W is a bond;
X is ($C_1$-$C_3$)-alkyl or —($C_1$-$C_3$)-alkyl substituted with at least one D;
Y is $NR^5$;
$R^1$ is halogen or —($C_1$-$C_3$)-haloalkyl;
$R^2$ is —$OR^6$;
$R^3$ is hydrogen, —OMe, —$CF_3$, —CN or halogen;
$R^5$ is hydrogen, —($C_1$-$C_3$)-alkyl, —($C_3$-$C_5$)-cycloalkyl, or —C(O)$R^7$;
$R^6$ is —($C_1$-$C_3$)-alkyl or —($C_1$-$C_3$)-haloalkyl;
$R^7$ is —($C_1$-$C_3$)-alkyl;
$R^{16}$ is hydrogen or —($C_1$-$C_3$)-alkyl;
m and n are independently 0, 1 or 2, provided that the sum of m+n is an integer from 2-3.

8. The compound of claim 1, wherein
A is NH;
V is a bond or C(O);
W is a bond;
X is —($C_1$-$C_3$)-alkyl or —($C_1$-$C_3$)-alkyl substituted with at least one D;
Y is $NR^5$;
$R^1$ is halogen;
$R^2$ is —$OR^6$;
$R^3$ is hydrogen, —OMe, —$CF_3$, —CN or halogen;
$R^5$ is hydrogen, —($C_1$-$C_3$)-alkyl, or —C(O)$R^7$;
$R^6$ is —($C_1$-$C_3$)-alkyl;
$R^7$ is —($C_1$-$C_3$)-alkyl;
$R^{16}$ is hydrogen or —($C_1$-$C_3$)-alkyl;
m is 0 or 1; and
n is 2.

9. The compound of claim 1, wherein
A is NH;
V is a bond or C(O);
W is a bond;
X is —$CH_2$— or —$CD_2$—;
Y is $NR^5$;
$R^1$ is halogen;
$R^2$ is —$OCH_3$;
$R^3$ is hydrogen, —OMe, —$CF_3$, —CN or halogen;
$R^5$ is hydrogen, —($C_1$-$C_3$)-alkyl, or —C(O)$CH_3$;
$R^{16}$ is hydrogen or —($C_1$-$C_3$)-alkyl;
m is 0 or 1; and
n is 2.

10. The compound of claim 1, wherein
V and W are each a bond;
X is —($C_1$-$C_3$)-alkyl or —($C_1$-$C_3$)-alkyl substituted with at least one D;
Y is $NR^5$; and
m and n are each 0, 1 or 2, provided that the sum of m+n is an integer from 2-3.

11. The compound of claim 1, wherein
A is NH;
V is C(O);
W is a bond;
X is $CH_2$ or $CD_2$;
Y is $NR^5$;
$R^1$ is halogen or —($C_1$-$C_3$)-haloalkyl;
$R^2$ is —$OR^6$;
$R^3$ is hydrogen, —OMe, —$CF_3$, —CN or halogen;
$R^5$ is hydrogen, —($C_1$-$C_3$)-alkyl, or $C(O)R^7$;
$R^6$ is hydrogen, —($C_1$-$C_3$)-alkyl, or —($C_1$-$C_3$)-haloalkyl;
$R^7$ is hydrogen or —($C_1$-$C_3$)-alkyl;
$R^{16}$ is hydrogen, —($C_1$-$C_3$)-alkyl, —($C_1$-$C_3$)-haloalkyl, or —($C_3$-$C_5$)-cycloalkyl;
m is 0 or 1; and
n is 2.

12. The compound of claim 1, wherein
A is NH;
V is C(O);
W is a bond;
X is $CH_2$ or $CD_2$;
Y is $NR^5$;
$R^1$ is halogen;
$R^2$ is —$OCH_3$;
$R^3$ is hydrogen, —OMe, —$CF_3$, —CN or halogen;
$R^5$ is hydrogen, —($C_1$-$C_3$)-alkyl, or $C(O)R^7$;
$R^7$ is —($C_1$-$C_3$)-alkyl;
$R^{16}$ is hydrogen or —($C_1$-$C_3$)-alkyl; m is 0; and
n is 2.

13. The compound of claim 1, wherein A is NH;
V and W are each a bond;
X is $CH_2$ or $CD_2$;
Y is $NR^5$;
$R^1$ is halogen or —($C_1$-$C_3$)-haloalkyl;
$R^2$ is —$OR^6$;
$R^3$ is hydrogen, —OMe, —$CF_3$, —CN or halogen;
$R^5$ is hydrogen, —($C_1$-$C_3$)-alkyl, or $C(O)R^7$;
$R^6$ is hydrogen, —($C_1$-$C_2$)-alkyl, or —($C_1$-$C_2$)-haloalkyl;
$R^7$ is —($C_1$-$C_3$)-alkyl;
$R^{16}$ is hydrogen, —($C_1$-$C_3$)-alkyl, —($C_1$-$C_3$)-haloalkyl, or —($C_3$-$C_5$)-cycloalkyl;
m is 0 or 1; and
n is 2.

14. The compound of claim 1, wherein
A is NH;
V and W are each a bond;
X is $CH_2$ or $CD_2$;
Y is $NR^5$;
$R^1$ is chlorine;
$R^2$ is —$OCH_3$;
$R^3$ is —CN;
$R^5$ is hydrogen or —($C_1$-$C_3$)-alkyl;
$R^{16}$ is hydrogen or —($C_1$-$C_3$)-alkyl;
m is 1; and
n is 2.

15. The compound of claim 1, wherein
A is NH;
V and W are each a bond;
X is $CH_2$ or $CD_2$;
Y is $NC(O)CH_3$;
$R^1$ is halogen;
$R^2$ is —$OCH_3$;
$R^3$ is hydrogen, —OMe, —$CF_3$, —CN or halogen;
$R^{16}$ is hydrogen;
m is 1; and
n is 2.

16. The compound of claim 1, wherein the compound is:

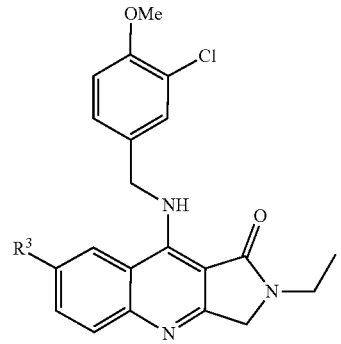

wherein $R^3$ is —OMe, —$CF_3$, or —CN or a pharmaceutically acceptable salt or tautomer thereof.

17. The compound of claim 1, wherein the compound is:

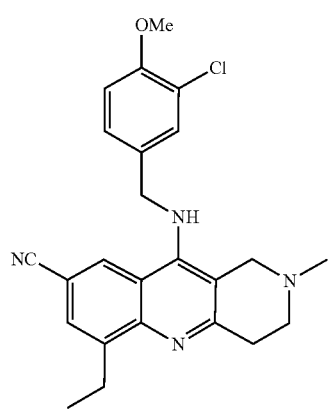

or a pharmaceutically acceptable salt or tautomer thereof.

18. The compound of claim 1, wherein the compound is:

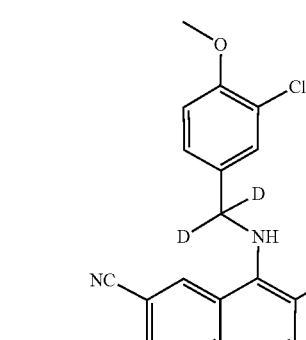

or a pharmaceutically acceptable salt or tautomer thereof.

19. The compound of claim 1, wherein the compound is:

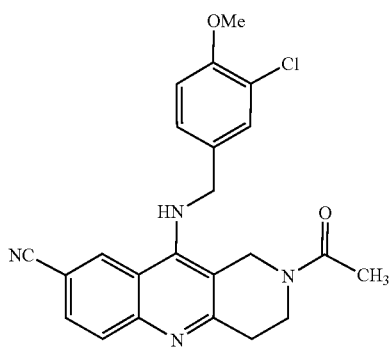

or a pharmaceutically acceptable salt or tautomer thereof.

20. A composition comprising a compound of claim 1 and a pharmaceutically acceptable carrier.

21. A method of treating neurodegenerative disease in a subject in need thereof comprising administration of a therapeutically effective amount of a compound of claim 1 to said subject.

22. The method of claim 21, wherein the disease is Alzheimer's Disease.

23. A method of increasing long-term potentiation in a subject comprising administration of a therapeutically effective amount of a compound of claim 1 to said subject.

24. A method of improving memory in a subject comprising administration of a therapeutically effective amount of a compound of claim 1 to said subject.

25. The method of claim 24, wherein the subject has a neurodegenerative disease.

26. The method of claim 25, wherein the neurodegenerative disease is Alzheimer's Disease.

* * * * *